(12) United States Patent
Tani et al.

(10) Patent No.: US 8,574,463 B2
(45) Date of Patent: Nov. 5, 2013

(54) METAL COMPLEX DYE, PHOTOELECTRIC CONVERSION ELEMENT AND DYE-SENSITIZED SOLAR CELL

(71) Applicant: Fujifilm Corporation, Tokyo (JP)

(72) Inventors: Yukio Tani, Odawara (JP); Tatsuya Susuki, Odawara (JP); Katsumi Kobayashi, Odawara (JP); Keizo Kimura, Odawara (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/689,058

(22) Filed: Nov. 29, 2012

(65) Prior Publication Data

US 2013/0087203 A1    Apr. 11, 2013

Related U.S. Application Data

(63) Continuation of application No. PCT/JP2011/062255, filed on May 27, 2011.

(30) Foreign Application Priority Data

Jun. 2, 2010   (JP) ................. 2010-127308
May 13, 2011   (JP) ................. 2011-108469

(51) Int. Cl.
 *C01G 55/00*   (2006.01)
 *H01B 1/12*   (2006.01)

(52) U.S. Cl.
 USPC ............. 252/501.1; 136/263; 546/12; 546/6; 252/500

(58) Field of Classification Search
 USPC ..................... 136/263; 546/12; 252/501.1
 See application file for complete search history.

(56) References Cited

U.S. PATENT DOCUMENTS 4,927,721 A    5/1990   Gratzel et al.
2007/0265443 A1   11/2007   Wu et al.

FOREIGN PATENT DOCUMENTS

CN    101412855 A    4/2009
JP     9-173840 A    7/1997

(Continued)

OTHER PUBLICATIONS

Brian O'Regan, et al., "A low-cost, high-efficiency solar cell based on dye-sensitized colloidal TiO$_2$ films", Letters to Nature, Oct. 24, 1991, pp. 737-740, vol. 353.

(Continued)

*Primary Examiner* — Harold Pyon
*Assistant Examiner* — Katie L Hammer
(74) *Attorney, Agent, or Firm* — Sughrue Mion, PLLC

(57) ABSTRACT

A metal complex dye, containing a ligand LL1 having a structure represented by Formula (I):

wherein $R^1$ and $R^2$ represent a specific substituent; $L^1$ and $L^2$ represent a group composed of at least one kind of group selected from the group consisting of an ethenylene group, an ethynylene group and an arylene group, and conjugate with $R^1$ or $R^2$, and the bipyridine; the ethenylene group and the arylene group may be substituted or unsubstituted; $R^3$ and $R^4$ represent a substituent; n1 and n2 represent an integer of 0 to 3; $A^1$ and $A^2$ represent an acidic group or a salt thereof; and n3 and n4 represent an integer of 0 to 3.

17 Claims, 1 Drawing Sheet

(56) References Cited

FOREIGN PATENT DOCUMENTS

| | | |
|---|---|---|
| JP | 2001-291534 A | 10/2001 |
| JP | 2007-197424 A | 8/2007 |
| JP | 2008-021496 A | 1/2008 |
| JP | 2008-174734 A | 7/2008 |
| JP | 4576494 B2 | 11/2010 |
| TW | 200938594 A | 9/2009 |
| WO | 94/04497 A1 | 3/1994 |
| WO | 2007/091525 A1 | 8/2007 |
| WO | 2009/082163 A2 | 7/2009 |
| WO | 2010055470 A1 | 5/2010 |

OTHER PUBLICATIONS

Office Action ("Preliminary Notice of First Office Action") issued Dec. 26, 2012 for corresponding Taiwanese Patent Application No. 100119220.

Chinese Office Action dated May 6, 2013 for corresponding Chinese Patent Application No. 201180019559.3.

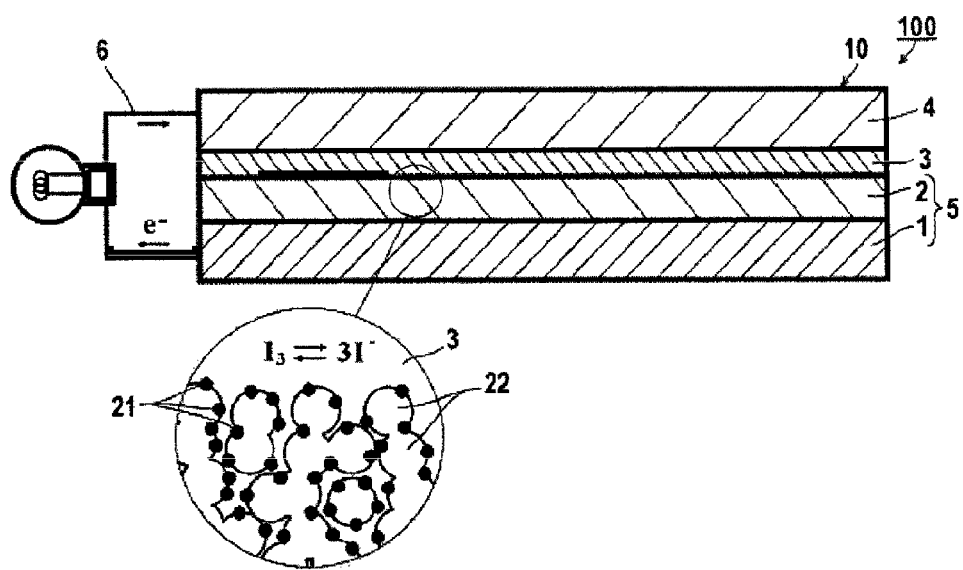

METAL COMPLEX DYE, PHOTOELECTRIC CONVERSION ELEMENT AND DYE-SENSITIZED SOLAR CELL

TECHNICAL FIELD

The present invention relates to a metal complex dye that is excellent in durability and photoelectric conversion characteristics, a photoelectric conversion element containing semiconductor fine particles prepared by using the same as a sensitizing dye, and a dye-sensitized solar cell using such a photoelectric conversion element.

BACKGROUND ART

As a solar cell used for photovoltaic power generation, a solar cell composed of single crystal silicon, polycrystal silicon, amorphous silicon, or a compound such as cadmium telluride or copper indium selenide is a main research and development target, and part thereof is put in practical use. However, in order to widely expand use of these solar cells to an application such as a household power supply, these solar cells have problems such as difficulty in manufacturing the cells at a low cost or securing a raw material, and also a long energy payback time. These problems are required to be overcome. Meanwhile, many proposals have been made for solar cells produced by using an organic material for the purpose of increasing an area of a light-condensing part and providing the cells at a low price. However, the solar cells that have been applied so far have generally had a low conversion efficiency and a poor durability in many cases.

Under such a situation, a wet photoelectric conversion element that applies, as a working electrode, a titanium dioxide porous thin film spectrally sensitized with a ruthenium complex dye and a solar cell, and a material for preparing the same and a manufacturing technology therefor have been proposed (see, for example, Patent Literatures 1 and 2, and Non-Patent Literature 1). A first advantage of the wet photoelectric conversion elements described in these Literatures is to allow provision of the photoelectric conversion element at a low price because a less expensive oxide semiconductor such as titanium dioxide can be used without purification to a high purity. A second advantage of these wet photoelectric conversion elements is to absorb light in almost all wavelength regions of visible light and allow conversion of light into electricity because the dye to be used can absorb light in a wide-ranged wavelength band.

As a metal complex dye to be used for the photoelectric conversion element, N719, Z907, J2 or the like has been developed so far. A photoelectric conversion element prepared by using N719 shows a high photoelectric conversion efficiency initially. However, a decrease in conversion efficiency after use is large, and the cell has a problem of durability. Whereas, a photoelectric conversion element prepared by using Z907 has a small decrease in conversion efficiency after use. However, Z907 has a lower initial value per se of photoelectric conversion efficiency, as compared with N719.

Furthermore, a photoelectric conversion element containing semiconductor fine particles sensitized with a metal complex dye having a specific structure has been proposed (see, for example, Patent Literature 3). However, even the photoelectric conversion element described in Patent Literature 3 is not satisfactory in view of durability. J2 has also been developed as a dye having a high initial conversion efficiency (Patent Literature 4). However, the photoelectric conversion element is not satisfactory even with the initial conversion efficiency and durability of J2.

Consequently, a need is arisen for a dye that is excellent in the photoelectric conversion characteristics such as the conversion efficiency, and durability with a small decrease in the photoelectric conversion characteristics even after use over a long period of time, a photoelectric conversion element prepared by using the same as a sensitizing dye, and a dye-sensitized solar cell composed of such a photoelectric conversion element.

CITATION LIST

Patent Literatures

Patent Literature 1: U.S. Pat. No. 4,927,721
Patent Literature 2: WO 94/04497
Patent Literature 3: JP-A-2001-291534 ("JP-A" means unexamined published Japanese patent application)
Patent Literature 4: Japanese Patent No. 4576494

Non-Patent Literature

Non-Patent Literature 1: Nature, vol. 353, p. 737-740 (1991)

SUMMARY OF THE INVENTION

Technical Problem

A problem of the present invention is to provide a metal complex dye that is excellent in photoelectric conversion characteristics such as conversion efficiency, and durability with a small decrease in the photoelectric conversion characteristics even after use over a long period of time; a photoelectric conversion element prepared by using the same as a sensitizing dye; and a dye-sensitized solar cell composed of such a photoelectric conversion element.

Solution to Problem

The present inventors have diligently repeated examinations. As a result, they have found that a metal complex dye having a specific bipyridine ligand containing a specific substituent is excellent in durability and photoelectric conversion characteristics, and a dye-sensitized solar cell produced by using a photoelectric conversion element containing semiconductor fine particles prepared by using the same as a sensitizing dye satisfies an excellent conversion efficiency and durability. The present invention has been achieved based on this finding.

The problems of the present invention can be solved by the following means.

<1> A metal complex dye, comprising a ligand LL1 having a structure represented by Formula (I):

LL1

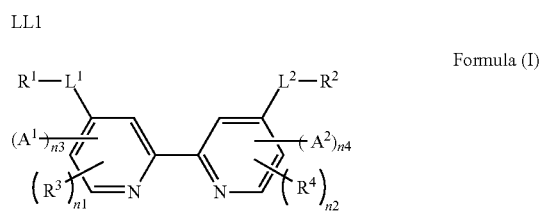

Formula (I)

wherein
$R^1$ and $R^2$ each independently represent a group represented by any of Formulas (II) to (VIII);

$L^1$ and $L^2$ each independently represent a group composed of at least one kind of group selected from the group consisting of an ethenylene group, an ethynylene group and an arylene group, and conjugate with $R^1$ or $R^2$, and the bipyridine; the ethenylene group and the arylene group may be substituted or unsubstituted;

$R^3$ and $R^4$ each independently represent a substituent; n1 and n2 each independently represent an integer of 0 to 3; when n1 is an integer of 1 or more, $R^3$ may be bonded with $L^1$ to form a ring; when n2 is an integer of 1 or more, $R^4$ may be bonded with $L^2$ to form a ring; when n1 is an integer of 2 or more, $R^3$'s may be the same or different from each other, or $R^3$'s may be bonded to each other to form a ring; when n2 is an integer of 2 or more, $R^4$'s may be the same or different from each other, or $R^4$'s may be bonded to each other to form a ring; when n1 and n2 each are an integer of 1 or more, $R^3$ and $R^4$ may be bonded to each other to form a ring;

$A^1$ and $A^2$ each independently represent an acidic group or a salt thereof; and n3 and n4 each independently represent an integer of 0 to 3;

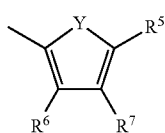

Formula (II)

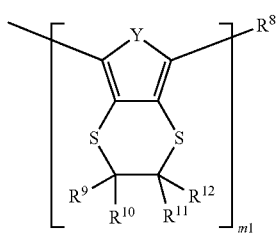

Formula (III)

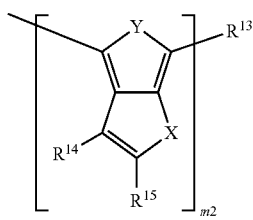

Formula (IV)

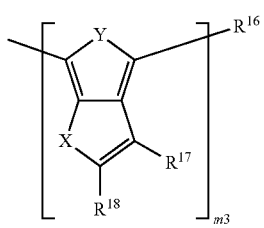

Formula (V)

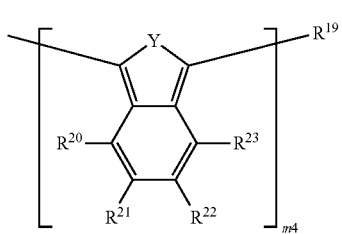

Formula (VI)

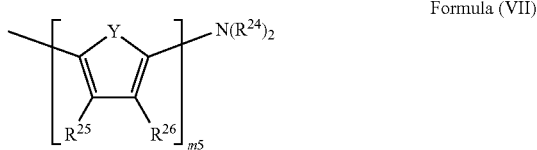

Formula (VII)

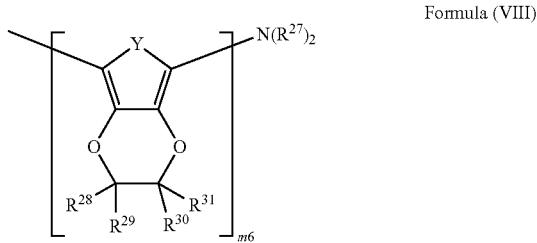

Formula (VIII)

wherein $R^5$, $R^8$, $R^{13}$, $R^{16}$ and $R^{19}$ each independently represent an alkynyl group or an aryl group, each of which may have a substituent;

$R^6$, $R^9$ to $R^{12}$, $R^{14}$, $R^{15}$, $R^{17}$, $R^{18}$, $R^{20}$ to $R^{23}$, $R^{25}$, $R^{26}$ and $R^{28}$ to $R^{31}$ each independently represent a hydrogen atom, an alkyl group, an alkenyl group, an alkynyl group, an alkoxy group, an alkylthio group, an aryl group, an aryloxy group, an arylthio group, an amino group, a heterocyclic group or a halogen atom; at least one of $R^{25}$ and $R^{26}$ represents an alkyl group;

$R^7$ represents a hydrogen atom, an alkyl group, an alkenyl group, an alkynyl group, an alkylthio group or a halogen atom;

$R^6$ and $R^7$, any of $R^9$ to $R^{12}$, $R^{14}$ and $R^{15}$, $R^{17}$ and $R^{18}$, any of $R^{20}$ to $R^{23}$, $R^{25}$ and $R^{26}$, and any of $R^{28}$ to $R^{31}$ may be bonded with each other to form a ring;

the two $R^{24}$'s and the two $R^{27}$'s present in the same characteristic group may be the same or different from each other, and each represent a hydrogen atom, an alkyl group, an alkenyl group or an alkynyl group, but $R^{24}$'s or $R^{27}$'s are not bonded with each other for forming a ring;

m1 to m6 each independently represent an integer of 1 to 5;

Y represents S, O, Se, Te or $NR^{32}$; and X represents S, Se, Te or $NR^{32}$; and $R^{32}$ represents a hydrogen atom, an alkyl group, an alkenyl group, an alkenyl group, an aryl group or a heterocyclic group.

<2> The metal complex dye described in the above item <1>, wherein $L^1$ and $L^2$ in Formula (I) each independently represent a substituted or unsubstituted ethenylene group and/or ethynylene group, and conjugate with $R^1$ or $R^2$, and the bipyridine.

<3> The metal complex dye described in the above item <1> or <2>, which is represented by Formula (IX):

M(LL1)(LL2)(Z)$_p$.CI  Formula (IX)

wherein M represents a metal atom; LL1 has the same meaning as LL1 in Formula (I);

LL2 represents a ligand represented by Formula (X); Z represents a monodentate or bidentate ligand; p represents an integer of 0 to 2; and CI represents a counter ion in the case where the counter ion is necessary to neutralize a charge in Formula (IX);

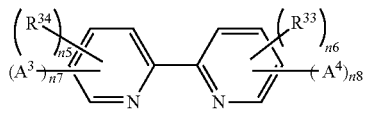

Formula (X)

wherein
$R^{33}$ and $R^{34}$ each independently represent a substituent; n5 and n6 each independently represent an integer of 0 to 3; when n5 is an integer of 2 or more, $R^{34}$'s may be the same or different from each other, or $R^{34}$'s may be bonded to each other to form a ring; when n6 is an integer of 2 or more, $R^{33}$'s may be the same or different from each other, or $R^{33}$'s may be bonded to each other to form a ring; when n5 and n6 each are an integer of 1 or more, $R^{33}$ and $R^{34}$ may be bonded to each other to form a ring;
$A^3$ and $A^4$ each independently represent an acidic group; and n7 and n8 each independently represent an integer of 1 to 4.
<4> The metal complex dye described in the above item <3>, wherein the metal atom M in Formula (IX) is Ru, Re, Rh, Pt, Fe, Os, Cu, Ir, Pd, W or Co.
<5> The metal complex dye described in the above item <3>, wherein the metal atom M in Formula (IX) is Ru.
<6> The metal complex dye described in any one of the above items <1> to <5>, wherein Y in Formulas (II) to (VIII) is S.
<7> The metal complex dye described in any one of the above items <3> to <6>, wherein the ligand LL2 is a ligand represented by Formula (XI):

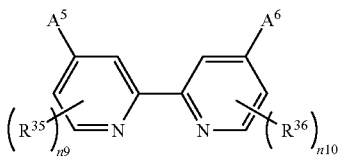

Formula (XI)

wherein
$A^5$ and $A^6$ each independently represent an acidic group; $R^{35}$ and $R^{36}$ each independently represent a substituent; n9 and n10 each independently represent an integer of 0 to 3; when n9 is an integer of 2 or more, $R^{35}$'s may be the same or different from each other, or $R^{35}$'s may be bonded to each other to form a ring; when n10 is an integer of 2 or more, $R^{36}$'s may be the same or different from each other, or $R^{36}$'s may be bonded to each other to form a ring; and when n9 and n10 each are an integer of 1 or more, $R^{35}$ and $R^{36}$ may be bonded to each other to form a ring.
<8> The metal complex dye described in any one of the above items <3> to <6>, wherein the ligand LL2 is a ligand represented by Formula (XII):

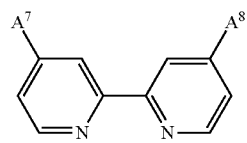

Formula (XII)

wherein $A^7$ and $A^8$ each independently represent a carboxyl group or a salt thereof.
<9> The metal complex dye described in any one of the above items <1> to <8>, wherein $R^1$ and $R^2$ in the ligand LL1 each are a group represented by any of Formula (II), Formula (VII) and Formula (VIII).
<10> The metal complex dye described in any one of the above items <1> to <9>, wherein $L^1$ and $L^2$ in the ligand LL1 each are an unsubstituted ethenylene group.
<11> The metal complex dye described in any one of the above items <3> to <10>, wherein the metal complex dye represented by Formula (IX) is represented by any of Formulas (XIII) to (XV):

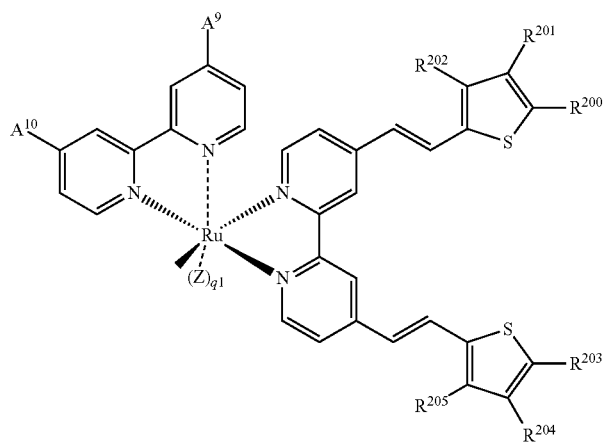

Formula (XIII)

-continued

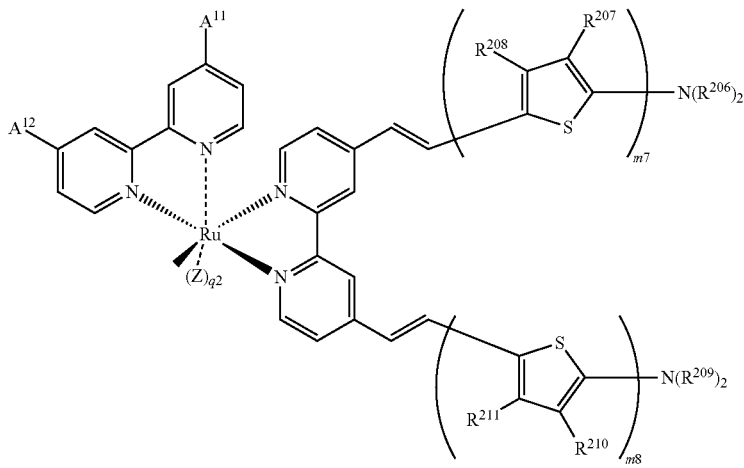

Formula (XIV)

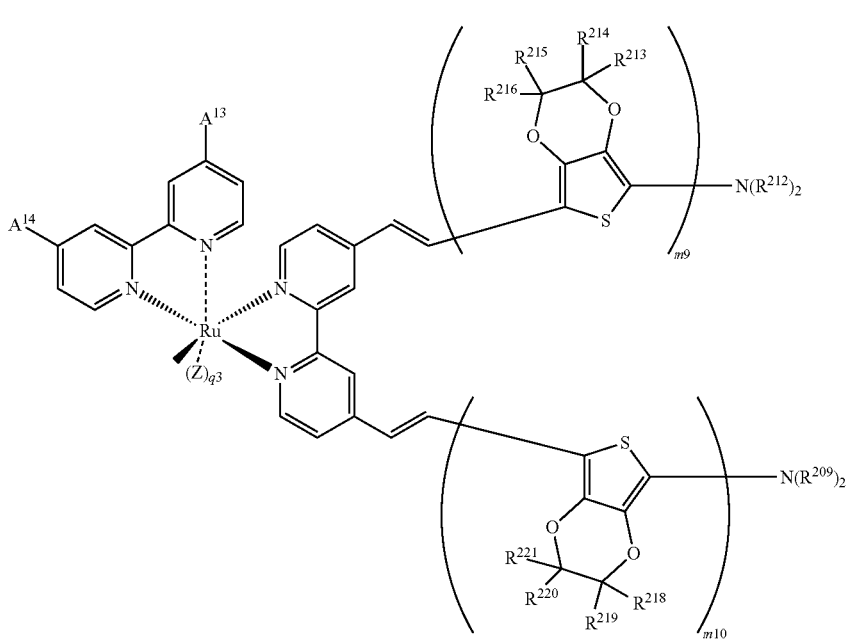

Formula (XV)

wherein
$A^9, A^{10}, A^{11}, A^{12}, A^{13}$ and $A^{14}$ each independently represent a carboxyl group or a salt thereof; $R^{200}$ and $R^{203}$ each have the same meaning as that of $R^5$ in Formula (II); $R^{202}, R^{205}, R^{207}, R^{208}, R^{210}, R^{211}, R^{213}$ to $R^{216}$ and $R^{218}$ to $R^{221}$ each have the same meaning as that of $R^6$ in Formula (II); at least one of $R^{207}$ and $R^{208}$ is an alkyl group; at least one of $R^{210}$ and $R^{211}$ is an alkyl group;

$R^{201}$ and $R^{204}$ each independently represent a hydrogen atom, an alkyl group, an alkenyl group, an alkynyl group, an alkylthio group or a halogen atom;

$R^{201}$ and $R^{202}$, $R^{204}$ and $R^{205}$, $R^{207}$ and $R^{208}$, $R^{210}$ and $R^{211}$, any of $R^{213}$ to $R^{216}$, and any of $R^{218}$ to $R^{221}$ may be bonded with each other to form a ring;

$R^{206}$ and $R^{209}$ each have the same meaning as that of $R^{24}$ in Formula (VII); $R^{212}$ and $R^{217}$ each have the same meaning as that of $R^{27}$ in Formula (VIII);

m7 to m10 each independently represent an integer of 1 to 5;
Z represents a monodentate or bidentate ligand; and q1 to q3 each independently represent an integer of 1 or 2.

<12> The metal complex dye described in the above item <11>, wherein metal complex dye represented by Formula (IX) is represented by Formula (XIII) or Formula (XV).

<13> The metal complex dye described in the above item <11>, wherein metal complex dye represented by Formula (IX) is represented by Formula (XIII).

<14> The metal complex dye described in any one of the above items <3> to <13>, wherein Z is isothiocyanate, isocyanate or isoselenocyanate.

<15> A photoelectric conversion element, comprising semiconductor fine particles sensitized with the metal complex dye described in any one of the above items <1> to <14>.

<16> A photoelectric conversion element, comprising semiconductor fine particles sensitized with a plurality of dyes, at least one of which is the metal complex dye described in any one of the above items <1> to <14>.

<17> The photoelectric conversion element described in the above item <16>, at least one of the plurality of dyes has a maximum absorption wavelength of 600 nm or more on the longest wavelength side in THF/water (=6:4, trifluoroacetic acid 0.1 v/v %) solution.

<18> A photoelectric conversion element, comprising:
an electrically conductive support; and
a semiconductor layer arranged so as to cover an electrically conductive surface of the electrically conductive support;
wherein the metal complex dye described in any one of the above items <1> to <14>, and a co-adsorbent having one carboxyl group or salt thereof are carried on a surface of semiconductor particles of the semiconductor layer.
<19> The photoelectric conversion element described in the above item <18>, wherein the co-adsorbent is represented by Formula (XVI):

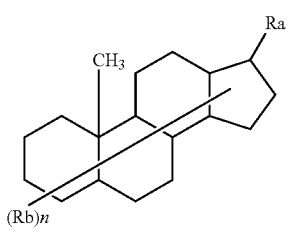

Formula (XVI)

wherein Ra represents an alkyl group having one (1) acidic group or salt thereof; Rb represents a substituent; n represents an integer of 0 or more; and when n is an integer of 2 or more, Rb's may be the same or different from each other.
<20> A dye-sensitized solar cell, comprising the photoelectric conversion element described in any one of the above items <15> to <19>.

Advantageous Effects of Invention

According to the present invention, it is possible to provide a metal complex dye that is excellent in photoelectric conversion characteristics such as conversion efficiency, and durability with a small decrease in the photoelectric conversion characteristics even after use over a long period of time; a photoelectric conversion element prepared by using the same as a sensitizing dye; and a dye-sensitized solar cell composed of such a photoelectric conversion element.

Other and further features and advantages of the invention will appear more fully from the following description, appropriately referring to the accompanying drawing.

BRIEF DESCRIPTION OF THE DRAWING

FIG. 1 is a cross-sectional view schematically showing an exemplary embodiment of the photoelectric conversion element according to the present invention.

MODE FOR CARRYING OUT THE INVENTION

The present inventors have diligently repeated examinations. As a result, they have found that a metal complex dye (hereinafter, also simply referred to as a dye) having a specific bipyridine ligand containing a specific substituent is excellent in durability and photoelectric conversion characteristics, and a dye-sensitized solar cell produced by using a photoelectric conversion element containing semiconductor fine particles prepared by using the same as a sensitizing dye satisfies an excellent conversion efficiency and durability. The present invention is achieved based on the finding.

As shown in FIG. 1, a photoelectric conversion element 10 contains an electrically conductive support 1; and a photoconductor layer 2 (also referred to as "semiconductor film" or "semiconductor layer"), a charge transfer object layer 3 and a counter electrode 4, all provided on the electrically conductive support 1 in this order. The electrically conductive support 1 and the photoconductor layer 2 constitute a light-receiving electrode 5. The photoconductor layer 2 has semiconductor fine particles 22 and a sensitizing dye (hereinafter, also simply referred to as "dye") 21. The sensitizing dye 21 is at least partially adsorbed on the semiconductor fine particles 22 (the sensitizing dye 21 is in an adsorption equilibrium state, and may partially exist in the charge transfer object layer 3). The charge transfer object layer 3 may function, for example, as a hole-transporting layer for transporting positive holes (holes). The electrically conductive support 1 on which the photoconductor layer 2 is formed functions as a working electrode in the photoelectric conversion element 10. This photoelectric conversion element 10 is allowed to work in an external circuit 6, and can be operated as a photoelectrochemical cell 100.

A light-receiving electrode 5 is an electrode comprising an electrically conductive support 1; and a photosensitive layer 2 coated on the electrically conductive support 1, the layer containing semiconductor fine particles 22 to which a sensitizing dye 21 has been adsorbed. A light incident to the photosensitive layer 2 excites the dye. The excited dye has electrons with high energy, and these electrons are transported from the sensitizing dye 21 to the conduction band of the semiconductor fine particles 22 and further reach the electrically conductive support 1 by diffusion. At this time, the molecules of the sensitizing dye 21 are in an oxide form; however, in a photoelectrochemical cell 100, the electrons on the electrode return to the oxide of the dye while working in the external circuit 6, while the light-receiving electrode 5 works as a negative electrode of this cell.

The photoconductor layer 2 comprises a porous semiconductor layer constituted of a layer of the semiconductor fine particles 22 on which the dye described later is adsorbed. This dye may be partially dissociated in an electrolyte. The photoconductor layer 2 is designed for any purpose, and may form a multilayer structure.

As described above, the photoconductor layer 2 contains the semiconductor fine particles 22 on which a specific dye is adsorbed, and thus has a high light-receiving sensitivity. When it is used for the photoelectrochemical cell 100, a high photoelectric conversion efficiency and higher durability can be obtained.

(A) Metal Complex Dye

The photoelectric conversion element of the present invention contains semiconductor fine particles sensitized with the metal complex dye having the structure represented by Formula (I). Furthermore, the dye-sensitized solar cell of the present invention contains this photoelectric conversion element.

LL1

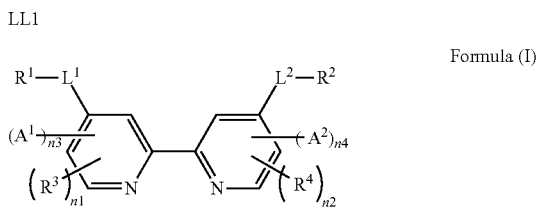

Formula (I)

In Formula (I), $R^1$ and $R^2$ each independently represent a group represented by any of Formulas (II) to (VIII). Although $R^1$ and $R^2$ may be the same or different from each other, $R^1$ and $R^2$ are preferably the same with each other. $R^1$ and $R^2$ each are preferably a group represented by Formula (II), a group represented by Formula (VII) or a group represented by Formula (VIII); further preferably a group represented by Formula (II) or a group represented by Formula (VIII); and particularly preferably a group represented by Formula (II).

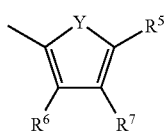
Formula (II)

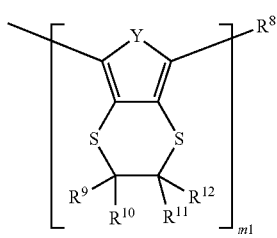
Formula (III)

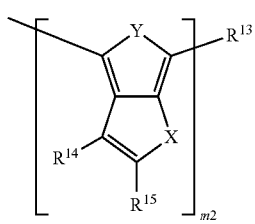
Formula (IV)

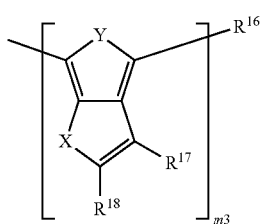
Formula (V)

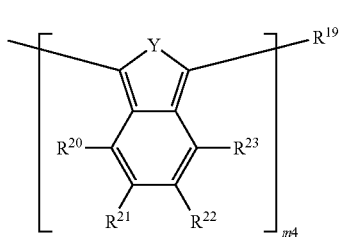
Formula (VI)

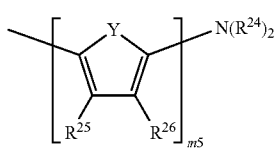
Formula (VII)

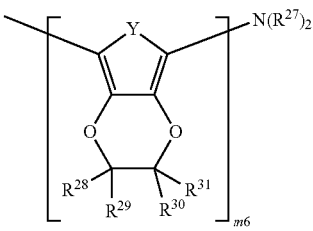
Formula (VIII)

In Formula (I), $L^1$ and $L^2$ each independently represent a group composed of at least one kind of group selected from the group consisting of an ethenylene group, an ethynylene group and an arylene group. $L^1$ and $L^2$ conjugate with $R^1$ or $R^2$, and the bipyridine. Herein, the ethenylene group and the arylene group may be substituted or unsubstituted.

From a viewpoint of suppressing a decrease in conversion efficiency due to an undesirable intermolecular association, L1 and L2 each are preferably a conjugated chain composed of an ethenylene group and/or an ethynylene group. The ethenylene group may be unsubstituted or substituted. L1 and L2 each are particularly preferably a conjugated chain composed of an ethenylene group, and the ethenylene group may be unsubstituted or substituted. L1 and L2 each are most preferably a conjugated chain composed of unsubstituted ethenylene. When L1 and L2 each are such a conjugated chain, an effect of expansion of an optical absorption region can be obtained by wavelength elongation and an increase in a molar absorption coefficient can be achieved.

The substituted ethenylene group is preferably methylethenylene, dimethylethenylene, methoxyethenylene, phenylethenylene, 4-methoxyphenylethenylene or trifluoromethylethenylene; further preferably methylethenylene, phenylethenylene or methoxyethenylene; and particularly preferably methylethenylene.

The substituted or unsubstituted arylene group is an arylene group having preferably 6 to 50 core atoms, further preferably 6 to 30 core atoms, particularly preferably 6 to 18 core atoms, and most preferably 6 to 12 core atoms. In addition, when the conjugated chain includes a carbon-carbon double bond, each double bond may form an E isomer or a Z isomer, or a mixture of the E isomer and the Z isomer. In the present invention, the number of core atoms means the number of atoms other than a hydrogen atom.

The conjugated chain including an unsubstituted ethenylene group is preferably ethenylene or butadienylene; further preferably ethenylene.

Specific examples of L1 and L2 are shown in the followings, but the present invention is not limited thereto.

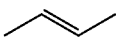
L-1

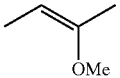
L-2

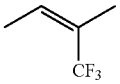
L-3

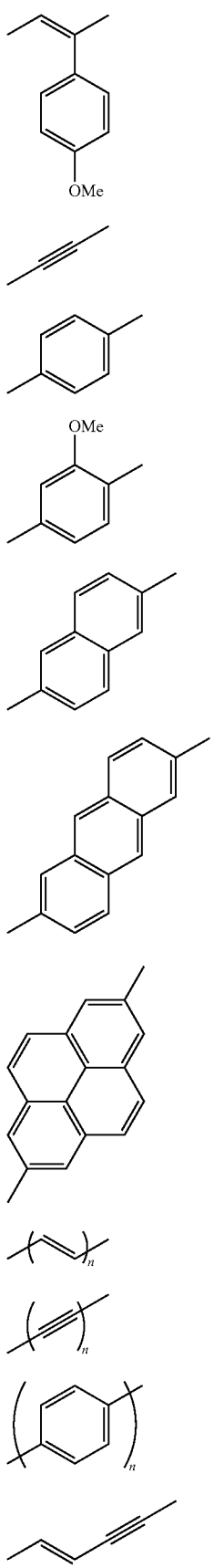
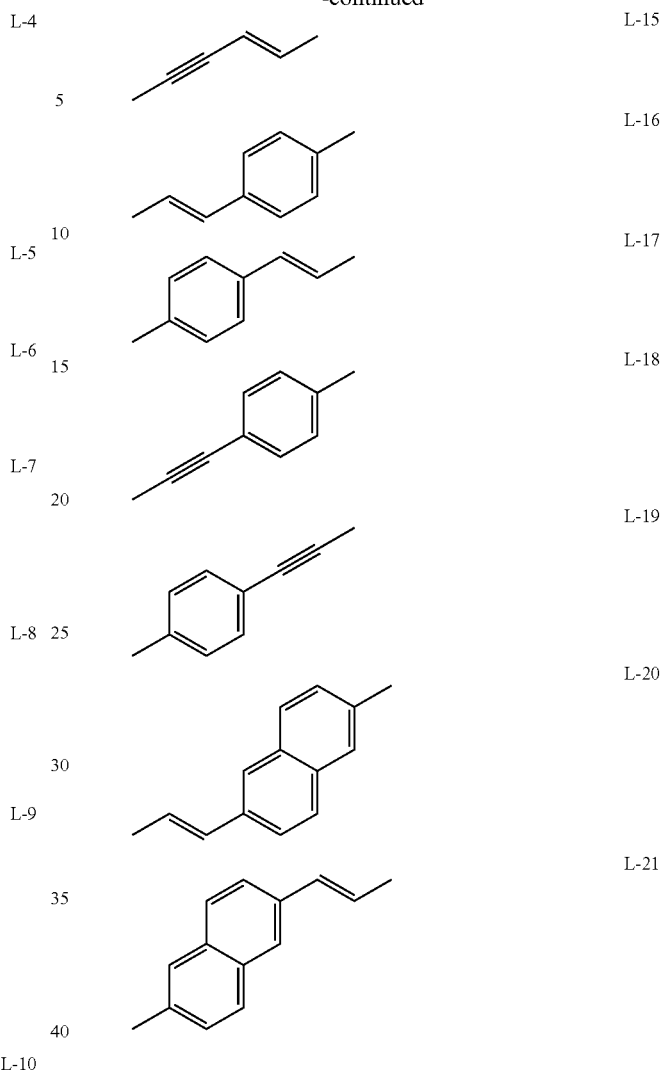

In L-11 to L-13, n represents an integer of 1 to 5, and Me represents a methyl group.

In Formula (I), $R^3$ and $R^4$ each independently represent a substituent, and examples thereof include the substituent W described below. The substituent is preferably an alkyl group, an aryl group, a heterocyclic group, an alkoxy group or an aryloxy group; further preferably an alkyl group, an alkoxy group, an aryl group or an aryloxy group; and particularly preferably an alkyl group or an aryl group.

[Substituent W]

The above-described substituent (hereinafter, referred to as substituent W) include, for example, an alkyl group [which represents a substituted or unsubstituted linear, branched, or cyclic alkyl group, and which includes an alkyl group (preferably an alkyl group having 1 to 30 carbon atoms, e.g. methyl, ethyl, n-propyl, isopropyl, t-butyl, n-octyl, eicosyl, 2-chloroethyl, 2-cyanoethyl, or 2-ethylhexyl), a cycloalkyl group (preferably a substituted or unsubstituted cycloalkyl group having 3 to 30 carbon atoms, e.g. cyclohexyl, cyclopentyl, or 4-n-dodecylcyclohexyl), a bicycloalkyl group (preferably a substituted or unsubstituted bicycloalkyl group having 5 to 30 carbon atoms, i.e. a monovalent group obtained by removing one hydrogen atom from a bicycloalkane having 5 to 30 carbon atoms, e.g. bicyclo[1.2.2]heptan-2-yl or bicyclo[2.2.2]octan-3-yl), and a tricyclo or higher structure having three or more ring structures; and an alkyl group in substituents described below (e.g. an alkyl group in an alkylthio group) represents such an alkyl group of the above concept]; an alkenyl group [which represents a substituted or unsubstituted linear, branched, or cyclic alkenyl group, and which includes an alkenyl group (preferably a substituted or unsubstituted alkenyl group having 2 to 30 carbon atoms, e.g. vinyl, allyl, prenyl, geranyl, or oleyl), a cycloalkenyl group (preferably a substituted or unsubstituted cycloalkenyl group having 3 to 30 carbon atoms, i.e. a monovalent group obtained by removing one hydrogen atom from a cycloalkene having 3 to 30 carbon atoms, e.g. 2-cyclopenten-1-yl or 2-cyclohexen-1-yl), and a bicycloalkenyl group (which represents a substituted or unsubstituted bicycloalkenyl group, preferably a substituted or unsubstituted bicycloalkenyl group having 5 to 30 carbon atoms, i.e. a monovalent group obtained by removing one hydrogen atom from a bicycloalkene having one double bond, e.g. bicyclo[2.2.1]hept-2-en-1-yl or bicyclo[2.2.2]oct-2-en-4-yl)]; an alkynyl group (preferably a substituted or unsubstituted alkynyl group having 2 to 30 carbon atoms, e.g. ethynyl, propargyl, or trimethylsilylethynyl); an aryl group (preferably a substituted or unsubstituted aryl group having 6 to 30 carbon atoms, e.g. phenyl, 4-methoxyphenyl, p-tolyl, naphthyl, m-chlorophenyl, or o-hexadecanoylaminophenyl); a heterocyclic group (preferably a monovalent group obtained by removing one hydrogen atom from a substituted or unsubstituted 5- or 6-membered aromatic or nonaromatic heterocyclic compound; more preferably a 5- or 6-membered aromatic heterocyclic group having 3 to 30 carbon atoms, e.g. 2-furyl, 2-thienyl, 2-pyrimidinyl, 2-benzothiazolyl); a silyl group (preferably a substituted or unsubstituted silyl group having 3 to 30 carbon atoms, e.g. trimethylsilyl, t-butyldimethylsilyl, or phenyldimethylsilyl); a hydroxyl group; an alkoxy group (preferably a substituted or unsubstituted alkoxy group having 1 to 30 carbon atoms, e.g. methoxy, ethoxy, isopropoxy, t-butoxy, n-octyloxy, 2-methoxyethoxy or 2-ethylhexyloxy); an aryloxy group (preferably a substituted or unsubstituted aryloxy group having 6 to 30 carbon atoms, e.g. phenoxy, 2-methylphenoxy, 4-t-butylphenoxy, 3-nitrophenoxy, 4-hexylphenoxy, or 2-tetradecanoylaminophenoxy); a heterocyclic oxy group (preferably a substituted or unsubstituted heterocyclic oxy group having 2 to 30 carbon atoms, e.g. 1-phenyltetrazol-5-oxy or 2-tetrahydropyranyloxy); a silyloxy group (preferably a silyloxy group having 3 to 20 carbon atoms, e.g. trimethylsilyloxy or t-butyldimethylsilyloxy); an acyloxy group (preferably a formyloxy group, a substituted or unsubstituted alkylcarbonyloxy group having 2 to 30 carbon atoms, or a substituted or unsubstituted arylcarbonyloxy group having 6 to 30 carbon atoms, e.g. formyloxy, acetyloxy, pivaloyloxy, stearoyloxy, benzoyloxy, or p-methoxyphenylcarbonyloxy); a carbamoyloxy group (preferably a substituted or unsubstituted carbamoyloxy group having 1 to 30 carbon atoms, e.g. N,N-dimethylcarbamoyloxy, N,N-diethylcarbamoyloxy, morpholinocarbonyloxy, N,N-di-n-octylaminocarbonyloxy, or N-n-octylcarbamoyloxy);
an alkoxycarbonyloxy group (preferably a substituted or unsubstituted alkoxycarbonyloxy group having 2 to 30 carbon atoms, e.g. methoxycarbonyloxy, ethoxycarbonyloxy, t-butoxycarbonyloxy, or n-octylcarbonyloxy); an aryloxycarbonyloxy group (preferably a substituted or unsubstituted aryloxycarbonyloxy group having 7 to 30 carbon atoms, e.g. phenoxycarbonyloxy, p-methoxyphenoxycarbonyloxy, or p-n-hexadecyloxyphenoxycarbonyloxy); an amino group (preferably an amino group, a substituted or unsubstituted alkylamino group having 1 to 30 carbon atoms, or a substituted or unsubstituted anilino group having 6 to 30 carbon atoms, e.g. amino, methylamino, dimethylamino, anilino, N-methyl-anilino, or diphenylamino); an acylamino group (preferably a formylamino group, a substituted or unsubstituted alkylcarbonylamino group having 1 to 30 carbon atoms, or a substituted or unsubstituted arylcarbonylamino group having 6 to 30 carbon atoms, e.g. formylamino, acetylamino, pivaloylamino, lauroylamino, benzoylamino, or 3,4,5-tri-n-octyloxyphenylcarbonylamino); an aminocarbonylamino group (preferably a substituted or unsubstituted aminocarbonylamino group having 1 to 30 carbon atoms, e.g. carbamoylamino, N,N-dimethylaminocarbonylamino, N,N-diethylaminocarbonylamino, or morpholinocarbonylamino); an alkoxycarbonylamino group (preferably a substituted or unsubstituted alkoxycarbonylamino group having 2 to 30 carbon atoms, e.g. methoxycarbonylamino, ethoxycarbonylamino, t-butoxycarbonylamino, n-octadecyloxycarbonylamino, or N-methyl-methoxycarbonylamino); an aryloxycarbonylamino group (preferably a substituted or unsubstituted aryloxycarbonylamino group having 7 to 30 carbon atoms, e.g. phenoxycarbonylamino, p-chlorophenoxycarbonylamino, or m-n-octyloxyphenoxycarbonylamino);
an imido group (preferably N-succinimido or N-phthalimido); an aryl- or heterocyclic-azo group (preferably a substituted or unsubstituted aryl azo group having 6 to 30 carbon atoms, or a substituted or unsubstituted heterocyclic azo group having 3 to 30 carbon atoms, e.g. phenylazo, p-chlorophenylazo, or 5-ethylthio-1,3,4-thiadiazol-2-ylazo); a mercapto group; an alkylthio group (preferably a substituted or unsubstituted alkylthio group having 1 to 30 carbon atoms, e.g. methylthio, ethylthio, or n-hexadecylthio); an arylthio group (preferably a substituted or unsubstituted arylthio group having 6 to 30 carbon atoms, e.g. phenylthio, p-chlorophenylthio, or m-methoxyphenylthio); a heterocyclic thio group (preferably a substituted or unsubstituted heterocyclic thio group having 2 to 30 carbon atoms, e.g. 2-benzothiazolylthio or 1-phenyltetrazol-5-ylthio); a sulfo group; an alkyl- or aryl-sulfonyl group (preferably a substituted or unsubstituted alkylsulfonyl group having 1 to 30 carbon atoms, or a substituted or unsubstituted arylsulfonyl group having 6 to 30 carbon atoms, e.g. a methylsulfonyl group, an ethylsulfonyl group, a phenylsulfonyl group, or a p-methylphenylsulfonyl group); a sulfamoyl group (preferably a substituted or unsubstituted sulfamoyl group having 0 to 30 carbon atoms, e.g. N-ethylsulfamoyl, N-(3-dodecyloxypropyl)sulfamoyl, N,N-dimethylsulfamoyl, N-acetylsulfamoyl, N-benzoylsulfamoyl, or N—(N'-phenylcarbamoyl)sulfamoyl); a sulfamoylamino group (preferably a substituted or unsubstituted sulfamoylamino group having 0 to 30 carbon atoms, e.g. sulfamoylamino, N,N-dimethylaminosulfonylamino, or N-n-octylaminosulfonylamino); a sulfino group;
an alkyl- or aryl-sulfinyl group (preferably a substituted or unsubstituted alkylsulfinyl group having 1 to 30 carbon atoms, or a substituted or unsubstituted arylsulfinyl group having 6 to 30 carbon atoms, e.g. methylsulfinyl, ethylsulfinyl, phenylsulfinyl, or p-methylphenylsulfinyl); an alkyl- or aryl-sulfonylamino group (preferably a substituted or unsubstituted alkylsulfonylamino group having 1 to 30 carbon atoms, or a substituted or unsubstituted arylsulfonylamino group having 6 to 30 carbon atoms, e.g. methylsulfonylamino, butylsulfonylamino, phenylsulfonylamino, 2,3,5-trichlorophenylsulfonylamino, or p-methylphenylsulfonylamino); an acyl group (preferably a formyl group, a substituted or unsubstituted alkylcarbonyl group having 2 to 30 carbon atoms, a substituted or unsubstituted arylcarbonyl group having 7 to 30 carbon atoms, or a substituted or unsubstituted heterocyclic carbonyl group having 4 to 30 carbon atoms, which is bonded to said carbonyl group through a carbon atom, e.g. an acetyl group, a pivaloyl group, a 2-chloroacetyl group, a stearoyl group, a benzoyl group, a p-n-octyloxyphenylcarbonyl group, a 2-pyridylcarbonyl group, or a 2-furylcarbonyl group); a carboxyl group; an aryloxycarbonyl group (preferably a substituted or unsubstituted aryloxycarbonyl group having 7 to 30 carbon atoms, e.g. phenoxycarbonyl, o-chlorophenoxycarbonyl, m-nitrophenoxycarbonyl, or p-t-butylphenoxycarbonyl); an alkoxycarbonyl group (preferably a substituted or unsubstituted alkoxycarbonyl group having 2 to 30 carbon atoms, e.g. methoxycarbonyl, ethoxycarbonyl, t-butoxycarbonyl, or n-octadecyloxycarbonyl); a carbamoyl group (preferably a substituted or unsubstituted carbamoyl group having 1 to 30 carbon atoms, e.g. carbamoyl, N-methylcarbamoyl, N,N-dimethylcarbamoyl, N,N-di-n-octylcarbamoyl, or N-(methylsulfonyl)carbamoyl);
a phosphino group (preferably a substituted or unsubstituted phosphino group having 2 to 30 carbon atoms, e.g. dimethylphosphino, diphenylphosphino, or methylphenoxyphosphino); a phosphinyl group (preferably a substituted or unsubstituted phosphinyl group having 2 to 30 carbon atoms, e.g. phosphinyl, dioctyloxyphosphinyl, or diethoxyphosphinyl); a phosphinyloxy group (preferably a substituted or unsubstituted phosphinyloxy group having 2 to 30 carbon atoms, e.g. diphenoxyphosphinyloxy or dioctyloxyphosphinyloxy); a phosphinylamino group (preferably a substituted or unsubstituted phosphinylamino group having 2 to 30 carbon atoms, e.g. dimethoxyphosphinylamino or dimethylaminophosphinylamino); a phospho group; a phosphonyl group (preferably a substituted or unsubstituted phosphonyl group having from 2 to 30 carbon atoms, e.g., phosphonyl, octyloxyphosphinyl, methoxyphosphonyl, ethoxyphosphinyl); a phosphonyloxy group (preferably a substituted or unsubstituted phosphonyloxy group having from 2 to 30 carbon atoms, e.g., phenoxyphosphonyloxy, octyloxyphosphonyloxy, or ethoxyphosphonyloxy); a phosphonylamino group (preferably a substituted or unsubstituted phosphonylamino group having 2 to 30 carbon atoms, e.g., methoxyphosphonylamino, or dimethylaminophosphonylamino);
a cyano group; a nitro group; and a halogen atom (e.g. a fluorine atom, a chlorine atom, a bromine atom, or an iodine atom).

The substituent may be further substituted. In that case, examples of the substituent include the substituent W mentioned above.

In Formula (I), n1 and n2 each independently represent an integer of 0 to 3. When n1 is an integer of 1 or more, $R^3$ may be bonded with $L^1$ to form a ring. When n2 is an integer of 1 or more, $R^4$ may be bonded with $L^2$ to form a ring. When n1 is an integer of 2 or more, $R^3$'s may be the same or different from each other, or $R^3$'s may be bonded to each other to form a ring. When n2 is an integer of 2 or more, $R^4$'s may be the same or different from each other, or $R^4$'s may be bonded to each other to form a ring. When n1 and n2 each are an integer of 1 or more, $R^3$ and $R^4$ may be bonded to each other to form a ring. Preferred examples of these rings to be formed include a benzene ring, a pyridine ring, a thiophene ring, a pyrrole ring, a furan ring, a cyclohexane ring, and a cyclopentane ring.

In Formula (I), n3 and n4 each independently represent an integer of 0 to 3. When n3 is an integer of 2 or more, $A^1$'s may be the same or different from each other. When n4 is an integer of 2 or more, $A^2$'s may be the same or different from each other. n3 and n4 each are preferably an integer of 0 to 2, further preferably 0 or 1. A sum of n3 and n4 is preferably an integer of 0 to 2.

In Formula (I), $A^1$ and $A^2$ each independently represents an acidic group or a salt thereof. In the present invention, the term "acidic group" means a group in which the pKa value of the most acidic hydrogen atom among the hydrogen atoms constituting the acidic group is 13 or less. Examples of the acidic group include a carboxylic acid group (a carboxyl group), a sulfonic acid group, a phosphonic acid group, a phenolic hydroxyl group, an alkylsulfonylamino group, a phosphoric acid group, a squaric acid group, a silicic acid group and a boric acid group. Preferred examples include a carboxylic acid group, a sulfonic acid group, a phosphonic acid group and a phenolic hydroxyl group; more preferred examples include a carboxylic acid group and a sulfonic acid group; and particularly preferred examples include a carboxylic acid group.

A counter ion of the above-described acidic group is preferably a proton, an inorganic or organic ammonium ion, or an alkaline metal ion. As the alkaline metal, a sodium ion, potassium ion or lithium ion is preferable; a sodium ion or potassium ion further preferable; and a sodium ion is particularly preferable. Examples of the inorganic or organic ammonium ion include an ammonium ion and a pyridinium ion. As the inorganic or organic ammonium ion, an ammonium ion, and a tertiary or quaternary alkylammonium ion are preferable; a tertiary or quaternary ammonium ion are further preferable; and a quaternary ammonium ion is particularly preferable. As the quaternary ammonium ion, a tetramethylammonium ion, a tetraethylammonium ion, a tetrabutylammonium ion, or a tetrahexylammonium ion is preferable; a tetrabutylammonium ion, or a tetrahexylammonium ion is further preferable; and a tetrabutylammonium ion is particularly preferable.

In Formulas (II) to (VI), $R^5$, $R^8$, $R^{13}$, $R^{16}$ and $R^{19}$ each independently represent an alkynyl group or an aryl group. $R^5$, $R^8$, $R^{13}$, $R^{16}$ and $R^{19}$ each are preferably an alkynyl group. The most rate-determining step in the dye-sensitized solar cell is ordinarily a reduction process of the dye from a redox system. The dye exists for a long period of time in an unstable one-electron oxidation state during the reduction, which leads to decomposition of the dye.

An effect of smooth progress of reduction from the redox system such as iodine can be achieved by presence of the alkynyl group and the aryl group. A triple bond part of the alkynyl group is linear, and a π-electron cloud is uniformly located 360 degrees around the part, and thus the alkynyl group can take effect of significantly facilitating interaction with the redox system (iodine or the like) in the electrolyte. The aryl group can also take effect by a broadened π-electron cloud in a similar manner, although the extent is not so remarkable as in the case of the alkynyl group.

The alkynyl group is an alkynyl group having preferably 2 to 30 carbon atoms, further preferably 4 to 25 carbon atoms, particularly preferably 5 to 18 carbon atoms, and most preferably 5 to 15 carbon atoms. The alkynyl group may be further substituted with the substituent W. The substituent is preferably an alkyl group, an alkynyl group, an alkoxy group, an aryl group, an aryloxy group or a heterocyclic group; further preferably an alkyl group, an aryl group or a heterocyclic group; and particularly preferably an alkyl group.

The aryl group is an aryl group having preferably 6 to 30 carbon atoms, further preferably 6 to 18 carbon atoms, and particularly preferably 6 to 12 carbon atoms. The aryl group may be further substituted with the substituent W. The substituent is preferably an alkyl group, an aryl group, an alkoxy group, an aryloxy group, a heterocyclic group, an alkylthio group, an arylthio group or an amino group; further preferably an alkyl group, an alkoxy group, an alkylthio group or an amino group; and particularly preferably an alkoxy group or an amino group.

In Formulas (II) to (VIII), $R^6$, $R^9$ to $R^{12}$, $R^{14}$, $R^{15}$, $R^{17}$, $R^{18}$, $R^{20}$ to $R^{23}$, $R^{25}$, $R^{26}$ and $R^{28}$ to $R^{31}$ each independently represent a hydrogen atom, an alkyl group, an alkenyl group, an alkynyl group, an alkoxy group, an alkylthio group, an aryl group, an aryloxy group, an arylthio group, an amino group, a heterocyclic group or a halogen atom; and at least one of $R^{25}$ and $R^{26}$ represents an alkyl group. As $R^{25}$ and $R^{26}$, a hydrogen atom, an alkyl group, an alkoxy group and an amino group are preferable; a hydrogen atom and an alkyl group are further preferable; and a hydrogen atom is particularly preferable. The alkyl group of the at least one of $R^{25}$ and $R^{26}$ is a branched or straight-chain alkyl group having preferably 1 to 12 carbon atoms, further preferably 3 to 10 carbon atoms, and particularly preferably 5 to 8 carbon atoms. Thus, such a structure can take effect of suppressing intermolecular association of the dye resulting in lowering the conversion efficiency, effect of suppressing approach of water to be a cause of desorption of the dye from an oxide semiconductor and effect of wavelength elongation by electron-donative properties of the alkyl group.

$R^6$ is preferably a hydrogen atom, an alkyl group, an alkynyl group or an alkoxy group; and further preferably a hydrogen atom or an alkyl group.

$R^9$ to $R^{12}$, $R^{20}$ to $R^{23}$ and $R^{28}$ to $R^{31}$ each are preferably a hydrogen atom or an alkyl group; and further preferably a hydrogen atom.

$R^{14}$ and $R^{17}$ each are preferably a hydrogen atom or an alkyl group; and further preferably a hydrogen atom.

$R^{15}$ and $R^{18}$ each are preferably a hydrogen atom, an alkyl group, an alkynyl group, an aryl group, an amino group, an alkoxy group or an alkylthio group; further preferably a hydrogen atom, an alkyl group or an alkynyl group; and particularly preferably an alkyl group or a hydrogen atom.

$R^7$ represents a hydrogen atom, an alkyl group, an alkenyl group, an alkynyl group, an alkylthio group or a halogen atom. $R^7$ is preferably a hydrogen atom, an alkyl group, an alkynyl group or an alkylthio group; and further preferably a hydrogen atom.

$R^7$ is a group adjacent to $R^5$ mentioned above, and is preferably sterically smaller in order to achieve the effect mentioned above. $R^7$ is not directly bonded with a group having a hard lone pair such as an oxygen atom (e.g. alkoxy group, aryloxy group and the like), in the 5-membered heterocycle in Formula (II). The reason is that reduction of the dye is not performed smoothly due to electron repulsion with the redox system. Herein, $R^7$ may be bonded with a group having a soft lone pair such as a sulfur atom.

Each of $R^6$ and $R^7$, any of $R^9$ to $R^{12}$, $R^{14}$ and $R^{15}$, $R^{17}$ and $R^{18}$, any of $R^{20}$ to $R^{23}$, $R^{25}$ and $R^{26}$, and any of $R^{28}$ to $R^{31}$ may be bonded with each other to form a ring. The ring formed by binding of each of $R^9$ to $R^{12}$, $R^{14}$ and $R^{15}$, $R^{17}$ and $R^{18}$, $R^{20}$ to $R^{23}$, $R^{25}$ and $R^{26}$, and $R^{28}$ to $R^{31}$ is preferably 5- to 10-membered ring, further preferably 5- to 8-membered ring, and particularly preferably 5- or 6-membered ring.

Examples of the 5-membered ring include a cyclopentane ring, a tetrahydrofuran ring, a 1,3-dioxolane ring, 1,3-oxathiolane, a pyrrole ring, a furan ring, a thiophene ring, an imidazole ring, an oxazole ring, a thiazole ring, a pyrazole ring, an isoxazole ring and an isothiazole ring. Among these, a cyclopentane ring, a 1,3-dioxolane ring, a tetrahydrofuran ring and a thiophene ring are preferable; a cyclopentane ring and a 1,3-dioxolane ring are further preferable; and a cyclopentane ring is particularly preferable.

Examples of the 6-membered ring include a cyclohexane ring, a benzene ring, a pyran ring, a dihydropyran ring, a dioxane ring, a pyridine ring, a pyrazine ring, a piperidine ring, a piperazine ring, and a morpholine ring. Among these, a cyclohexane ring, a benzene ring, a dihydropyran ring, a dioxane ring and a piperazine ring are preferable; a cyclohexane ring and a benzene ring are further preferable; and a cyclohexane ring is particularly preferable.

Among the groups that do not any ring, preferred examples include a hydrogen atom, an alkyl group, an alkoxy group and an aryl group; further preferred examples include a hydrogen atom, an alkyl group and an alkoxy group; and particularly preferred examples include a hydrogen atom.

In Formulas (VII) and (VIII), the two $R^{24}$'s and the two $R^{27}$'s present in the same characteristic group may be the same or different from each other, and $R^{24}$ and $R^{27}$ each represent a hydrogen atom, an alkyl group, an alkenyl group or an alkynyl group. However, $R^{24}$'s and $R^{27}$'s each are not bonded with each other for forming a ring. Presence of these hydrophobic groups is effective in suppressing approach of water present in a trace amount in the electrolyte to cause a decrease in durability due to desorption of the dye. An aromatic group such as a benzene ring causes an inefficient association of the dyes with each other by stacking of π-electrons and may cause a decrease in conversion efficiency. However, these aliphatic groups have a high degree of freedom to allow suppression of the inefficient association, and are effective in improving the conversion efficiency.

$R^{24}$ and $R^{27}$ each are preferably an alkyl group, an alkenyl group or an alkynyl group; further preferably an alkyl group or an alkynyl group; and particularly preferably an alkyl group.

The alkyl group is a branched or straight-chain alkyl group having preferably 1 to 15 carbon atoms, further preferably 3 to 12 carbon atoms, and particularly preferably 4 to 10 carbon atoms.

The alkenyl group and the alkynyl group have preferably 2 to 15 carbon atoms, further preferably 4 to 12 carbon atoms, and particularly preferably 6 to 10 carbon atoms.

In Formulas (II) to (VIII), m1 to m6 each independently represent an integer of 1 to 5.

Y represents S, O, Se, Te or $NR^{32}$; and $R^{32}$ represents a hydrogen atom, an alkyl group, an alkenyl group, an alkynyl group, an aryl group or a heterocyclic group.

X represents S, Se, Te or $NR^{32}$; and $R^{32}$ represents a hydrogen atom, an alkyl group, an alkenyl group, an alkynyl group, an aryl group or a heterocyclic group.

Y is preferably S, O or $NR^{32}$; further preferably S or O; and particularly preferably S. When Y is S, the thiophene ring to be formed has high electron-donative properties, and is effective in wavelength elongation, and is considered to have a high stability against nucleophilic species numerously present in the electrolyte.

X is preferably S, Se or $NR^{32}$; further preferably S or Se; and particularly preferably S. A choice of S for X is preferable from the reason similar to the case of Y, and from a viewpoint of improving reduction speed of the dye due to interaction of an orbital of a soft S atom with the redox system.

$R^{32}$ is preferably a hydrogen atom, an alkyl group, an aryl group or a heterocyclic group; further preferably a hydrogen atom or an alkyl group; and particularly preferably an alkyl group.

Specific examples of the ligand represented by Formula (I) are shown in the followings, but the present invention is not limited thereto. As these acidic groups, only a proton undissociator is shown, but these acidic group each may be a proton dissociator. When a carbon-carbon double bond is present in the structure, an E isomer or a Z isomer, or a mixture thereof may be used.

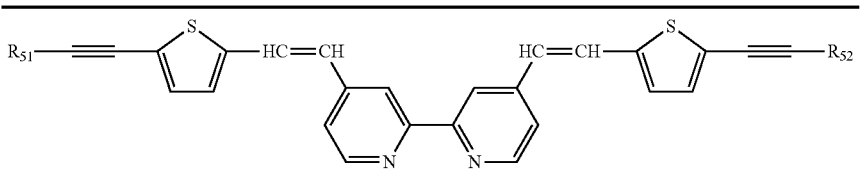

| | R51 | R52 |
|---|---|---|
| A-1-1 | —CH₃ | —CH₃ |
| A-1-2 | —nC₃H₇ | —nC₃H₇ |
| A-1-3 | —nC₅H₁₁ | —nC₅H₁₁ |
| A-1-4 | —nC₇H₁₅ | —nC₇H₁₅ |
| A-1-5 | —nC₁₀H₂₁ | —nC₁₀H₂₁ |
| A-1-6 | —nC₅H₁₁ | —nC₉H₁₉ |
| A-1-7 | —iC₅H₁₁ | —iC₅H₁₁ |
| A-1-8 | —iC₅H₁₁ | —nC₆H₁₃ |
| A-1-9 | —C₆H₄—nC₅H₁₁ | —C₆H₄—nC₅H₁₁ |
| A-1-10 | —C₆H₄—nC₁₀H₂₁ | —C₆H₄—nC₁₀H₂₁ |
| A-1-11 | —C₆H₄—OnC₇H₁₅ | —C₆H₄—OnC₇H₁₅ |
| A-1-12 | —C₆H₄—N(nC₆H₁₃)₂ | —C₆H₄—N(nC₆H₁₃)₂ |
| A-1-13 | —C₆H₃(N(nC₆H₁₃)₂)—N(nC₆H₁₃)₂ | —C₆H₃(N(nC₆H₁₃)₂)—N(nC₆H₁₃)₂ |
| A-1-14 | —(thienyl)—nC₅H₁₁ | —(thienyl)—nC₅H₁₁ |

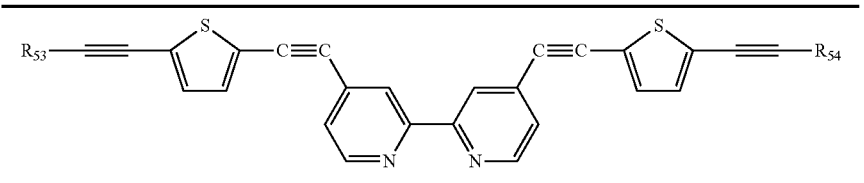

| | R53 | R54 |
|---|---|---|
| A-2-1 | —CH₃ | —CH₃ |
| A-2-2 | —nC₃H₇ | —nC₃H₇ |
| A-2-3 | —nC₅H₁₁ | —nC₅H₁₁ |
| A-2-4 | —nC₇H₁₅ | —nC₇H₁₅ |
| A-2-5 | —nC₁₀H₂₁ | —nC₁₀H₂₁ |
| A-2-6 | —nC₅H₁₁ | —nC₉H₁₉ |
| A-2-7 | —iC₅H₁₁ | —iC₅H₁₁ |
| A-2-8 | —iC₅H₁₁ | —nC₆H₁₃ |
| A-2-9 | —C₆H₄—nC₅H₁₁ | —C₆H₄—nC₅H₁₁ |
| A-2-10 | —C₆H₄—nC₁₀H₂₁ | —C₆H₄—nC₁₀H₂₁ |

-continued
| | | |
|---|---|---|
| A-2-11 | 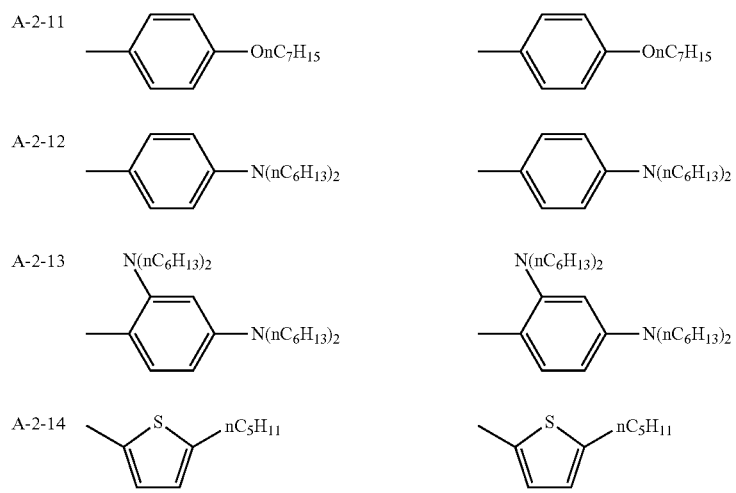 | |
| A-2-12 | | |
| A-2-13 | | |
| A-2-14 | | |
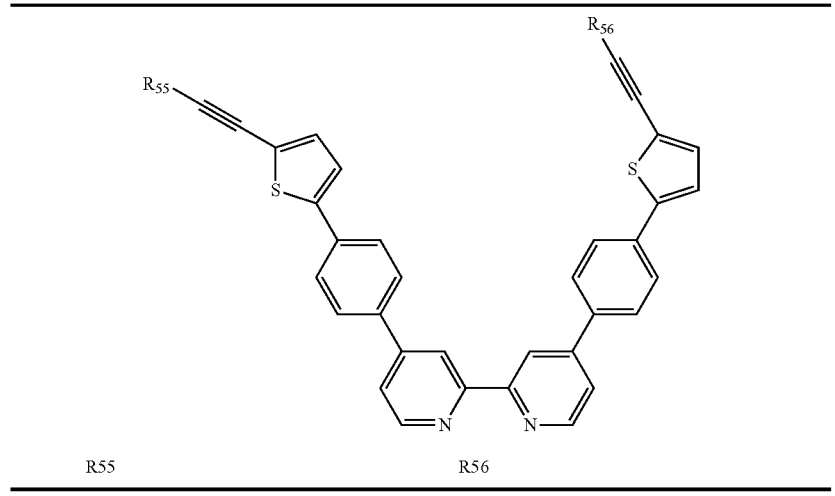
| | R55 | R56 |
|---|---|---|
| A-3-1 | —CH$_3$ | —CH$_3$ |
| A-3-2 | —nC$_3$H$_7$ | —nC$_3$H$_7$ |
| A-3-3 | —nC$_5$H$_{11}$ | —nC$_5$H$_{11}$ |
| A-3-4 | —nC$_7$H$_{15}$ | —nC$_7$H$_{15}$ |
| A-3-5 | —nC$_{10}$H$_{21}$ | —nC$_{10}$H$_{21}$ |
| A-3-6 | —nC$_5$H$_{11}$ | —nC$_9$H$_{19}$ |
| A-3-7 | —iC$_5$H$_{11}$ | —iC$_5$H$_{11}$ |
| A-3-8 | —iC$_5$H$_{11}$ | —nC$_6$H$_{13}$ |
| A-3-9 | 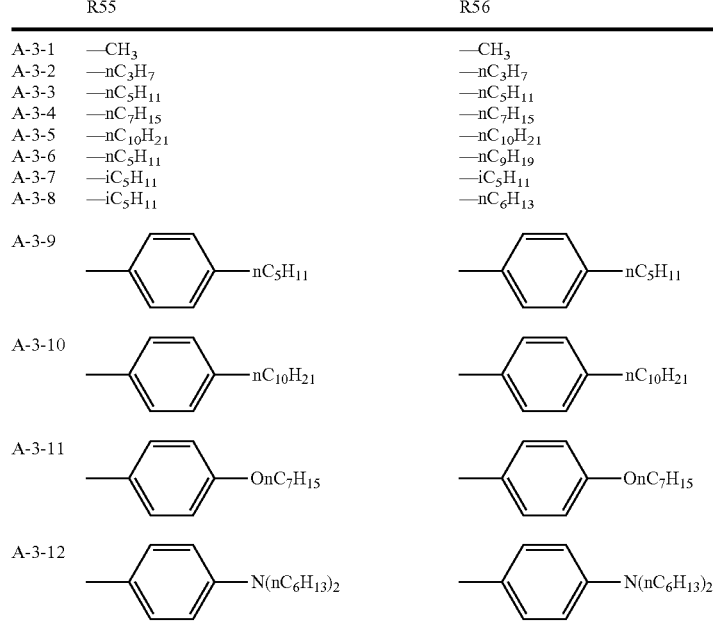 | |
| A-3-10 | | |
| A-3-11 | | |
| A-3-12 | | |

-continued
A-3-13 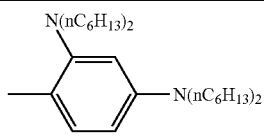 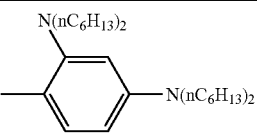
A-3-14 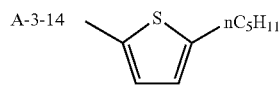 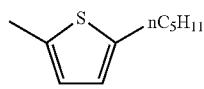
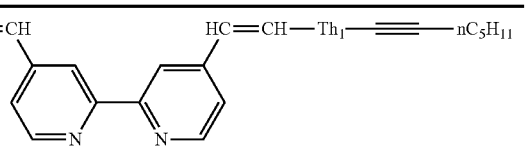
Th1
A-5-1 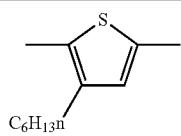
A-5-2 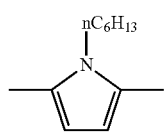
A-5-3 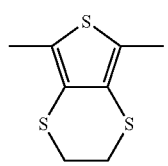
A-5-4 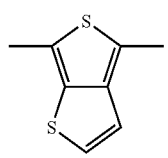
A-5-5 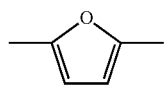
A-5-6 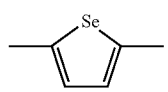
A-5-7 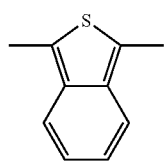
A-5-8 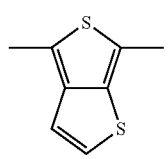

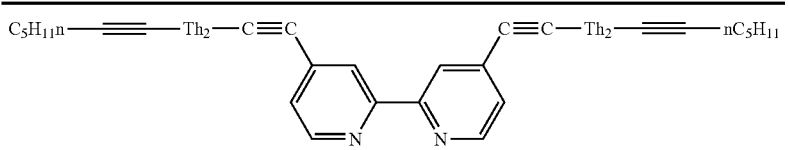
Th2
| | |
|---|---|
| A-6-1 | 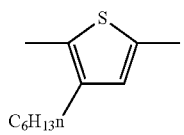 |
| A-6-2 | 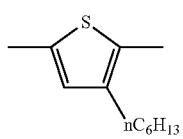 |
| A-6-3 | 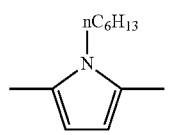 |
| A-6-4 | 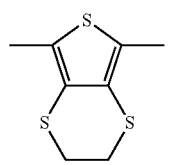 |
| A-6-5 | 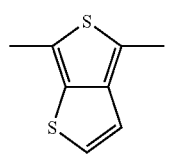 |
| A-6-6 | 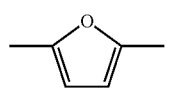 |
| A-6-7 | 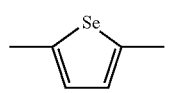 |
| A-6-8 | 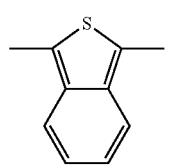 |
| A-6-9 | 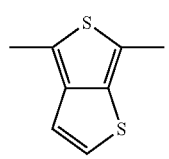 |

-continued
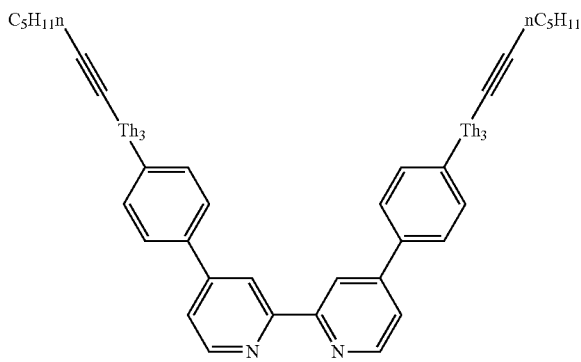
Th3
| A-7-1 | 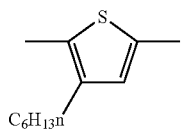 |
| A-7-2 | 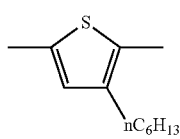 |
| A-7-3 | 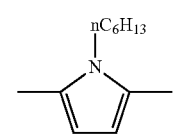 |
| A-7-4 | 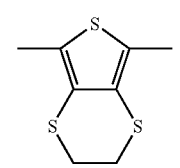 |
| A-7-5 | 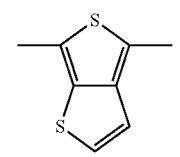 |
| A-7-6 | 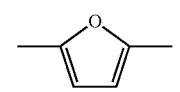 |
| A-7-7 | 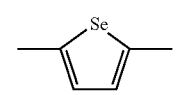 |
| A-7-8 | 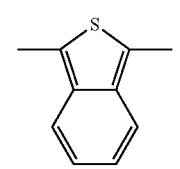 |

-continued
| | |
|---|---|
| A-7-9 | 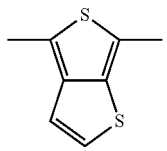 |
nC₆H₁₃—⌬—Th₄—HC=CH—[bipyridine]—HC=CH—Th₄—⌬—nC₆H₁₃
Th4
| | |
|---|---|
| A-8-1 | 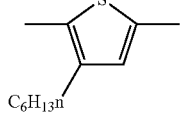 |
| A-8-2 | 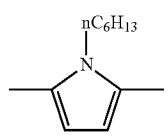 |
| A-8-3 | 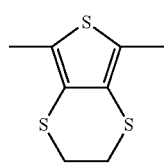 |
| A-8-4 | 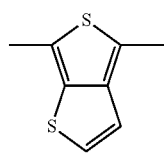 |
| A-8-5 | 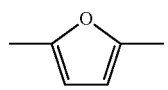 |
| A-8-6 | 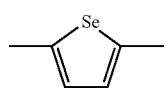 |
| A-8-7 | 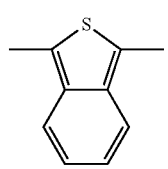 |
| A-8-8 | 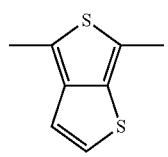 |

-continued
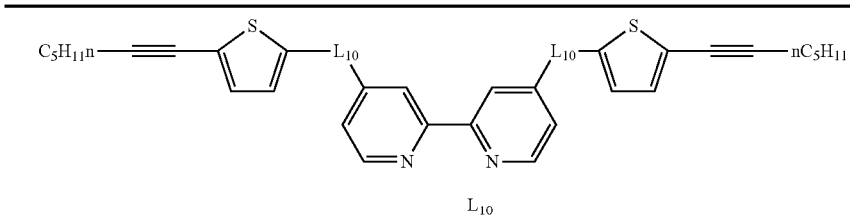
L₁₀
| A-9-1 | 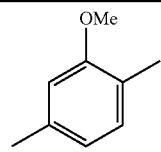 |
| --- | --- |
| A-9-2 | 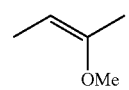 |
| A-9-3 | 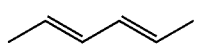 |
| A-9-4 | 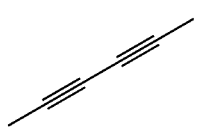 |
| A-9-5 | 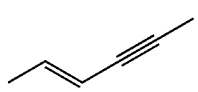 |
| A-9-6 | 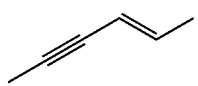 |
| A-9-7 | 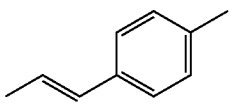 |
| A-9-8 | 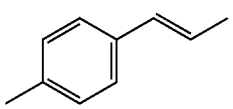 |
| A-9-9 | 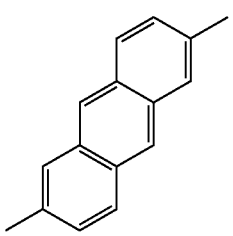 |
| A-9-10 | 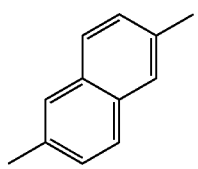 |
| A-9-11 | 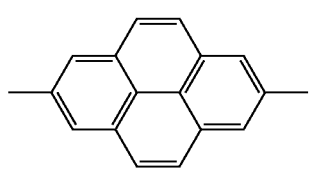 |

-continued

A-9-12 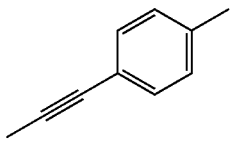

A-9-13 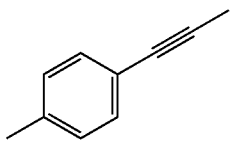

A-9-14 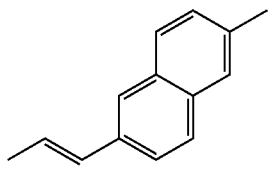

A-9-15 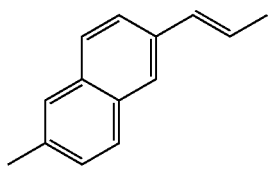

|  | $R_{57}$ | $R_{58}$ |
|---|---|---|
| A-10-1 | $N(CH_3)_2$ | $N(CH_3)_2$ |
| A-10-2 | $N(nC_6H_{13})_2$ | $N(nC_6H_{13})_2$ |
| A-10-3 | $N(nC_{10}H_{21})_2$ | $N(nC_{10}H_{21})_2$ |
| A-10-4 | $N(2\text{-ethylhexyl})_2$ | $N(2\text{-ethylhexyl})_2$ |
| A-10-5 | $N(CH_3)(C_6H_{13})$ | $N(CH_3)(C_6H_{13})$ |
| A-10-6 | $N(CH_3)(C_6H_{13})$ | $N(nC_6H_{13})_2$ |

|  | $R_{59}$ | $R_{60}$ |
|---|---|---|
| A-11-1 | $N(CH_3)_2$ | $N(CH_3)_2$ |
| A-11-2 | $N(nC_6H_{13})_2$ | $N(nC_6H_{13})_2$ |
| A-11-3 | $N(nC_{10}H_{21})_2$ | $N(nC_{10}H_{21})_2$ |
| A-11-4 | $N(2\text{-ethylhexyl})_2$ | $N(2\text{-ethylhexyl})_2$ |
| A-11-5 | $N(CH_3)(C_6H_{13})$ | $N(CH_3)(C_6H_{13})$ |
| A-11-6 | $N(CH_3)(C_6H_{13})$ | $N(nC_6H_{13})_2$ |

|  | $R_{61}$ | $R_{62}$ |
|---|---|---|
| A-12-1 | —$nC_5H_{11}$ | —$nC_5H_{11}$ |
| A-12-2 | —$nC_{10}H_{21}$ | —$nC_{10}H_{21}$ |
| A-12-3 | —$nC_5H_{11}$ | —$nC_9H_{19}$ |
| A-12-4 | —$iC_5H_{11}$ | —$iC_5H_{11}$ |
| A-12-5 | —$iC_5H_{11}$ | —$nC_6H_{13}$ |
| A-12-6 | —⟨C₆H₄⟩—$nC_5H_{11}$ | —⟨C₆H₄⟩—$nC_5H_{11}$ |

-continued
| | | |
|---|---|---|
| A-12-7 | 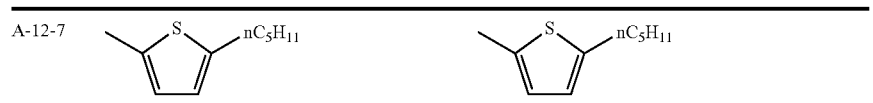 | |
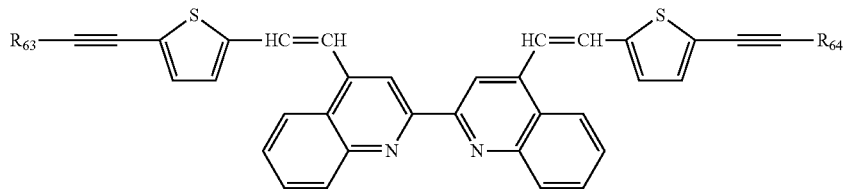
| | $R_{63}$ | $R_{64}$ |
|---|---|---|
| A-13-1 | —nC$_5$H$_{11}$ | —nC$_5$H$_{11}$ |
| A-13-2 | —nC$_{10}$H$_{21}$ | —nC$_{10}$H$_{21}$ |
| A-13-3 | —nC$_5$H$_{11}$ | —nC$_9$H$_{19}$ |
| A-13-4 | —iC$_5$H$_{11}$ | —iC$_5$H$_{11}$ |
| A-13-5 | —iC$_5$H$_{11}$ | —nC$_6$H$_{13}$ |
| A-13-6 | 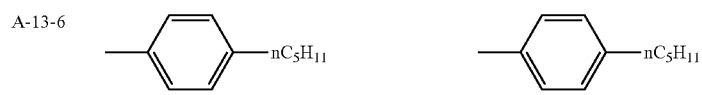 | |
| A-13-7 | 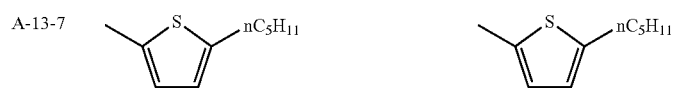 | |
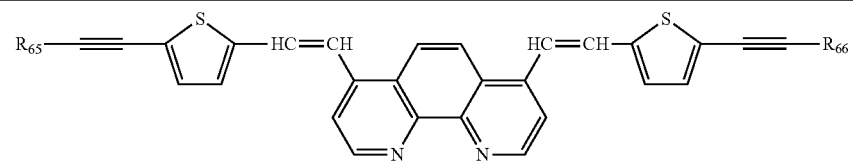
| | $R_{65}$ | $R_{66}$ |
|---|---|---|
| A-14-1 | —nC$_5$H$_{11}$ | —nC$_5$H$_{11}$ |
| A-14-2 | —nC$_{10}$H$_{21}$ | —nC$_{10}$H$_{21}$ |
| A-14-3 | —nC$_5$H$_{11}$ | —nC$_9$H$_{19}$ |
| A-14-4 | —iC$_5$H$_{11}$ | —iC$_5$H$_{11}$ |
| A-14-5 | —iC$_5$H$_{11}$ | —nC$_6$H$_{13}$ |
| A-14-6 |  | |
| A-14-7 |  | |
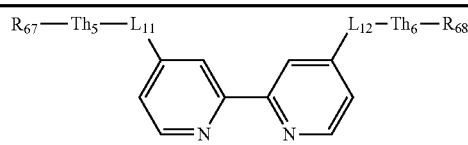
| | $R_{67}$ | $R_{68}$ | Th$_5$ | Th$_6$ | L$_{11}$ | L$_{12}$ |
|---|---|---|---|---|---|---|
| A-15-1 | 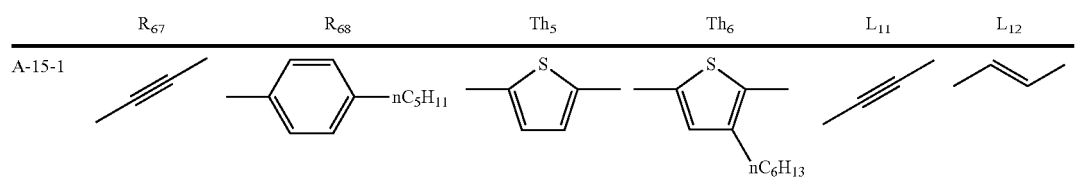 | | | | | |

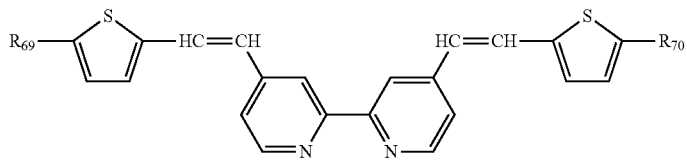
| | R₆₉ | R₇₀ |
|---|---|---|
| A-16-1 | 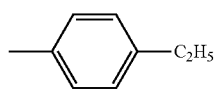 | 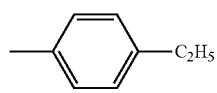 |
| A-16-2 | 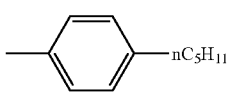 | 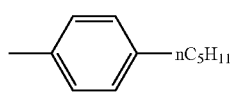 |
| A-16-3 | 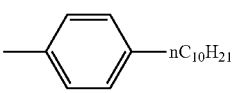 | 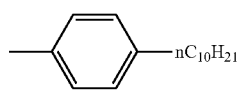 |
| A-16-4 | 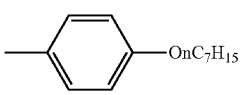 | 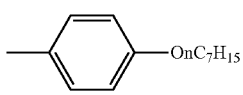 |
| A-16-5 | 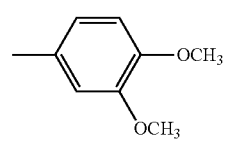 | 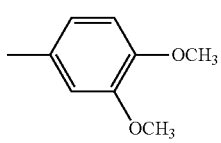 |
| A-16-6 | 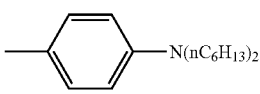 | 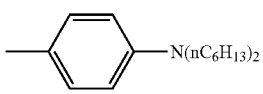 |
| A-16-7 | 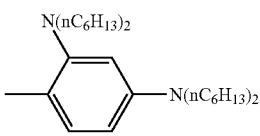 | 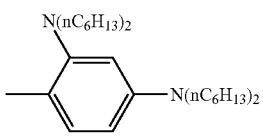 |
| A-16-8 | 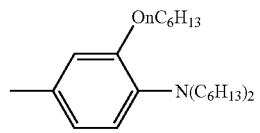 | 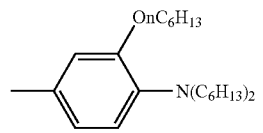 |
| A-16-9 | 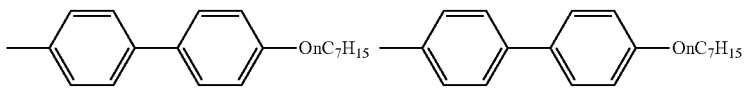 | |
| A-16-10 | 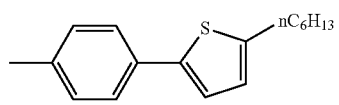 | 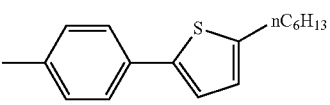 |

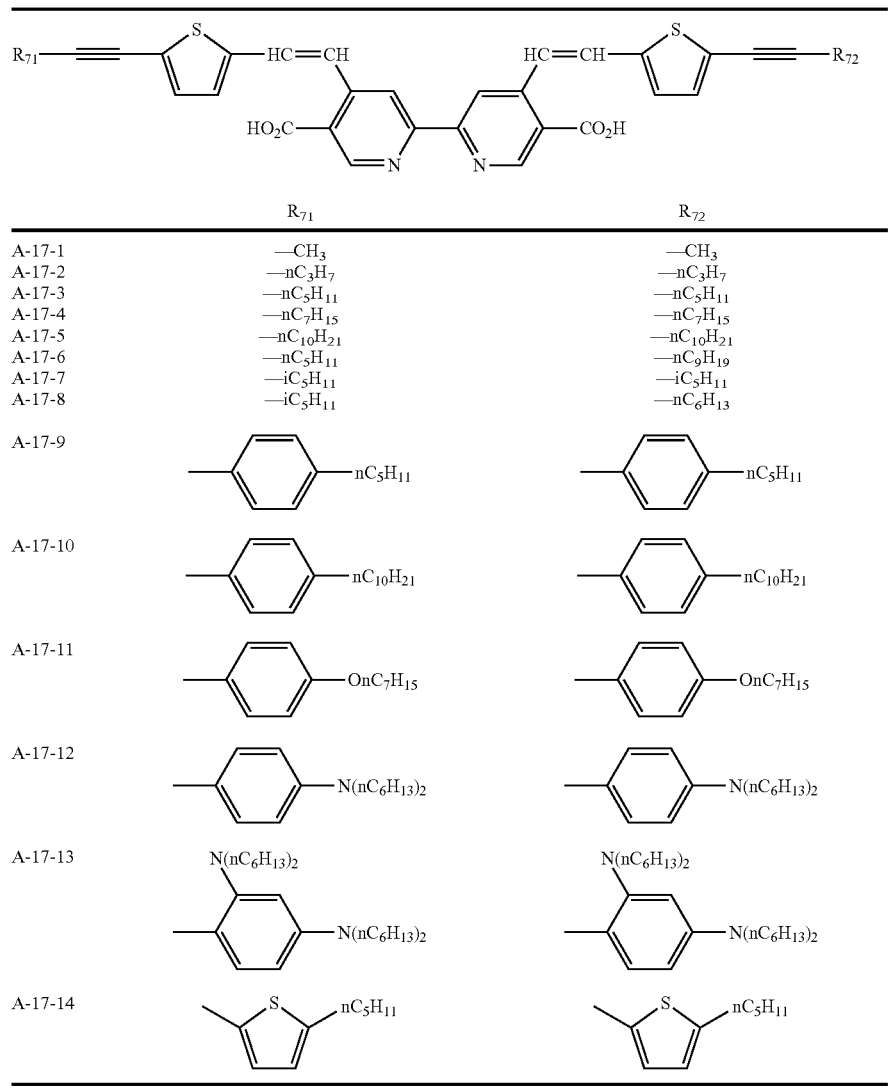

| | $R_{71}$ | $R_{72}$ |
|---|---|---|
| A-17-1 | —$CH_3$ | —$CH_3$ |
| A-17-2 | —$nC_3H_7$ | —$nC_3H_7$ |
| A-17-3 | —$nC_5H_{11}$ | —$nC_5H_{11}$ |
| A-17-4 | —$nC_7H_{15}$ | —$nC_7H_{15}$ |
| A-17-5 | —$nC_{10}H_{21}$ | —$nC_{10}H_{21}$ |
| A-17-6 | —$nC_5H_{11}$ | —$nC_9H_{19}$ |
| A-17-7 | —$iC_5H_{11}$ | —$iC_5H_{11}$ |
| A-17-8 | —$iC_5H_{11}$ | —$nC_6H_{13}$ |

The metal complex dye of the present invention is preferably represented by Formula (IX).

$$M(LL1)(LL2)(Z)_p \cdot Cl \quad \text{Formula (IX)}$$

In Formula (IX), M represents a metal atom. M is preferably a metal allowing four-coordination or 6-coordination (e.g., Ru, Re, Rh, Pt, Fe, Os, Cu, Ir, Pd, W, Co, Zn, Pb); further preferably Ru, Re, Rh, Pt, Fe, Os, Cu, Ir, Pd, W, or Co; particularly preferably Ru, Re, Rh, Os, Ir, or W; and most preferably Ru.

In Formula (IX), LL1 has the same meaning as LL1 in Formula (I), and the preferable range thereof is also the same. In Formula (IX), LL2 represents a ligand represented by Formula (X).

LL2

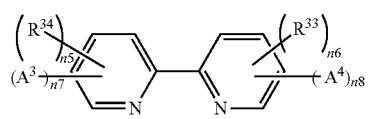

Formula (X)

In Formula (X), $R^{33}$ and $R^{34}$ each independently represent a substituent, and examples thereof include the substituent W described above. The substituent is preferably an alkyl group, an aryl group, a heterocyclic group, an alkoxy group, an aryloxy group or a halogen atom; further preferably an alkyl group, an alkoxy group, an aryl group or an aryloxy group; and particularly preferably an alkyl group or an aryl group.

In Formula (X), n5 and n6 each independently represent an integer of 0 to 3. When n5 is an integer of 2 or more, $R^{34}$'s may be the same or different from each other, or $R^{34}$'s may be bonded to each other to form a ring. When n6 is an integer of 2 or more, $R^{33}$'s may be the same or different from each other, or $R^{33}$'s may be bonded to each other to form a ring. When n5 and n6 each are an integer of 1 or more, $R^{33}$ and $R^{34}$ may be bonded to each other to form a ring. Preferred examples of these rings to be formed include a benzene ring, a pyridine ring, a thiophene ring, a pyrrole ring, a furan ring, a cyclohexane ring, and a cyclopentane ring.

In Formula (X), n7 and n8 each independently represent an integer of 1 to 4. When n7 is an integer of 2 or more, $A^3$'s may be the same or different from each other. When n8 is an integer of 2 or more, $A^4$'s may be the same or different from each other. n7 and n8 each are preferably an integer of 1 to 3, further preferably an integer of 1 or 2, and particularly preferably an integer of 1.

In Formula (X), $A^3$ and $A^4$ have the same meaning as $A^1$ and $A^2$ in Formula (I), and the preferable ranges thereof are also the same. The substitution site of $A^3$ and $A^4$ is preferably the m-position or p-position of the nitrogen atom of the pyridine ring, and further preferably the p-position.

Specific examples of LL2 are shown in the followings, but the present invention is not limited thereto. As these acidic groups, only a proton undissociator is shown, but these acidic groups each may be a proton dissociator. When a carbon-carbon double bond is present in the structure, an E isomer or a Z isomer, or a mixture thereof may be used.

Herein, Ph represents a phenyl group.

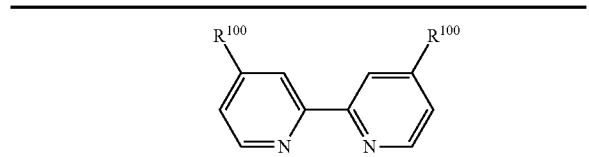

| | |
|---|---|
| B-1-1 | —$CO_2H$ |
| B-1-2 | —$SO_3H$ |
| B-1-3 | —$PO_3H_2$ |
| B-1-4 | —$OPO_3H_2$ |
| B-1-5 | —OH |
| B-1-6 | —$NHSO_2CH_3$ |

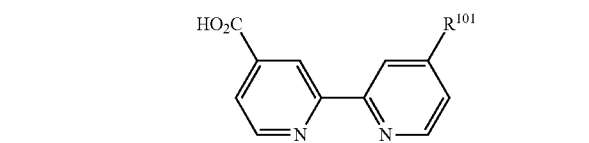

| | |
|---|---|
| B-2-1 | —$SO_3H$ |
| B-2-2 | —$PO_3H_2$ |
| B-2-3 | —$OPO_3H_2$ |
| B-2-4 | —OH |
| B-2-5 | —$NHSO_2CH_3$ |

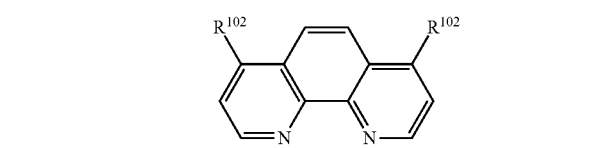

| | |
|---|---|
| B-3-1 | —$CO_2H$ |
| B-3-2 | —$SO_3H$ |
| B-3-3 | —$PO_3H_2$ |
| B-3-4 | —$OPO_3H_2$ |
| B-3-5 | —OH |
| B-3-6 | —$NHSO_2CH_3$ |

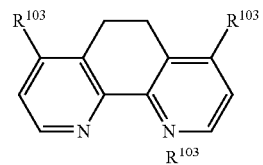

| | |
|---|---|
| B-4-1 | —$CO_2H$ |
| B-4-2 | —$SO_3H$ |
| B-4-3 | —$PO_3H_2$ |
| B-4-4 | —$OPO_3H_2$ |
| B-4-5 | —OH |
| B-4-6 | —$NHSO_2CH_3$ |

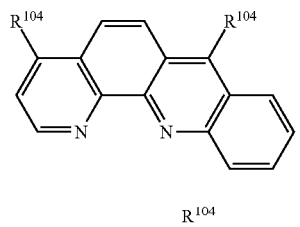

| | |
|---|---|
| B-5-1 | —$CO_2H$ |
| B-5-2 | —$SO_3H$ |
| B-5-3 | —$PO_3H_2$ |
| B-5-4 | —$OPO_3H_2$ |
| B-5-5 | —OH |
| B-5-6 | —$NHSO_2CH_3$ |

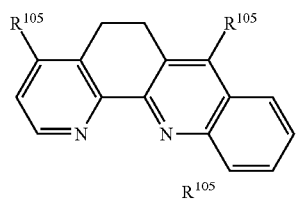

| | |
|---|---|
| B-6-1 | —$CO_2H$ |
| B-6-2 | —$SO_3H$ |
| B-6-3 | —$PO_3H_2$ |
| B-6-4 | —$OPO_3H_2$ |
| B-6-5 | —OH |
| B-6-6 | —$NHSO_2CH_3$ |

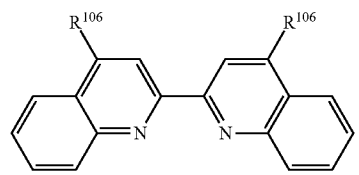

| | |
|---|---|
| B-7-1 | —$CO_2H$ |
| B-7-2 | —$SO_3H$ |
| B-7-3 | —$PO_3H_2$ |
| B-7-4 | —$OPO_3H_2$ |
| B-7-5 | —OH |
| B-7-6 | —$NHSO_2CH_3$ |

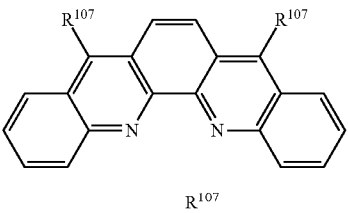

| | |
|---|---|
| B-8-1 | —CO₂H |
| B-8-2 | —SO₃H |
| B-8-3 | —PO₃H₂ |
| B-8-4 | —OPO₃H₂ |
| B-8-5 | —OH |
| B-8-6 | —NHSO₂CH₃ |

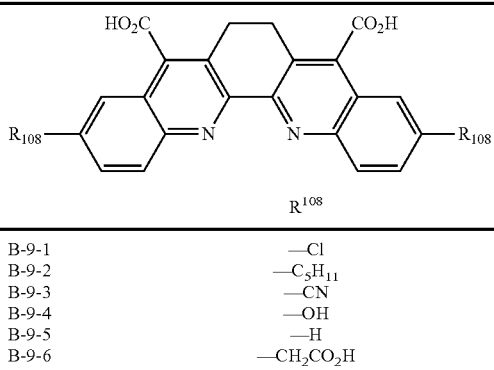

| | |
|---|---|
| B-9-1 | —Cl |
| B-9-2 | —C₅H₁₁ |
| B-9-3 | —CN |
| B-9-4 | —OH |
| B-9-5 | —H |
| B-9-6 | —CH₂CO₂H |

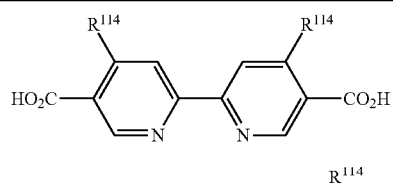

| | |
|---|---|
| B-10-1 | —Ph |
| B-10-2 | —C₅H₁₁ |
| B-10-3 | —CN |
| B-10-4 | —OH |
| B-10-5 | —H |
| B-10-6 | —Br |

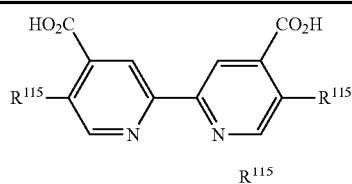

| | |
|---|---|
| B-11-1 | —Cl |
| B-11-2 | —Br |
| B-11-3 | —C₅H₁₁ |
| B-11-4 | —CN |
| B-11-5 | —OH |
| B-11-6 | —H |
| B-11-7 | —CH₂CO₂H |
| B-11-8 | —Ph |

In Formula (IX), Z represents a monodentate or bidentate ligand. Moreover, p represents an integer of 0 to 2. In the case where M in Formula (IX) is a metal that is likely to form four coordination, such as Cu, Pd, Pt, Zn or Pb, p is preferably 0. In the case where M in Formula (IX) is a metal that is likely to form six coordination, when Z is a monodentate ligand, p is preferably 2; and when Z is a bidentate ligand, p is preferably 1. When p is 2, Z's may be the same or different from each other.

The ligand Z represents a monodentate or bidentate ligand which coordinates through a coordinating group selected from the group consisting of an acyloxy group (preferably an acyloxy group having 1 to 20 carbon atoms, for example, an acetyloxy group, a benzoyloxy group, a salicylic acid group, a glycyloxy group, a N,N-dimethylglycyloxy group, an oxalylene group (—OC(O)C(O)O—), and the like), an acylthio group (preferably an acylthio group having 1 to 20 carbon atoms, for example, an acetylthio group, a benzoylthio group, and the like), a thioacyloxy group (preferably a thioacyloxy group having 1 to 20 carbon atoms, for example, a thioacetyloxy group (CH₃C(S)O—) and the like), a thioacylthio group (preferably a thioacylthio group having 1 to 20 carbon atoms, for example, a thioacetylthio group (CH₃C(S)S—), a thiobenzoylthio group (PhC(S)S—) and the like), an acylaminooxy group (preferably an acylaminooxy group having 1 to 20 carbon atoms, for example, a N-methylbenzoyl group aminooxy (PhC(O)N(CH₃)O—), an acetylaminooxy group (CH₃C(O)NHO—) and the like), a thiocarbamate group (preferably a thiocarbamate group having 1 to 20 carbon atoms, for example, a N,N-diethylthiocarbamate group and the like), a dithiocarbamate group (preferably a dithiocarbamate group having 1 to 20 carbon atoms, for example, a N-phenydithio carbamate group, a N,N-dimethyldithiocarbamate group, a N,N-diethyldithiocarbamate group, a N,N-dibenzyldithiocarbamate group and the like), a thiocarbonate group (preferably a thiocarbonate group having 1 to 20 carbon atoms, for example, an ethylthiocarbonate group and the like), a dithiocarbonate group (preferably a dithiocarbonate group having 1 to 20 carbon atoms, for example, an ethyldithiocarbonate group (C₂H₅SC(S)S—) and the like), a trithiocarbonate group (preferably a trithiocarbonate group having 1 to 20 carbon atoms, for example, an ethyltrithiocarbonate group (C₂H₅SC(S)S—) and the like), an acyl group (preferably an acyl group having 1 to 20 carbon atoms, for example, an acetyl group, a benzoyl group and the like), a selenocyanate group, an isoselenocyanate group, a thiocyanate group, an isothiocyanate group, a cyanate group, an isocyanate group, an isocyano group, a cyano group, an alkylthio group (preferably an alkylthio group having 1 to 20 carbon atoms, for example, a methanethio group, an ethylenedithio group, and the like), an arylthio group (preferably an arylthio group having 6 to 20 carbon atoms, for example, a benzenethio group, a 1,2-phenylenedithio group and the like), an alkoxy group (preferably an alkoxy group having 1 to 20 carbon atoms, for example, a methoxy group and the like) and an aryloxy group (preferably an aryloxy group having 6 to 20 carbon atoms, for example, a phenoxy group, a quinoline-8-hydroxyl group and the like), or a ligand composed of a halogen atom (preferably a chlorine atom, a bromine atom, an iodine atom and the like), a carbonyl ( . . . CO); a dialkylketone (preferably a dialkylketone having 3 to 20 carbon atoms, for example, acetone ((CH₃)₂CO . . . ) and the like), a 1,3-diketone (preferably a 1,3-diketone having 3 to 20 carbon atoms, for example, acetylacetone (CH₃C(O . . . )CH=C(O—)CH₃), a trifluoro acetylacetone (CF₃C(O . . . )CH=C(O—)CH₃), dipivaloylmethane (t-C₄H₉C(O . . . )CH=C(O—)t-C₄H₉), dibenzoylmethane (PhC(O . . . )CH=C(O—)Ph), 3-chloroacetylacetone (CH₃C(O . . . )CCl=C(O—)CH₃) and the like), a carbonamide group (preferably a carbonamide group having 1 to 20 carbon atoms, for example, CH₃N=C(CH₃)O—, —OC(=NH)—C(=NH)O— and the like), a thiocarbonamide group (preferably a thiocarbonamide group having 1 to 20 carbon atoms, for example, $CH_3N\!=\!C(CH_3)S\!-\!$ and the like), or a thiourea (preferably a thiourea having 1 to 20 carbon atoms, for example, $(NH(\ldots)\!=\!C(S\!-\!)NH_2$, $CH_3N(\ldots)\!=\!C(S\!-\!)NH\,CH_3$, $(CH_3)_2N\!-\!C(S\ldots)N(CH_3)_2$ and the like). Note that "..." indicates a coordinate bond with the metal atom M.

The ligand Z is preferably a ligand which coordinates through a coordinating group selected from the group consisting of an acyloxy group, a thioacylthio group, an acylaminooxy group, a dithiocarbamate group, a dithiocarbonate group, a trithiocarbonate group, a selenocyanate group, an isoselenocyanate group, a thiocyanate group, an isothiocyanate group, a cyanate group, an isocyanate group, an isocyano group, a cyano group, an alkylthio group, an arylthio group, an alkoxy group and an aryloxy group, or a ligand composed of a halogen atom, a carbonyl, a 1,3-diketone or a thiourea; more preferably a ligand which coordinates through a coordinating group selected from the group consisting of an acyloxy group, an acylaminooxy group, a dithiocarbamate group, a selenocyanate group, an isoselenocyanate group, a thiocyanate group, an isothiocyanate group, a cyanate group, an isocyanate group, an isocyano group, a cyano group and an arylthio group, or a ligand composed of a halogen atom, a 1,3-diketone or a thiourea; further preferably a ligand which coordinates through a coordinating group selected from the group consisting of a dithiocarbamate group, a selenocyanate group, an isoselenocyanate group, a thiocyanate group, an isothiocyanate group, a cyanate group, an isocyanate group, an isocyano group and a cyano group, or a ligand composed of a halogen atom or a 1,3-diketone; especially preferably a ligand which coordinates through a coordinating group selected from the group consisting of a dithiocarbamate group, a selenocyanate group, an isoselenocyanate group, a thiocyanate group, an isothiocyanate group, a cyanate group and an isocyanate group, or a ligand composed of a halogen atom or a 1,3-diketone; and most preferably a ligand which coordinates through a coordinating group selected from the group consisting of an isoselenocyanate group, an isothiocyanate group and an isocyanate group, in view of electron-donative properties.

Note that in the case where the ligand Z includes an alkyl group, an alkenyl group, an alkynyl group, an alkylene group, or the like, these groups may be linear or branched, and may be substituted or unsubstituted. In the case where the ligand Z includes an aryl group, a heterocyclic group, a cycloalkyl group, or the like, these groups may be substituted or unsubstituted, and may be a single ring or a condensed ring.

In the case where the ligand Z is a bidentate ligand, Z is preferably a ligand which coordinates through a coordinating group selected from the group consisting of an acyloxy group, an acylthio group, a thioacyloxy group, a thioacylthio group, an acylaminooxy group, a thiocarbamate group, a dithiocarbamate group, a thiocarbonate group, a dithiocarbonate group, a trithiocarbonate group, an acyl group, an alkylthio group, an arylthio group, an alkoxy group and an aryloxy group, or a ligand composed of a 1,3-diketone, a carbonamide group, a thiocarbonamide group or a thiourea.

In the case where Z is a monodentate ligand, Z is preferably a ligand which coordinates through a coordinating group selected from the group consisting of a selenocyanate group, an isoselenocyanate group, a thiocyanate group, an isothiocyanate group, a cyanate group, an isocyanate group, a cyano group, an alkylthio group and an arylthio group, or a ligand composed of a halogen atom, a carbonyl, a dialkylketone or a thiourea.

Specific examples of the ligand Z are shown in the followings, but the present invention is not limited thereto. In addition, the structural formulas shown below are only one canonical structure among resonance structures that can form several structures, and distinction between a covalent bond (shown by a solid line) and a coordination bond (shown by a dotted line) is also formal, and does not represent absolute distinction.

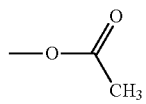

Z-1

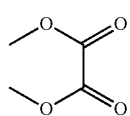

Z-2

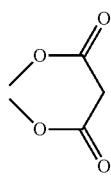

Z-3

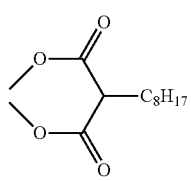

Z-4

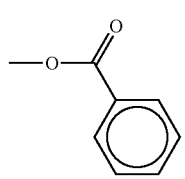

Z-5

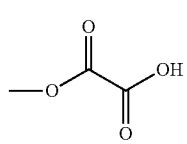

Z-6

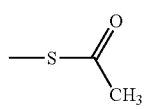

Z-7

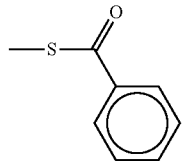

Z-8

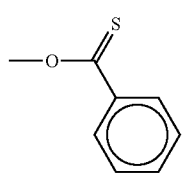

Z-9

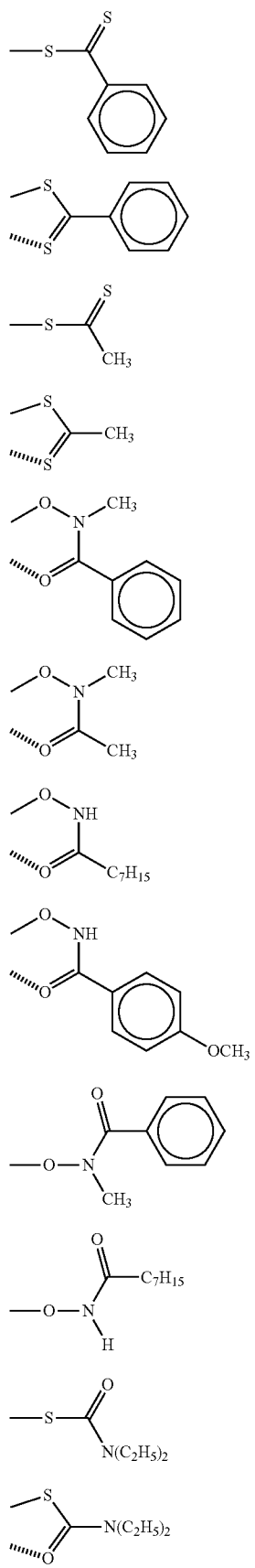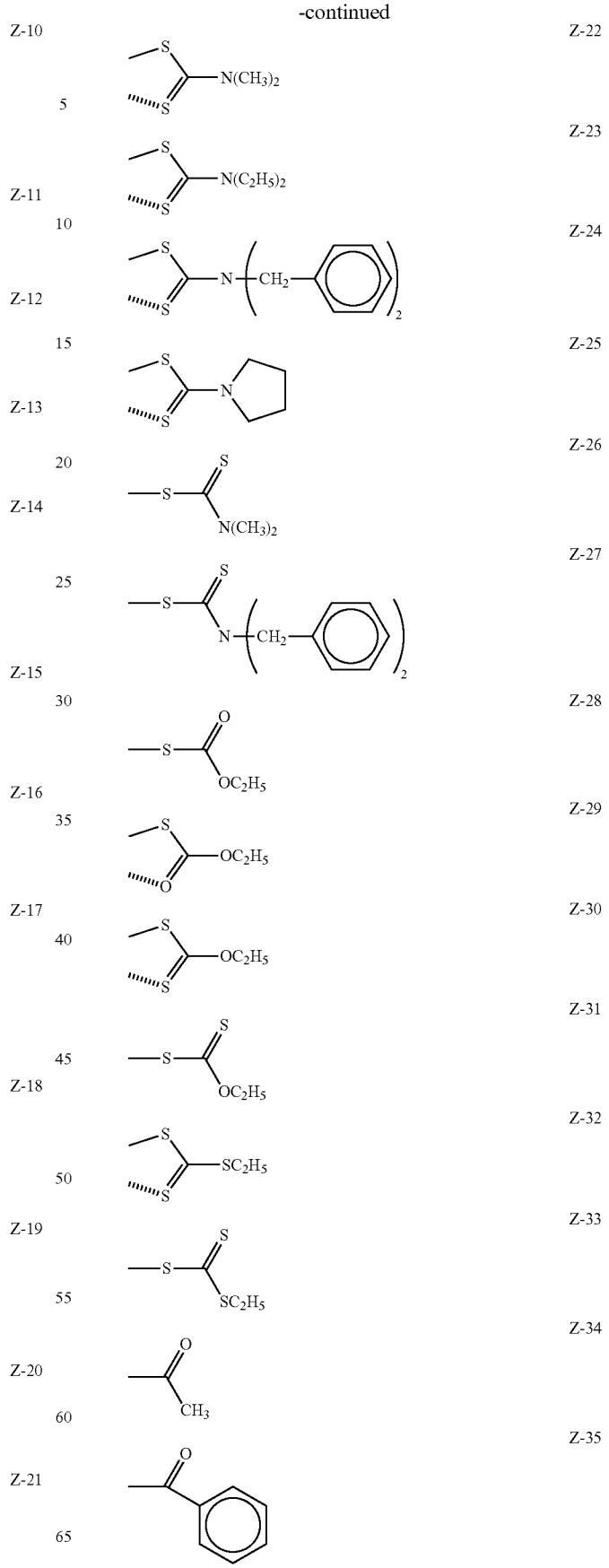

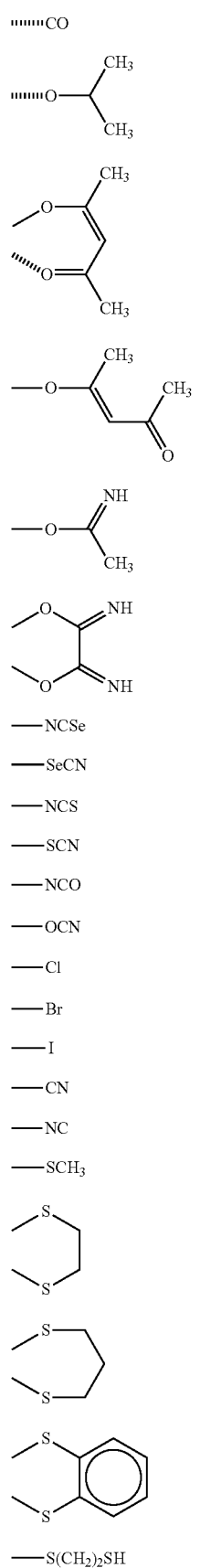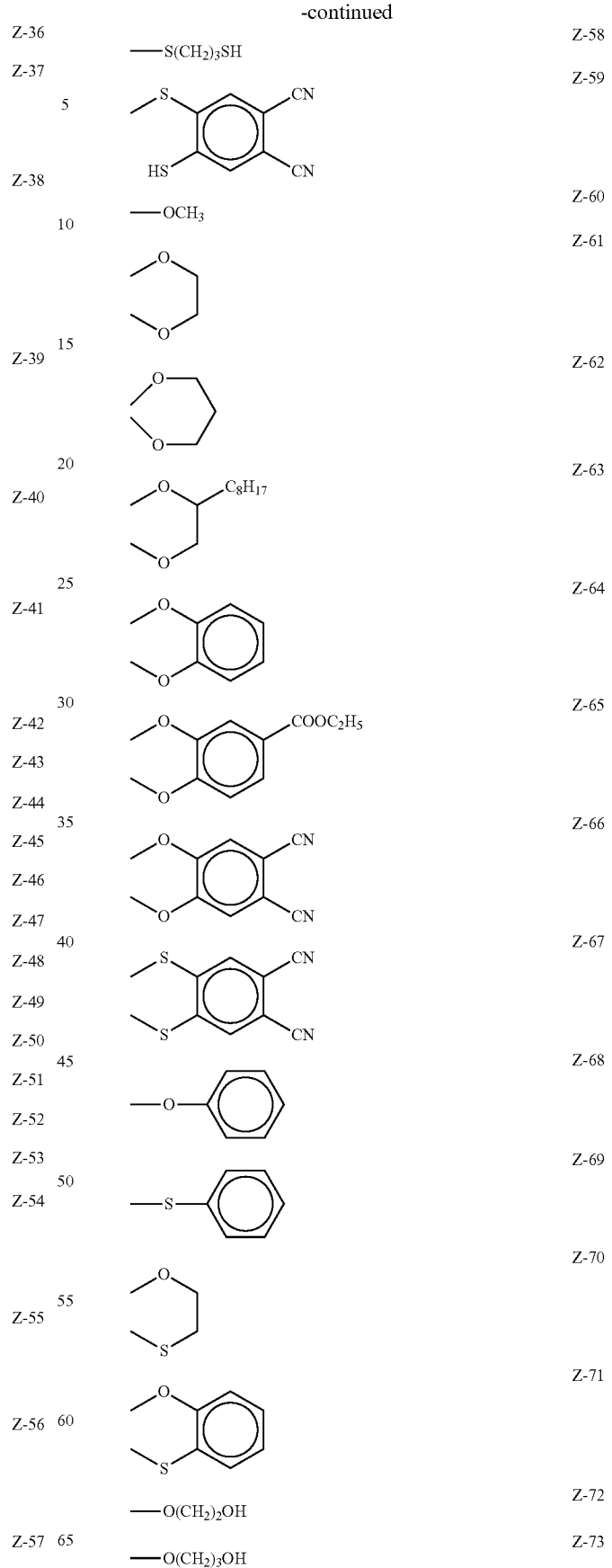

-continued
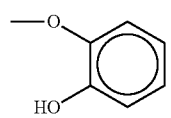
Z-74
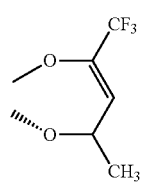
Z-75
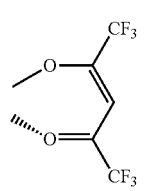
Z-76
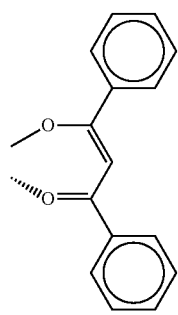
Z-77
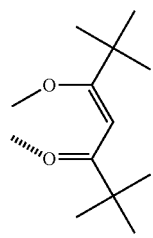
Z-78
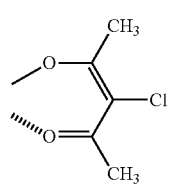
Z-79
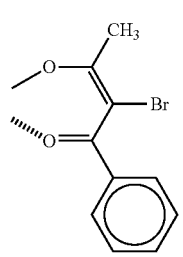
Z-80
-continued
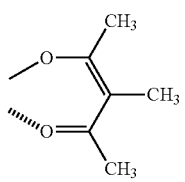
Z-81
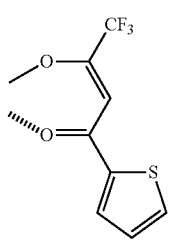
Z-82
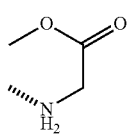
Z-83
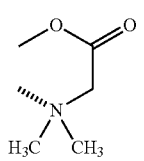
Z-84
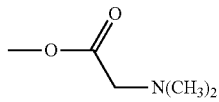
Z-85
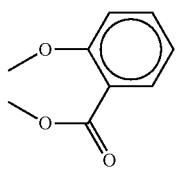
Z-86
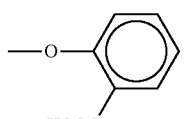
Z-87
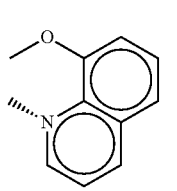
Z-88
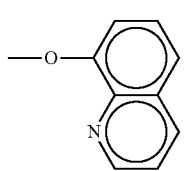
Z-89

-continued

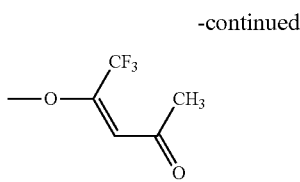

Z-90

CI in Formula (IX) represents a counter ion in the case where the counter ion is necessary to neutralize a charge. Whether the dye is cationic or anionic, or has a net ionic charge depends on the metal, the ligand and the substituent in the dye. In the case where the substituent has a dissociative group such as an acidic group, the dye may have a negative charge with the dissociation. In this case, an electric charge of the molecule as a whole is neutralized with the CI.

The positive counter ion is the same as a counter ion of $A^1$ and $A^2$ representing the acidic group.

The negative counter ion may be an inorganic negative ion or an organic negative ion. Examples thereof include a halogen negative ion (for example, fluoride ion, chloride ion, bromide ion, iodide ion and the like), a substituted arylsulfonate ion (for example, p-toluene sulfonate ion, p-chlorobenzene sulfonate ion and the like), an aryldisulfonate ion (for example, 1,3-benzene disulfonate ion, 1,5-naphthalene disulfonate ion, 2,6-naphthalene disulfonate ion and the like), an alkylsulfate ion (for example, methylsulfate ion and the like), a sulfate ion, a thiocyanate ion, a perchlorate ion, a tetrafluoroborate ion, a hexafluorophosphae ion, a picrate ion, an acetate ion and a trifluoromethane sulfonate ion. Alternatively, as a charge balance counter ion, an ionic polymer or another dye with the opposite charge from the primary dye may be used. Alternatively, a metal complex ion (for example, bisbenzene-1,2-dithiolatonickel (III) and the like) may be used.

The ligand LL2 is preferably a ligand represented by Formula (XI).

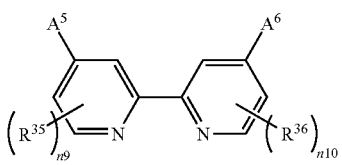

Formula (XI)

In Formula (XI), $A^5$ and $A^6$ each independently represent an acidic group or a salt thereof. Examples of the acidic group include a carboxylic acid group (a carboxyl group), a sulfonic acid group, a phosphonic acid group, a phenolic hydroxyl group, an alkylsulfonylamino group, a phosphoric acid group, a squaric acid group, a silicic acid group and a boric acid group. Preferred examples include a carboxylic acid group, a sulfonic acid group, a phosphonic acid group and a phenolic hydroxyl group; more preferred examples include a carboxylic acid group and a sulfonic acid group; and particularly preferred examples include a carboxylic acid group.

In Formula (XI), $R^{35}$ and $R^{36}$ each independently represent a substituent, and examples thereof include the substituent W described above. The substituent is preferably an alkyl group, an aryl group, a heterocyclic group, an alkoxy group, an aryloxy group or a halogen atom; further preferably an alkyl group, an alkoxy group, an aryl group or an aryloxy group; and particularly preferably an alkyl group or an aryl group.

In Formula (XI), n9 and n10 each independently represent an integer of 0 to 3. When n9 is an integer of 2 or more, $R^{35}$'s may be the same or different from each other, or $R^{35}$'s may be bonded to each other to form a ring. When n10 is an integer of 2 or more, $R^{36}$'s may be the same or different from each other, or $R^{36}$'s may be bonded to each other to form a ring. When n9 and n10 each are an integer of 1 or more, $R^{35}$ and $R^{36}$ may be bonded to each other to form a ring. Preferred examples of these rings to be formed include a benzene ring, a pyridine ring, a thiophene ring, a pyrrole ring, a furan ring, a cyclohexane ring, and a cyclopentane ring.

n9 and n10 each are preferably an integer of 0 to 3, further preferably an integer of 0 or 1, and particularly preferably 0.

The ligand LL2 is preferably represented by Formula (XII).

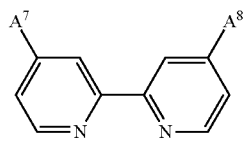

Formula (XII)

In Formula (XII), $A^7$ and $A^8$ each independently represent an acidic group or a salt thereof. Examples of the acidic group include a carboxylic acid group (a carboxyl group), a sulfonic acid group, a phosphonic acid group, a phenolic hydroxyl group, an alkylsulfonylamino group, a phosphoric acid group, a squaric acid group, a silicic acid group and a boric acid group. Preferred examples include a carboxylic acid group, a sulfonic acid group, a phosphonic acid group and a phenolic hydroxyl group; more preferred examples include a carboxylic acid group and a sulfonic acid group; and particularly preferred examples include a carboxylic acid group.

The metal complex dye represented by Formula (IX) is preferably represented by any one of Formulas (XIII) to (XV); further preferably Formula (XIII) or Formula (XV); and particularly preferably Formula (XIII)

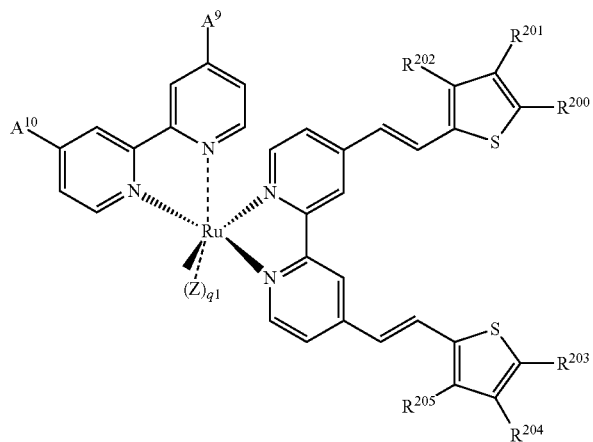
Formula (XIII)
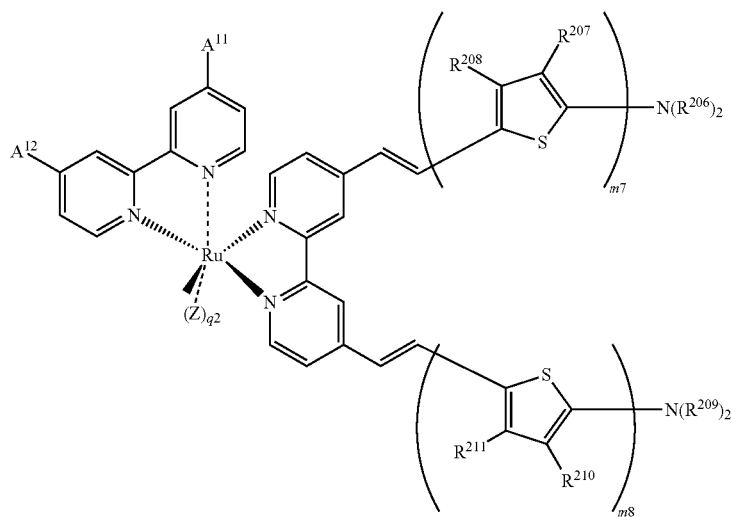
Formula (XIV)
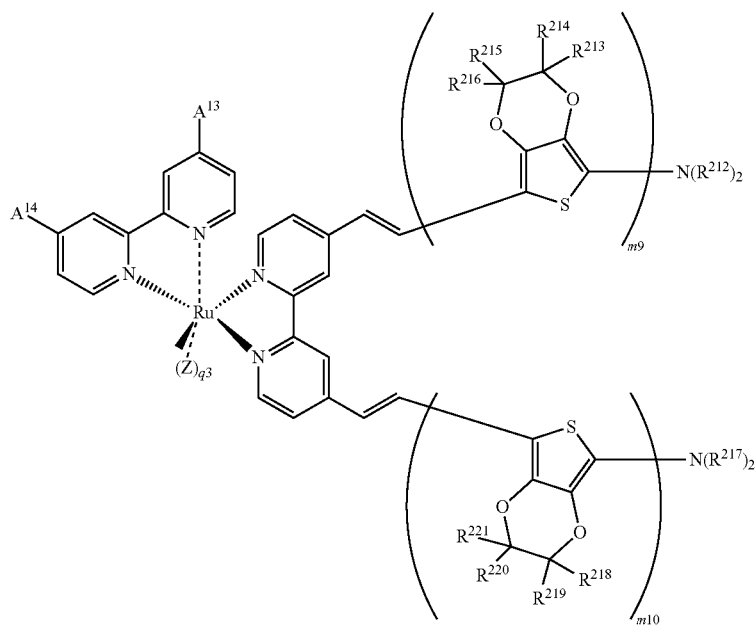
Formula (XV)

In Formulas (XIII) to (XV), $A^9$, $A^{10}$, $A^{11}$, $A^{12}$, $A^{13}$ and $A^{14}$ each independently represent a carboxyl group or a salt thereof.

$R^{200}$ and $R^{203}$ each have the same meaning as that of $R^5$ in Formula (II), and the preferable ranges thereof are also the same. $R^{201}$ and $R^{204}$ have the same meaning as $R^7$ in Formula (II), and the preferable ranges thereof are also the same. $R^{202}$ and $R^{205}$ have the same meaning as $R^6$ in Formula (II), and the preferable ranges thereof are also the same. $R^{207}$, $R^{208}$, $R^{210}$ and $R^{21}$ have the same meaning as $R^{25}$ in Formula (VII), and the preferable ranges thereof are also the same. $R^{213}$ to $R^{216}$ and $R^{218}$ to $R^{221}$ have the same meaning as $R^{28}$ in Formula (VIII), and the preferable ranges thereof are also the same.

Herein, at least one of $R^{207}$ and $R^{208}$ is an alkyl group, and at least one of $R^{210}$ and $R^{211}$ is an alkyl group. The preferable ranges thereof as alkyl groups at least one of which is included are the same as the ranges in the case of Formulas (II) to (VIII).

Each of $R^{201}$ and $R^{202}$, $R^{204}$ and $R^{205}$, $R^{207}$ and $R^{208}$, $R^{210}$ and $R^{211}$, any of $R^{213}$ to $R^{216}$, and any of $R^{218}$ to $R^{221}$ may be bonded with each other to form a ring. The preferable ranges as the rings to be formed are the same as the ranges in the case of Formulas (II) to (VIII).

$R^{206}$ and $R^{209}$ have the same meaning as $R^{24}$ in Formula (VII), and the preferable ranges thereof are also the same. $R^{212}$ and $R^{217}$ have the same meaning as $R^{27}$ in Formula (VIII), and the preferable ranges thereof are also the same.

Then, m7 to m10 each independently represent an integer of 1 to 5.

Z represents a monodentate or bidentate ligand and has the same meaning as Z in Formula (IX), and the preferable range thereof is also the same.

Then, q1 to q3 each independently represent an integer of 1 or 2, preferably 2.

The metal complex dye represented by Formula (XIII) is adsorbed on an oxide semiconductor surface through $A^9$ or $A^{10}$. In particular, $R^5$ is spatially located on an electrolyte side opposite to the oxide semiconductor surface seen from the dye. Therefore, a smooth reduction effect from the redox system can be expected. In Formula (XV), a highly electron-donative ethylenedioxy group is bonded with the thiophene ring, and thus potential of HOMO of the dye is negatively shifted, and the bonding contributes to wavelength elongation.

When the metal complex dye of the present invention is dissolved in a solvent, preferably an organic solvent or a mixed solvent of an organic solvent and water, and further preferably a solvent of THF/water (=6:4, trifluoroacetic acid 0.1 v/v %), methanol or ethanol, in particular, a solvent of THF/water (=6:4, trifluoroacetic acid 0.1 v/v %), a wavelength of maximum absorbance on the longest wavelength side in a solution when the dye is dissolved in the solvent is preferably in the range of 350 to 1200 nm, further preferably in the range of 400 to 900 nm, and particularly preferably in the range of 450 to 700 nm. A mixing ratio of THF and water is expressed in terms of a volume ratio.

Specific examples of the metal complex dye represented by Formula (IX) are shown in the followings, but the present invention is not limited thereto. As these acidic groups, only a proton undissociator is shown, but these acidic groups each may be a proton dissociator or may have the above-mentioned counter ion. When a carbon-carbon double bond is present, these compounds each may be an E isomer or a Z isomer, or a mixture thereof, or an isomer such as a cis isomer, a trans isomer or an optically active substance as the complex, but are not particularly limited thereto, and may be a single isomer or a mixture thereof.

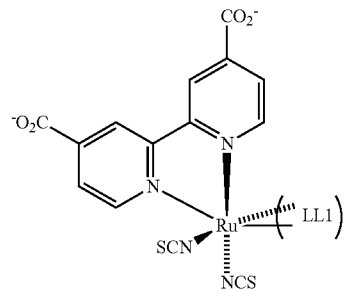

| | LL1 | CI |
|---|---|---|
| D-1-1a | A-1-3 | $(H^+)_2$ |
| D-1-1b | A-1-3 | $(H^+)(N^+Bu_4)$ |
| D-1-1c | A-1-3 | $(N^+Bu_4)_2$ |
| D-1-2 | A-2-3 | $(H^+)_2$ |
| D-1-3 | A-3-4 | $(H^+)_2$ |
| D-1-4 | A-5-1 | $(H^+)_2$ |
| D-1-5 | A-5-2 | $(H^+)_2$ |
| D-1-6 | A-5-3 | $(H^+)_2$ |
| D-1-7 | A-5-4 | $(H^+)_2$ |
| D-1-8a | A-5-5 | $(H^+)_2$ |
| D-1-8b | A-5-5 | $(H^+)(N^+Bu_4)$ |
| D-1-8c | A-5-5 | $(N^+Bu_4)_2$ |
| D-1-9 | A-5-6 | $(H^+)_2$ |
| D-1-10 | A-5-7 | $(H^+)_2$ |
| D-1-11 | A-5-8 | $(H^+)_2$ |
| D-1-12 | A-6-2 | $(H^+)_2$ |
| D-1-13 | A-7-2 | $(H^+)_2$ |
| D-1-14 | A-16-1 | $(H^+)_2$ |
| D-1-15 | A-9-14 | $(H^+)_2$ |
| D-1-16a | A-10-2 | $(H^+)_2$ |
| D-1-16b | A-10-2 | $(H^+)(N^+Bu_4)$ |
| D-1-16c | A-10-2 | $(N^+Bu_4)_2$ |
| D-1-17a | A-11-2 | $(H^+)_2$ |
| D-1-17b | A-11-2 | $(H^+)(N^+Bu_4)$ |
| D-1-17c | A-11-2 | $(N^+Bu_4)_2$ |
| D-1-18 | A-12-2 | $(H^+)_2$ |
| D-1-19 | A-13-4 | $(H^+)_2$ |
| D-1-20 | A-14-1 | $(H^+)_2$ |
| D-1-21a | A-16-2 | $(H^+)_2$ |
| D-1-21b | A-16-2 | $(H^+)(N^+Bu_4)$ |
| D-1-21c | A-16-2 | $(N^+Bu_4)_2$ |
| D-1-22a | A-2-3 | $(H^+)_2$ |
| D-1-22b | A-2-3 | $(H^+)(N^+Bu_4)$ |
| D-1-22c | A-2-3 | $(N^+Bu_4)_2$ |
| D-1-23a | A-3-3 | $(H^+)_2$ |
| D-1-23b | A-3-3 | $(H^+)(N^+Bu_4)$ |
| D-1-23c | A-3-3 | $(N^+Bu_4)_2$ |
| D-1-24a | A-16-1 | $(H^+)_2$ |
| D-1-24b | A-16-2 | $(H^+)(N^+Bu_4)$ |
| D-1-24c | A-16-3 | $(N^+Bu_4)_2$ |

-continued

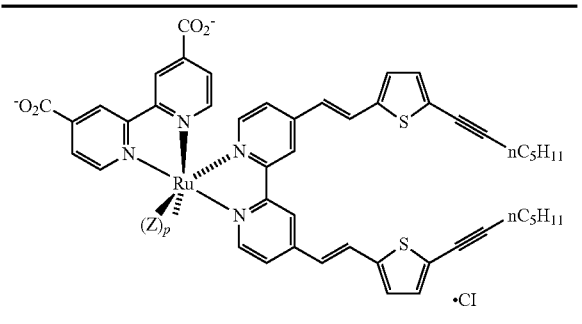

| | (Z)p | Cl |
|---|---|---|
| D-2-1 | (Z-42)$_2$ | (H$^+$)$_2$ |
| D-2-2 | (Z-46)$_2$ | (H$^+$)$_2$ |
| D-2-3 | (Z-48)$_2$ | (H$^+$)$_2$ |
| D-2-4 | (Z-49)$_2$ | (H$^+$)$_2$ |
| D-2-5 | (Z-50)$_2$ | (H$^+$)$_2$ |
| D-2-6 | Z-77 | H$^+$ |
| D-2-7 | Z-38 | H$^+$ |
| D-2-8 | Z-75 | H$^+$ |

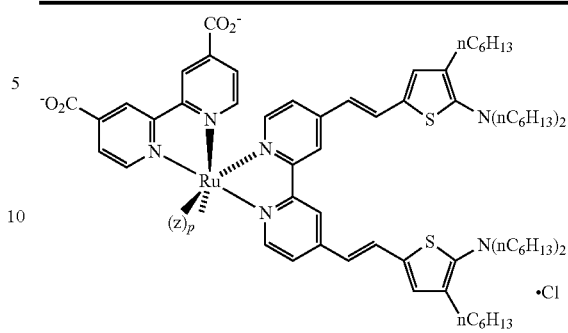

| | (Z)p | Cl |
|---|---|---|
| D-4-4 | (Z-49)2 | (H$^+$)$_2$ |
| D-4-5 | (Z-50)2 | (H$^+$)$_2$ |
| D-4-6 | Z-77 | H$^+$ |
| D-4-7 | Z-38 | H$^+$ |

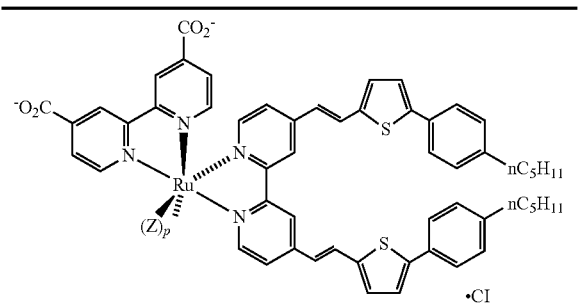

| | (Z)p | Cl |
|---|---|---|
| D-3-1 | (Z-42)$_2$ | (H$^+$)$_2$ |
| D-3-2 | (Z-46)$_2$ | (H$^+$)$_2$ |
| D-3-3 | (Z-48)$_2$ | (H$^+$)$_2$ |
| D-3-4 | (Z-49)$_2$ | (H$^+$)$_2$ |
| D-3-5 | (Z-50)$_2$ | (H$^+$)$_2$ |
| D-3-6 | Z-77 | H$^+$ |
| D-3-7 | Z-38 | H$^+$ |

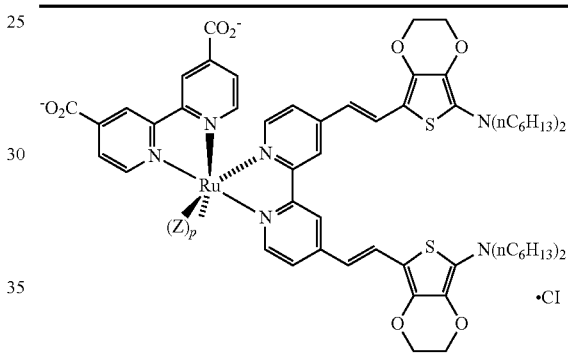

| | (Z)p | Cl |
|---|---|---|
| D-5-1 | (Z-42)$_2$ | (H$^+$)$_2$ |
| D-5-2 | (Z-46)$_2$ | (H$^+$)$_2$ |
| D-5-3 | (Z-48)$_2$ | (H$^+$)$_2$ |
| D-5-4 | (Z-49)$_2$ | (H$^+$)$_2$ |
| D-5-5 | (Z-50)$_2$ | (H$^+$)$_2$ |
| D-5-6 | Z-77 | H$^+$ |
| D-5-7 | Z-38 | H$^+$ |

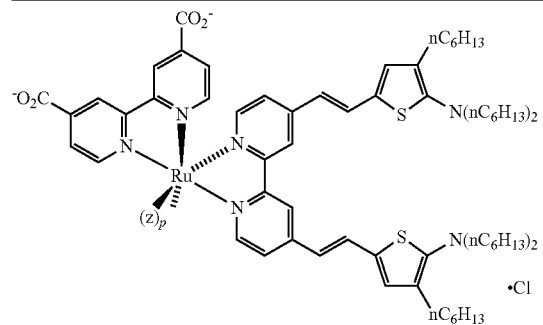

| | (Z)p | Cl |
|---|---|---|
| D-4-1 | (Z-42)2 | (H$^+$)$_2$ |
| D-4-2 | (Z-46)2 | (H$^+$)$_2$ |
| D-4-3 | (Z-48)2 | (H$^+$)$_2$ |

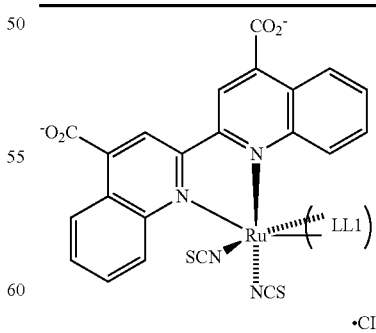

| | LL1 | Cl |
|---|---|---|
| D-6-1 | A-1-3 | (H$^+$)$_2$ |
| D-6-2 | A-2-3 | (H$^+$)$_2$ |
| D-6-3 | A-3-4 | (H$^+$)(N$^+$Bu$_4$) |

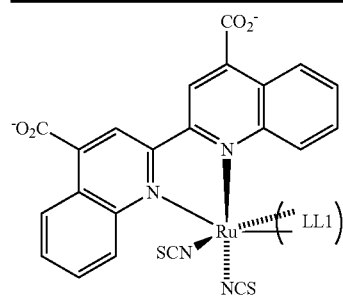

| | LL1 | Cl |
|---|---|---|
| D-6-4 | A-5-1 | $(H^+)_2$ |
| D-6-5 | A-5-2 | $(H^+)_2$ |
| D-6-6 | A-5-3 | $(H^+)_2$ |
| D-6-7 | A-5-4 | $(H^+)_2$ |
| D-6-8 | A-5-5 | $(H^+)(N^+Bu_4)$ |
| D-6-9 | A-5-6 | $(H^+)_2$ |
| D-6-10 | A-5-7 | $(H^+)_2$ |
| D-6-11 | A-5-8 | $(H^+)_2$ |
| D-6-12 | A-6-2 | $(H^+)_2$ |
| D-6-13 | A-7-2 | $(H^+)(N^+Bu_4)$ |
| D-6-14 | A-16-1 | $(H^+)_2$ |
| D-6-15 | A-9-14 | $(H^+)_2$ |
| D-6-16 | A-10-2 | $(H^+)_2$ |
| D-6-17 | A-11-2 | $(H^+)(N^+Bu_4)$ |
| D-6-18 | A-12-2 | $(H^+)_2$ |
| D-6-19 | A-13-4 | $(H^+)_2$ |
| D-6-20 | A-14-1 | $(H^+)_2$ |
| D-6-21 | A-16-2 | $(H^+)(N^+Bu_4)$ |
| D-6-22 | A-2-3 | $(H^+)_2$ |
| D-6-23 | A-3-3 | $(H^+)(N^+Bu_4)$ |

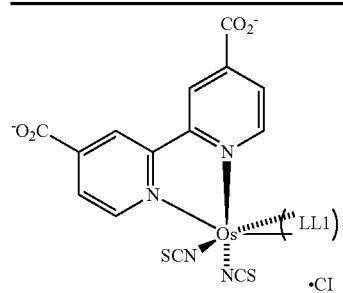

| | LL1 | Cl |
|---|---|---|
| D-7-1 | A-1-3 | $(H^+)_2$ |
| D-7-2 | A-2-3 | $(H^+)_2$ |
| D-7-3 | A-3-4 | $(H^+)(N^+Bu_4)$ |
| D-7-4 | A-5-1 | $(H^+)_2$ |
| D-7-5 | A-5-2 | $(H^+)_2$ |
| D-7-6 | A-5-3 | $(H^+)_2$ |
| D-7-7 | A-5-4 | $(H^+)_2$ |
| D-7-8 | A-5-5 | $(H^+)(N^+Bu_4)$ |
| D-7-9 | A-5-6 | $(H^+)_2$ |
| D-7-10 | A-5-7 | $(H^+)_2$ |
| D-7-11 | A-5-8 | $(H^+)_2$ |
| D-7-12 | A-6-2 | $(H^+)_2$ |
| D-7-13 | A-7-2 | $(H^+)(N^+Bu_4)$ |
| D-7-14 | A-16-1 | $(H^+)_2$ |
| D-7-15 | A-9-14 | $(H^+)_2$ |
| D-7-16 | A-10-2 | $(H^+)_2$ |
| D-7-17 | A-11-2 | $(H^+)(N^+Bu_4)$ |
| D-7-18 | A-12-2 | $(H^+)_2$ |
| D-7-19 | A-13-4 | $(H^+)_2$ |
| D-7-20 | A-14-1 | $(H^+)_2$ |
| D-7-21 | A-16-2 | $(H^+)(N^+Bu_4)$ |
| D-7-22 | A-2-3 | $(H^+)_2$ |
| D-7-23 | A-3-3 | $(H^+)(N^+Bu_4)$ |

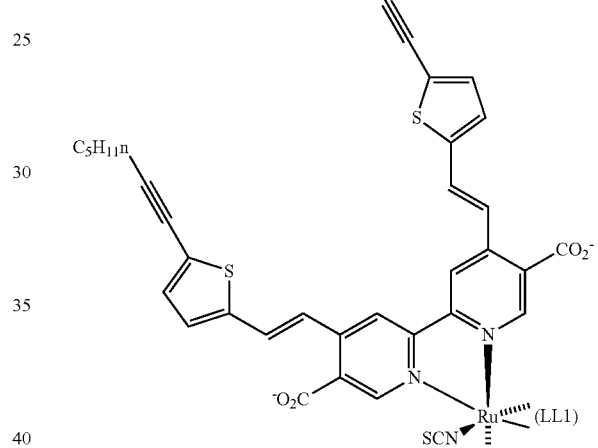

| | LL1 | Cl |
|---|---|---|
| D-8-1a | A-17-3 | $(H^+)_4$ |
| D-8-1b | A-17-3 | $(H^+)_2(N^+Bu_4)_2$ |
| D-8-1c | A-17-3 | $(N^+Bu_4)_4$ |
| D-8-2a | A-10-3 | $(H^+)_4$ |
| D-8-2b | A-10-3 | $(H^+)_2(N^+Bu_4)_2$ |
| D-8-2c | A-10-3 | $(N^+Bu_4)_4$ |

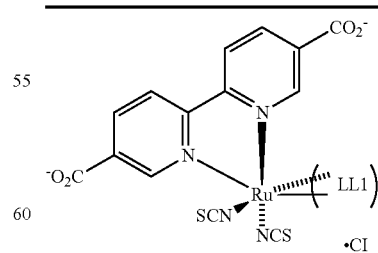

| | LL1 | Cl |
|---|---|---|
| D-9-1a | A-1-3 | $(H^+)_2$ |
| D-9-1b | A-1-3 | $(H^+)(N^+Bu_4)$ |
| D-9-1c | A-1-3 | $(N^+Bu_4)_2$ |

-continued

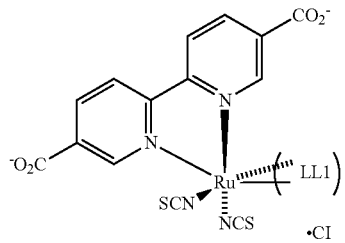

| | LL1 | CI |
|---|---|---|
| D-9-2a | A-10-2 | $(H^+)_2$ |
| D-9-2b | A-10-2 | $(H^+)(N^+Bu_4)$ |
| D-9-2c | A-10-2 | $(N^+Bu_4)_2$ |
| D-9-3a | A-11-2 | $(H^+)_2$ |
| D-9-3b | A-11-2 | $(H^+)(N^+Bu_4)$ |
| D-9-3c | A-11-2 | $(N^+Bu_4)_2$ |
| D-9-4a | A-16-2 | $(H^+)_2$ |
| D-9-4b | A-16-2 | $(H^+)(N^+Bu_4)$ |
| D-9-4c | A-16-2 | $(N^+Bu_4)_2$ |
| D-9-5a | A-2-3 | $(H^+)_2$ |
| D-9-5b | A-2-3 | $(H^+)(N^+Bu_4)$ |
| D-9-5c | A-2-3 | $(N^+Bu_4)_2$ |
| D-9-6a | A-3-3 | $(H^+)_2$ |
| D-9-6b | A-3-3 | $(H^+)(N^+Bu_4)$ |
| D-9-6c | A-3-3 | $(N^+Bu_4)_2$ |
| D-9-7a | A-16-1 | $(H^+)_2$ |
| D-9-7b | A-16-2 | $(H^+)(N^+Bu_4)$ |
| D-9-7c | A-16-3 | $(N^+Bu_4)_2$ |
| D-9-8a | A-5-5 | $(H^+)_2$ |
| D-9-8b | A-5-5 | $(H^+)(N^+Bu_4)$ |
| D-9-8c | A-5-5 | $(N^+Bu_4)_2$ |

The metal complex dye containing the ligand LL1 having the structure represented by Formula (I) according to the present invention can be synthesized with reference to the methods in the literatures of J. Am. Chem. Soc., 121, 4047 (1997), Can. J. Chem., 75, 318 (1997), Inorg. Chem., 27, 4007 (1988) or the like, and the methods cited in the literatures. In particular, as for a change of counter cations, as shown in Synthesis Examples, types of cations can be freely changed by treating the cations with a base and dissolving the cations therein, and further an amount of counter cations other than the proton can be adjusted by adjusting pH from an amount of acidic reagent to be used.

Preferred examples of the base to be used include tetraalkylammonium hydroxide and metal hydroxide.

When the metal complex dye of the present invention is used for the photoelectric conversion element described later, the dye may be used alone or in combination with other dyes. Among the other dyes, at least one kind of dye (preferably a dye other than the metal complex dye having the ligand LL1 represented by Formula (I) according to the present invention, and the dye used in combination therewith) preferably has the maximum absorption wavelength of 600 nm or more on the longest wavelength side in THF/water (=6:4, trifluoroacetic acid 0.1 v/v %) solution.

Sunlight can be efficiently photoelectrically converted by combination with a dye that efficiently photoelectrically converts light on a longer wavelength side, as compared with the metal complex dye having the ligand LL1 represented by Formula (I) according to the present invention. The dye to be combined is preferably a porphyrin dye, a squarylium dye or a phthalocyanine dye; further preferably a porphyrin dye or a squarylium dye; and particularly preferably a squarylium dye. Among the porphyrin dyes, a binuclear complex is preferable. Among the squarylium dyes, bissquarylium having two squarylium skeletons is preferable.

In the present invention, when the dye is used for the photoelectric conversion element described later, a co-adsorbent is preferably used for the metal complex dye of the present invention or the dye used in combination therewith. As such a co-adsorbent, a co-adsorbent having a carboxyl group or a salt thereof is preferable, and examples of the co-adsorbent include a fatty acid and a compound having a steroid skeleton.

The fatty acid may be a saturated fatty acid or an unsaturated fatty acid. Examples thereof include a butanoic acid, a hexanoic acid, an octanoic acid, a decanoic acid, a hexadecanoic acid, a dodecanoic acid, a palmitic acid, a stearic acid, an oleic acid, a linoleic acid, and a linolenic acid.

Examples of the compound having a steroid skeleton include a cholic acid, a glycocholic acid, a chenodeoxycholic acid, a hyocholic acid, a deoxycholic acid, a lithocholic acid, and ursodeoxycholic acid. Among these, a cholic acid, a deoxycholic acid, and a chenodeoxycholic acid are preferable; and a chenodeoxycholic acid is further preferable.

A preferred co-adsorbent is a compound represented by Formula (XVI).

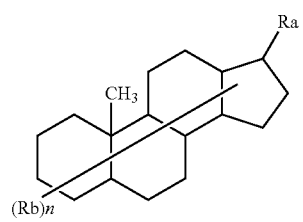

Formula (XVI)

In Formula (XVI), Ra represents an alkyl group having only one (1) acidic group or a salt thereof. Rb represents a substituent, and examples thereof include the substituent W described above. Then, n represents an integer of 0 or more. When n is an integer of 2 or more, Rb's may be the same or different from each other. Examples of the specific compounds include a compound that is exemplified as the above-mentioned compound having a steroid skeleton.

The co-adsorbent that can be used in the present invention exerts an effect on suppressing the inefficient association of the dye and preventing reverse electron migration from the oxide semiconductor surface to the redox system in the electrolyte by adsorbing on the semiconductor fine particles.

[Photoelectric Conversion Element and Dye-Sensitized Solar Cell]

As shown in FIG. 1, the photoelectric conversion element 10 of the present invention includes an electrically conductive support 1; a photosensitive layer (semiconductor film or semiconductor layer) 2 provided on the electrically conductive support 1, the photosensitive layer having porous semiconductor fine particles to which a metal complex dye (dye 21) of the present invention has been adsorbed; a charge transfer layer (that may also serve as the hole transport layer) 3; and a counter electrode 4. The electrically conductive support having a semiconductor film provided thereon functions as a working electrode in the photoelectric conversion element. In this embodiment, this photoelectric conversion element 10 can be operated as a dye-sensitized solar cell 100 by making the element usable in a cell application where the cell is made to work with an external circuit 6.

In this embodiment, a light-receiving electrode 5 is an electrode comprising an electrically conductive support 1; and a photosensitive layer (photoconductor layer) 2 coated on the electrically conductive support, the layer containing semiconductor fine particles 22 to which a dye compound 21 has been adsorbed. In this embodiment, the electrolyte is contained in the light-receiving electrode 5, and in either one or both of the photoconductor layer 2 and the charge transfer object layer 3. The photoconductor layer 2 is designed for any purpose, and may have a monolayer constitution or a multi-layered constitution. The dye compound 21 in one layer of the photoconductor layer may be one kind or a mixture of a plurality of kinds, and the above-mentioned metal complex dye of the present invention is used as at least one kind of the compounds. A light incident to the photosensitive layer 2 excites the dye. The excited dye has electrons with high energy, and these electrons are transported from the dye compound 21 to the conduction band of the semiconductor fine particles 22 and further reach the electrically conductive support 1 by diffusion. At this time, the metal complex dye is in an oxide form; however, in a dye-sensitized solar cell, the electrons on the electrode return to the oxide of the dye while working in the external circuit 6, while the dye-sensitized photoelectric conversion element works as a negative electrode of this cell. Regarding materials used for a photoelectric conversion element and a dye-sensitized solar cell, and a method of producing each member in the present invention, ordinary ones in this art may be used, and these materials and methods may be referred to, for example, U.S. Pat. No. 4,927,721, U.S. Pat. No. 4,684,537, U.S. Pat. No. 5,084,365, U.S. Pat. No. 5,350,644, U.S. Pat. No. 5,463,057, U.S. Pat. No. 5,525,440, JP-A-7-249790, JP-A-2004-220974 and JP-A-2008-135197. Hereinafter, principal members are described appropriately.

The electrically conductive support is a support having electroconductivity per se, such as a metal, or a support of glass or a polymeric material having an electrically conductive layer on the surface. In addition to the glass and the plastic, ceramic (JP-A-2005-135902), an electric conductive resin (JP-A-2001-160425) or the like may be used as the support. The support may be provided with a light management function at the surface, and for example, the anti-reflective film having a high refractive index film and a low refractive index oxide film alternately laminated as described in JP-A-2003-123859, and the light guide function as described in JP-A-2002-260746 may be mentioned.

The thickness of the conductive film layer is preferably 0.01 to 30 μm, more preferably 0.03 to 25 μm, and particularly preferably 0.05 to 20 μm.

It is preferable that the electrically conductive support is substantially transparent. The terms "substantially transparent" means that the transmittance of light is 10% or more, preferably 50% or more, particularly preferably 80% or more. As the electrically conductive support, a support formed from glass or a plastic and coated with an electrically conductive metal oxide is preferable. In this case, the amount of coating of the conductive metal oxide is preferably 0.1 to 100 g per square meter of the support made of glass or a plastic. In the case of using a transparent conductive support, it is preferable that light is incident from the support side.

Regarding the semiconductor fine particles, fine particles of chalcogenides of metals (for example, oxides, sulfides and selenides), or fine particles of perovskites may be used with preference. Preferred examples of the chalcogenides of metals include oxides of titanium, tin, zinc, tungsten, zirconium, hafnium, strontium, indium, cerium, yttrium, lanthanum, vanadium, niobium or tantalum, cadmium sulfide, and cadmium selenide. Preferred examples of the perovskites include strontium titanate, and calcium titanate. Among these, titanium oxide, zinc oxide, tin oxide, and tungsten oxide are particularly preferred.

Examples of the crystal structure of titania include structures of anatase type, brookite type and rutile type, and anatase type and brookite type structures are preferred in the present invention. A titania nanotube/nanowire/nanorod may be mixed with titania fine particles or may be used as a semiconductor electrode.

A particle size of the semiconductor fine particles is expressed in terms of an average particle size using a diameter when a projected area is converted into a circle, and is preferably 0.001 to 1 μm as primary particles, and 0.01 to 100 μm as an average particle size of dispersions. Examples of the method for coating the semiconductor fine particles on the electrically conductive support include a wet method, a dry method or other methods.

It is preferable to form a short circuit preventing layer between the transparent electrically conductive film and the photoconductor layer (oxide semiconductor layer), so as to prevent reverse current due to a direct contact between the electrolyte liquid and the electrode. It is preferable to employ a spacer or a separator so as to prevent the contact between the light-receiving electrode and the counter electrode. It is preferable for the semiconductor fine particles to have a large surface area, so that a large amount of dye can adsorb to the surface. For example, while the semiconductor fine particles have been coated on the support, the surface area is preferably 10 times or more, and more preferably 100 times or more, relative to the projected surface area. The upper limit of this value is not particularly limited, but the upper limit is usually about 5000 times. In general, as the thickness of the semiconductor fine particle layer increases, the amount of dye that can be supported per unit area increases, and therefore, the light absorption efficiency is increased. However, since the diffusion distance of generated electrons increases along, the loss due to charge recombination is also increased. Although a preferred thickness of the semiconductor fine particle layer may vary with the utility of the element, the thickness is typically 0.1 to 100 μm. In the case of using the photoelectric conversion element for a dye-sensitized solar cell, the thickness of the semiconductor fine particle layer is preferably 1 to 50 μm, and more preferably 3 to 30 μm. The semiconductor fine particles may be calcined after being applied on the support, at a temperature of 100 to 800° C. for 10 minutes to 10 hours, so as to bring about cohesion of the particles. When a glass support is used, the film forming temperature is preferably 400 to 60° C.

The amount of coating of the semiconductor fine particles per square meter of the support is preferably 0.5 to 500 g, and more preferably 5 to 100 g. The overall amount of use of the dye is preferably 0.01 to 100 millimoles, more preferably 0.1 to 50 millimoles, and particularly preferably 0.1 to 10 millimoles, per square meter of the support. In this case, the amount of use of the dye of the present invention is preferably adjusted to 5% by mole or more. The amount of the dye adsorbed to the semiconductor fine particles is preferably 0.001 to 1 millimole, and more preferably 0.1 to 0.5 millimoles, based on 1 g of the semiconductor fine particles. When the amount of the dye is adjusted to such a range, the sensitization effect for the semiconductor can be sufficiently obtained. On the other hand, if the amount of the dye is too smaller, the sensitization effect is insufficient, and if the amount of the dye is excessive, the portion of the dye that is not attached to the semiconductor is suspended, and causes a decrease in the sensitization effect. Dye adsorption onto the oxide semiconductor is preferably monolayer adsorption. If multilayer adsorption takes place, the electrons cannot be efficiently injected into the oxide semiconductor, and the conversion efficiency is decreased. When the ligand that has no acidic group to serve as an anchor upon adsorption onto the oxide semiconductor has a group such as an alkyl group or an alkynyl group in the dye, self organization is efficiently achieved and the monolayer adsorption is promoted. For the purpose of reducing the interaction between dye molecules such as association, a colorless compound may be co-adsorbed. Examples of the hydrophobic compound that is co-adsorbed include the above-described co-adsorbent. When the metal complex dye containing the ligand LL1 having the structure represented by Formula (I) according to the present invention is a salt, a counter ion of the metal complex dye containing the ligand LL1 having the structure represented by Formula (I) is not particularly limited. Examples thereof include an alkali metal ion and a quaternary ammonium ion.

After the dye has been adsorbed, the surface of the semiconductor fine particles may be treated using amines. Preferred examples of the amines include 4-tert-butylpyridine, and polyvinylpyridine. These may be used directly when the compounds are liquids, or may be used in a state of being dissolved in an organic solvent. The charge transfer layer is a layer having a function of supplementing electrons to an oxidant of the dye, and is provided between the light-receiving electrode and the counter electrode. Representative examples of the material forming the charge transfer layer include a liquid prepared by dissolving a redox pair in an organic solvent, a so-called gel electrolyte obtained by impregnating a polymer matrix with a liquid prepared by dissolving a redox pair in an organic solvent, and a molten salt containing a redox pair.

A solid charge transport system such as a p-type semiconductor or a hole transporting material may also be used instead of the liquid electrolytes and quasi-solid electrolytes described above. For a solid charge transport layer, an organic hole transporting material may be used.

The redox pair serves as a carrier for electrons, and thus is required at a certain concentration. A preferred overall concentration is 0.01 moles/L or more, more preferably 0.1 moles/L or more, and particularly preferably 0.3 moles/L or more. In this case, the upper limit of the concentration is not particularly limited, but is usually about 5 moles/L.

The counter electrode is an electrode working as a positive electrode in the photoelectrochemical cell. The counter electrode usually has the same meaning as the electrically conductive support described above, but in a construction which is likely to maintain a sufficient strength, a support is not necessarily required. A preferred structure of the counter electrode is a structure having a high charge collecting effect. At least one of the electrically conductive support and the counter electrode as mentioned above should be substantially transparent in order for light to reach the photoconductor layer. In the photoelectrochemical cell of the present invention, the electrically conductive support is preferably transparent to allow sunlight to inject from the support side. In this case, the counter electrode has further preferably properties of reflecting light. As the counter electrode of the photoelectrochemical cell, a glass or a plastic plate on which a metal or an electrically conductive oxide is deposited is preferable, and a glass plate on which platinum is deposited is particularly preferable. In the photoelectrochemical cell, a lateral side of the cell is preferably sealed with a polymer, an adhesive, or the like in order to prevent evaporation of the component. The characteristics of the thus obtained photoelectrochemical cell of the present invention are generally 0.01 to 1.5 V in open circuit voltage, 0.001 to 20 mA/cm$^2$ in short circuit current density, 0.1 to 0.9 in shape factor, and 0.001 to 25% in conversion efficiency, in an operation of 100 mW/cm$^2$ at AM 1.5 G.

EXAMPLES

Preparation of Exemplified Dyes (Preparation of Exemplified Compound D-1-1a)

The exemplified dye D-1-1a was prepared according to the method shown in the following scheme.

(i) Preparation of Compound d-1-2

To 70 mL of triethylamine and 50 mL of tetrahydrofuran, 25 g of Compound d-1-1, 33.8 g of Pd(dba), 8.6 g of triphenyl phosphine, 2.5 g of copper iodide, and 25.2 g of 1-heptyne were added. The resultant mixture was stirred at room temperature, and stirred at 80° C. for 4.5 hours. After concentration, purification was performed by means of column chromatography, and thus 26.4 g of Compound d-1-2 was obtained.

(ii) Preparation of Compound d-1-4

Under a nitrogen atmosphere at −15° C., 6.7 g of Compound d-1-3 was dissolved in 200 mL of THF (terahydrofuran), and LDA (lithium diisopropylamide) that was separately prepared was added dropwise in an amount of 2.5 equivalents of Compound d-1-3, and the resultant mixture was stirred for 75 minutes. Then, a solution in which 15 g of Compound d-1-2 was dissolved in 30 mL of THF was added dropwise, and the resultant mixture was stirred at 0° C. for 1 hour, and stirred at room temperature overnight. After concentration, 150 mL of water was added, and the resultant liquid was separated and extracted with 150 mL of methylene chloride, the resultant organic layer was washed with salt water, and the organic layer was concentrated. The crystal obtained was recrystallized with methanol, and then 18.9 g of Compound d-1-4 was obtained.

(iii) Preparation of Compound d-1-5

To 1,000 mL of toluene, 13.2 g of Compound d-1-4 and 1.7 g of PPTS (pyridinium para-toluenesulfonate) were added, and the resultant mixture was subjected to heating reflux for 5 hours under a nitrogen atmosphere. After concentration, the resultant liquid was separated with a saturated aqueous solution of sodium hydrogencarbonate and methylene chloride, and the resultant organic layer was concentrated. The crystal obtained was recrystallized with methanol and methylene chloride, and thus 11.7 g of Compound d-1-5 was obtained.

(iv) Preparation of Exemplified Dye D-1-1a

To 60 mL of DMF, 4.0 g of Compound d-1-5 and 2.2 g of Compound d-1-6 were added, and the resultant mixture was stirred at 70° C. for 4 hours. Then, 2.1 g of Compound d-1-7 was added, and the resultant mixture was stirred under heating at 160° C. for 3.5 hours. Then, 19.0 g of ammonium thiocyanate was added, and the resultant mixture was stirred at 130° C. for 5 hours. After concentration, 1.3 mL of water was added, the resultant mixture was filtered, and the resultant cake was washed with diethyl ether. A crude purified product was dissolved in a methanol solution together with TBAOH (tetrabutylammonium hydroxide) and purified by means of a Sephadex LH-20 column. A fraction in the main layer was recovered, and after concentration, a 0.2 M nitric acid solution was added, precipitates were filtered, washed with water and diethyl ether, and thus 600 mg of Compound D-1-1b was obtained. The purified product was dissolved in a methanol solution, and 1 M of nitric acid was added, precipitates were filtered, and then washed with water and diethyl ether, and thus 570 mg of Compound D-1-1a was obtained. Compound D-1-1b was treated with a TBAOH methanol solution, and then water was added, precipitates were filtered, and Compound D-1-1c was obtained as a residue.

The structure of Compound D-1-1a obtained was confirmed by NMR measurement and MS measurement.

$^1$H-NMR (DMSO-d$_6$, 400 MHz): δ (ppm) in aromatic regions: 9.37 (1H, d), 9.11 (1H, d), 9.04 (1H, s), 8.89 (2H), 8.74 (1H, s), 8.26 (1H, d), 8.10-7.98 (2H), 7.85-7.73 (2H), 7.60 (1H, d), 7.45-7.33 (2H), 7.33-7.12 (5H, m), 6.92 (1H, d)

MS-ESI m/z=1021.1 (M-H)$^+$

When Exemplified Dye D-1-1a obtained was prepared to be 8.5 μmol/L in the dye concentration with THF/water (=6:4, trifluoroacetic acid 0.1 v/v %) solvent and spectral absorption measurement was carried out, the absorption maximum wavelength was 568 nm.

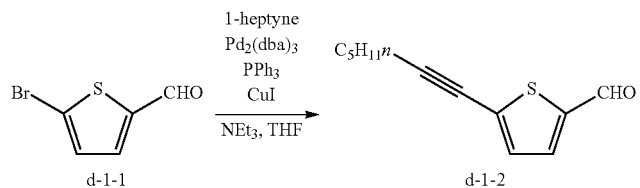

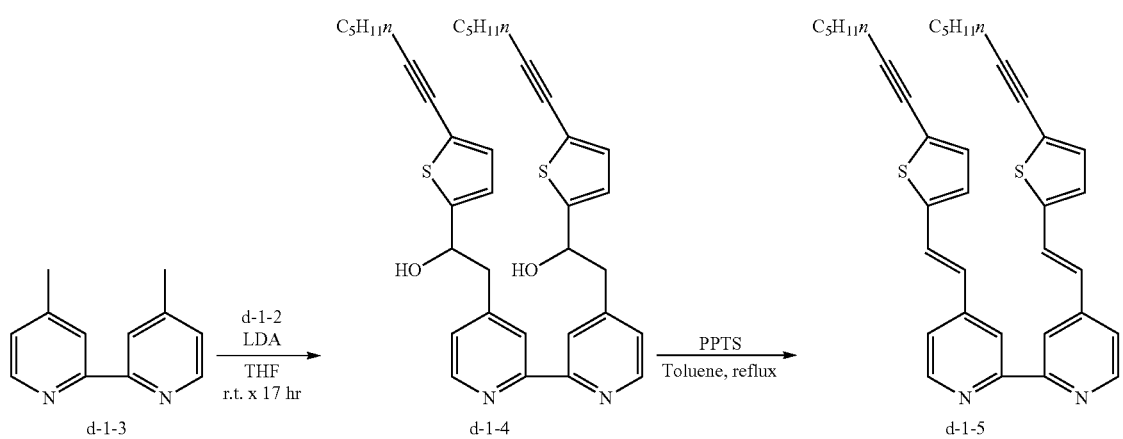

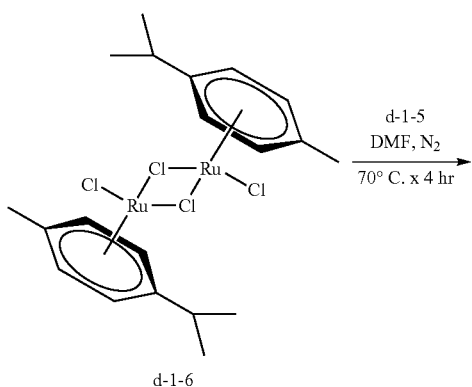

-continued
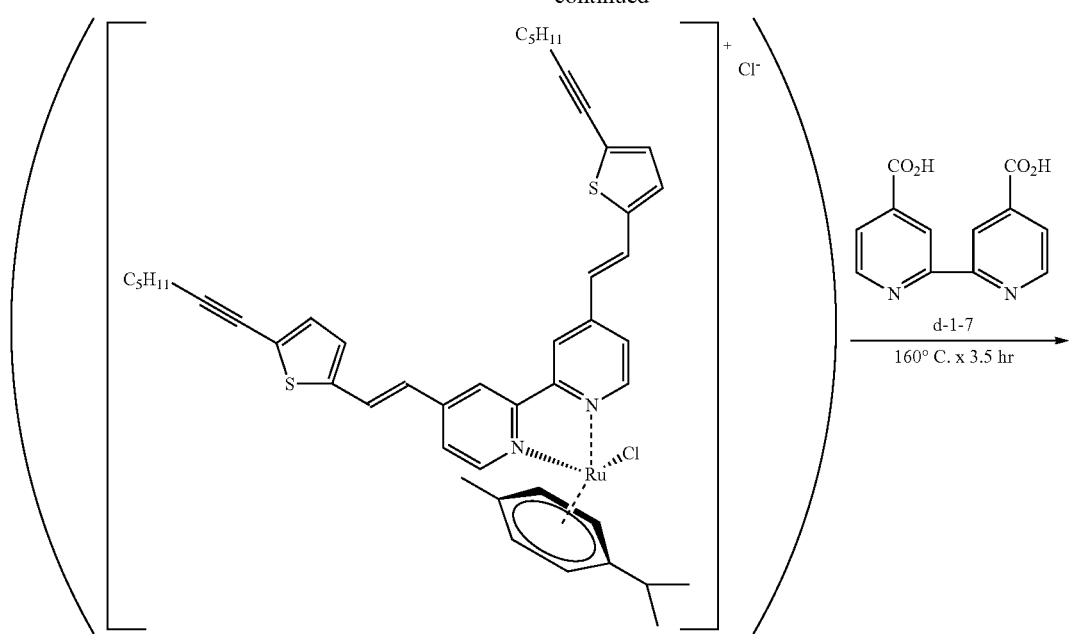
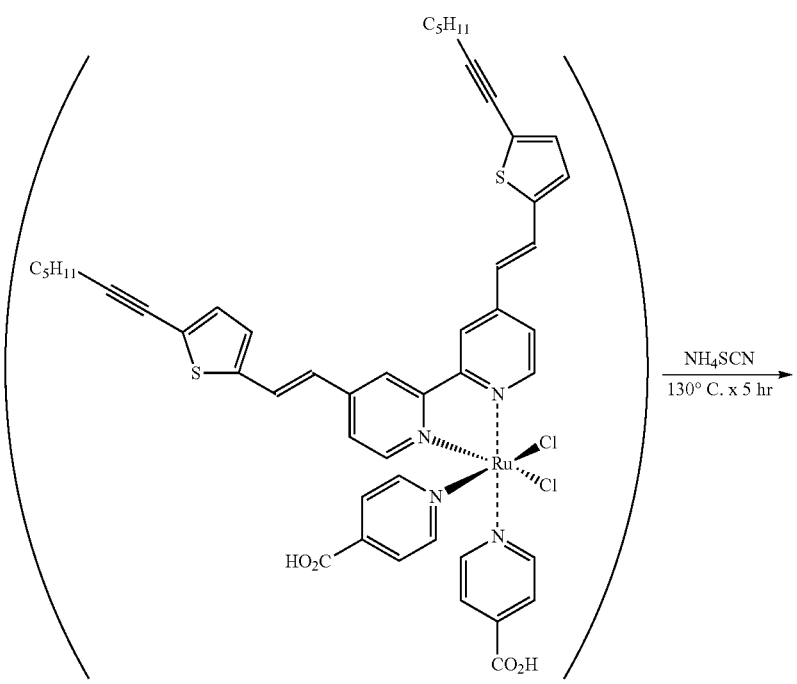

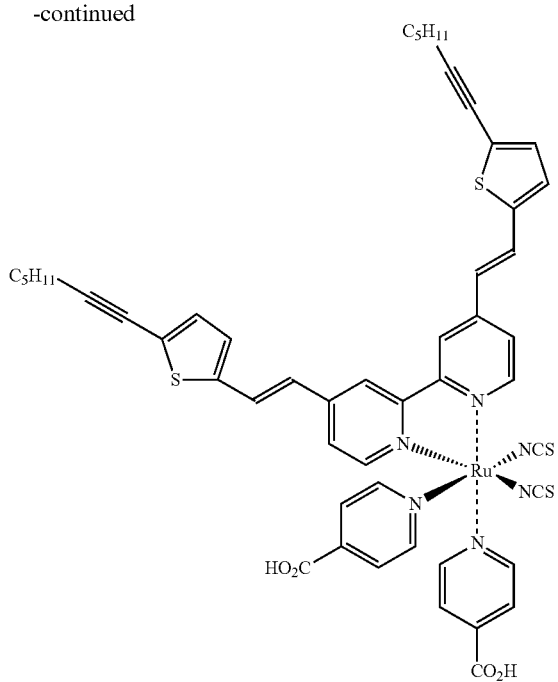

D-1-1a (Preparation of Exemplified Dye D-1-21a)

Compound d-2-4 was prepared according to the method shown in the following scheme, and Exemplified Dye D-1-21a was prepared in a manner similar to the exemplified dye D-1-1a.

The structure of Compound D-1-21a obtained was confirmed by MS measurement.

MS-ESI m/z=1125.2 (M-H)$^+$

When the exemplified dye obtained was prepared to be 8.5 μmol/L in the dye concentration with THF/water (=6:4, trifluoroacetic acid 0.1 v/v %) solvent and spectral absorption measurement was carried out, the absorption maximum wavelength was 570 nm.

(Preparation of Exemplified Dye D-1-16a)

Compound d-3-2 was prepared according to the method shown in the following scheme, and Exemplified Dye D-1-16a was prepared in a manner similar to Exemplified Dye D-1-1a.

The structure of Compound D-1-16a obtained was confirmed by MS measurement.

MS-ESI m/z=1315.4 (M-H)$^+$

When the exemplified dye obtained was prepared to be 8.5 μmol/L in the dye concentration with THF/water (=6:4, trifluoroacetic acid 0.1 v/v %) solvent and spectral absorption measurement was carried out, the absorption maximum wavelength was 574 nm.

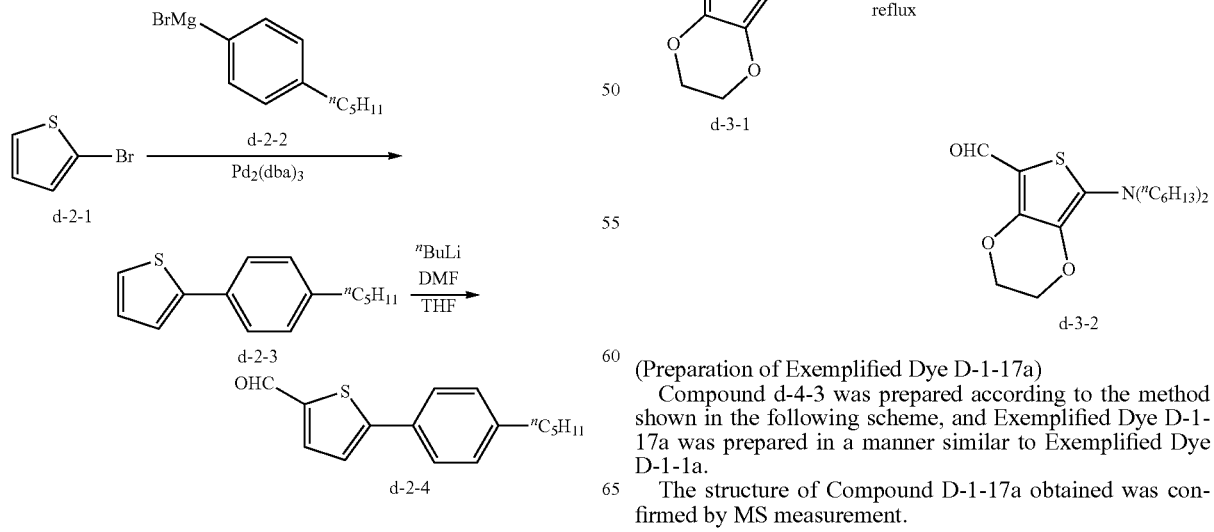

(Preparation of Exemplified Dye D-1-17a)

Compound d-4-3 was prepared according to the method shown in the following scheme, and Exemplified Dye D-1-17a was prepared in a manner similar to Exemplified Dye D-1-1a.

The structure of Compound D-1-17a obtained was confirmed by MS measurement.

MS-ESI m/z=1367.6 (M-H)$^+$

When the exemplified dye obtained was prepared to be 8.5 µmol/L in the dye concentration with THF/water (=6:4, trifluoroacetic acid 0.1 v/v %) solvent and spectral absorption measurement was carried out, the absorption maximum wavelength was 572 nm.

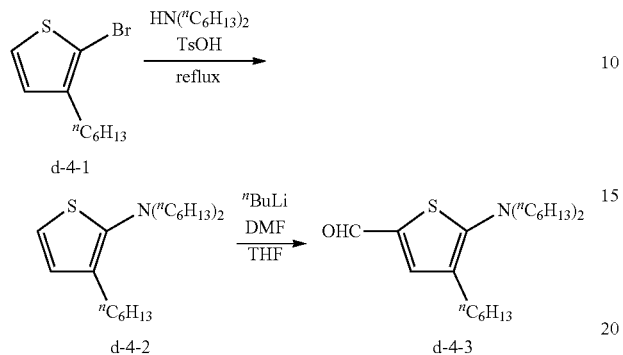

(Preparation of Exemplified Dye D-1-22a)

Compound d-5-6 was prepared according to the method shown in the following scheme, and Exemplified Dye D-1-22a was prepared in a manner similar to Exemplified Dye D-1-1a.

The structure of Compound D-1-22a obtained was confirmed by MS measurement.

MS-ESI m/z=1017.1 (M-H)+

When the exemplified dye obtained was prepared to be 8.5 µmol/L in the dye concentration with THF/water (=6:4, trifluoroacetic acid 0.1 v/v %) solvent and spectral absorption measurement was carried out, the absorption maximum wavelength was 570 nm.

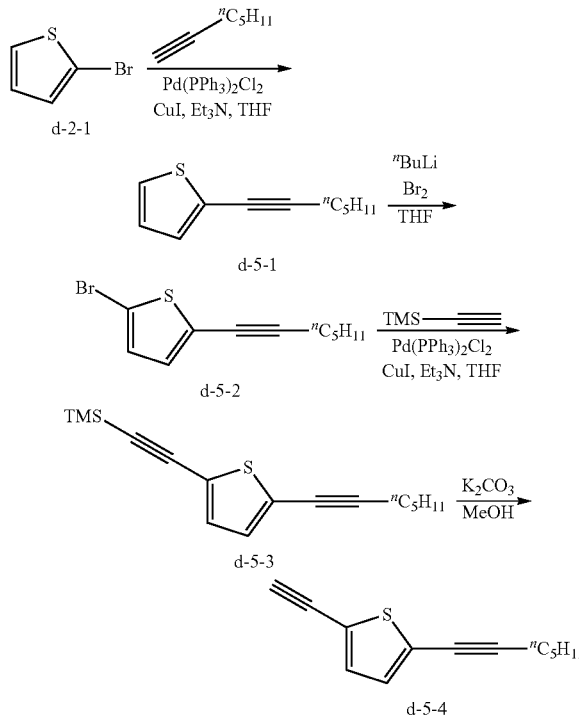

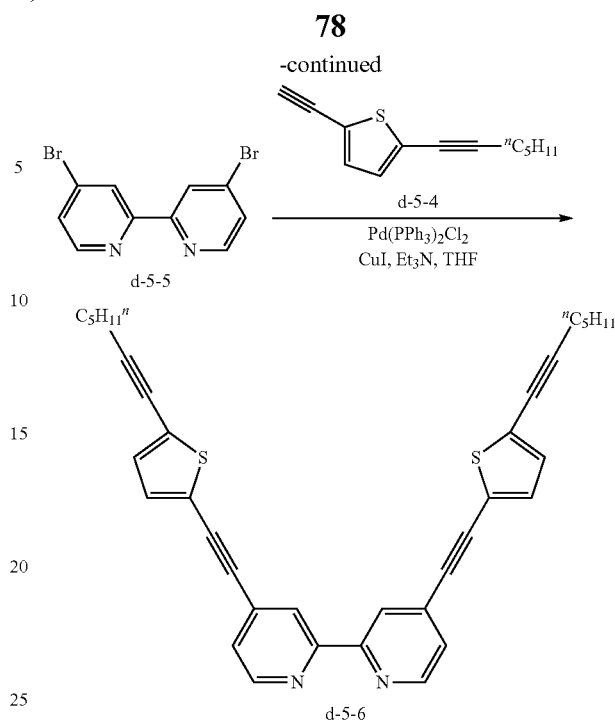

(Preparation of Exemplified Dye D-1-23a)

Compound d-6-3 was prepared according to the method shown in the following scheme, and Exemplified Dye D-1-23a was prepared in a manner similar to Exemplified Dye D-1-1a.

The structure of Compound D-1-23a obtained was confirmed by MS measurement.

MS-ESI m/z=1121.2 (M-H)+

When Exemplified Dye obtained was prepared to be 8.5 µmol/L in the dye concentration with THF/water (=6:4, trifluoroacetic acid 0.1 v/v %) solvent and spectral absorption measurement was carried out, the absorption maximum wavelength was 571 nm.

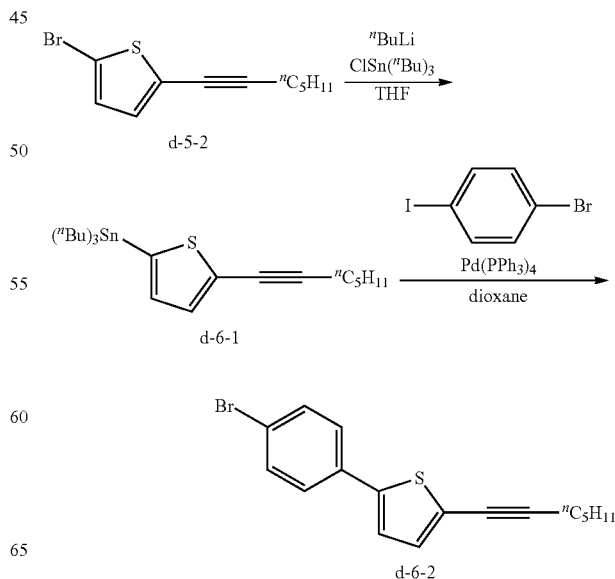

-continued

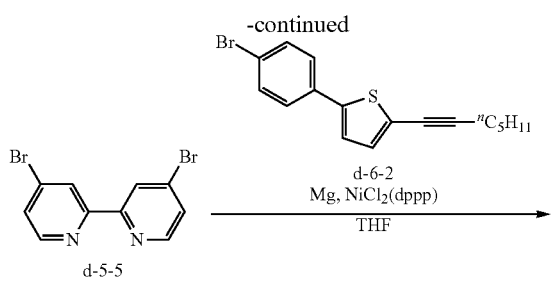

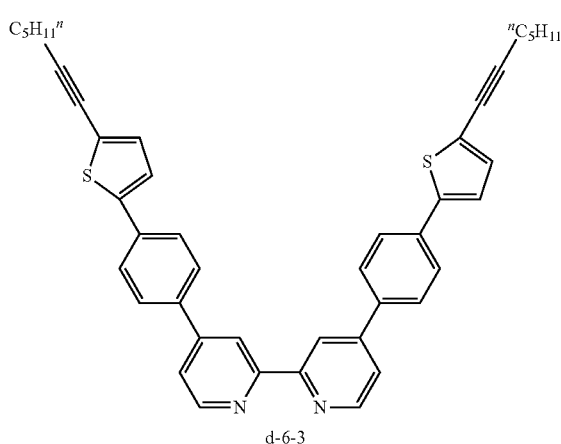

(Preparation of Exemplified Dye D-1-24a)

Exemplified Dye D-1-24a was prepared in a manner similar to Exemplified Dye D-1-21a, except that the compound d-7-1 was used in place of Compound d-2-2.

The structure of Compound D-1-24a obtained was confirmed by MS measurement.

MS-ESI m/z=1041.1 (M-H)$^+$

When Exemplified Dye D-1-24a obtained was prepared to be 8.5 μmol/L in the dye concentration with THF/water (=6:4, trifluoroacetic acid 0.1 v/v %) solvent and spectral absorption measurement was carried out, the absorption maximum wavelength was 570 nm.

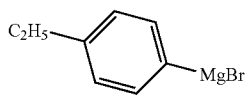

(Preparation of Exemplified Dye D-9-1a)

Exemplified Dye D-9-1a was prepared in a manner similar to Exemplified Dye D-1-1a, except that the compound d-8-1 was used in place of Compound d-1-7.

The structure of Compound D-9-1a obtained was confirmed by MS measurement.

MS-ESI m/z=1021.1 (M-H)$^+$

When the exemplified dye obtained was prepared to be 8.5 μmol/L in the dye concentration with THF/water (=6:4, trifluoroacetic acid 0.1 v/v %) solvent and spectral absorption measurement was carried out, the absorption maximum wavelength was 566 nm.

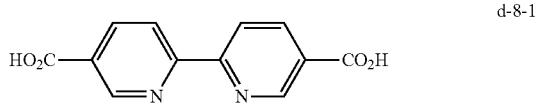 [SMILES: O=C(O)c1ccc(-c2ccc(C(=O)O)cn2)nc1]

(Preparation of Exemplified Dye D-1-8a)

Exemplified Dye D-1-8a was prepared in a manner similar to Exemplified Dye D-1-1a, except that the compound d-9-2 was used in place of Compound d-1-2.

The structure of Compound D-1-8a obtained was confirmed by MS measurement.

MS-ESI m/z=989.2 (M-H)$^+$

When the exemplified dye obtained was prepared to be 8.5 μmol/L in the dye concentration with THF/water (=6:4, trifluoroacetic acid 0.1 v/v %) solvent and spectral absorption measurement was carried out, the absorption maximum wavelength was 565 nm.

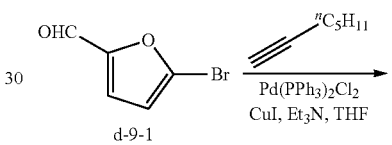

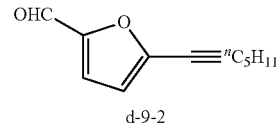

(Preparation of Exemplified Dye D-2-8)

Exemplified Dye D-2-8 was prepared in a manner similar to the above-described Exemplified Dye D-1-1a, except that trifluoroacetylacetone and cesium carbonate were used in place of ammonium thiocyanate, and after the reaction, a crude purified product was purified by means of a Sephadex LH-20 column, and then treated with a 0.2N nitric acid solution, and filtered, and then a residue was suspended in a concentrated ammonia aqueous solution.

The structure of Compound D-2-8 obtained was confirmed by MS measurement.

MS-ESI m/z=914.9 (M-H)$^+$

When the exemplified dye obtained was prepared to be 8.5 μmol/L in the dye concentration with THF/water (=6:4, trifluoroacetic acid 0.1 v/v %) solvent and spectral absorption measurement was carried out, the absorption maximum wavelength was 562 nm.

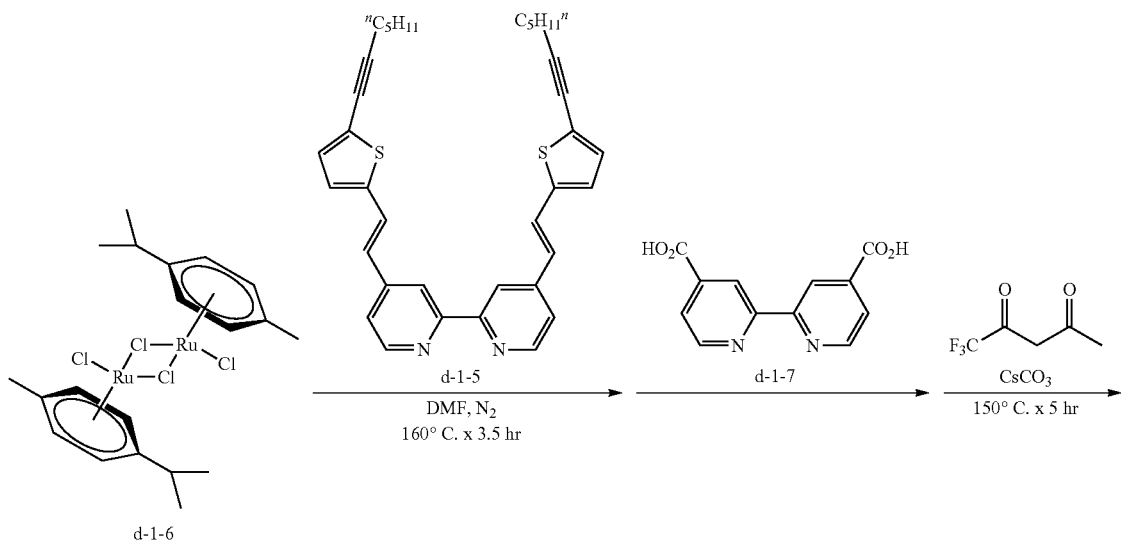

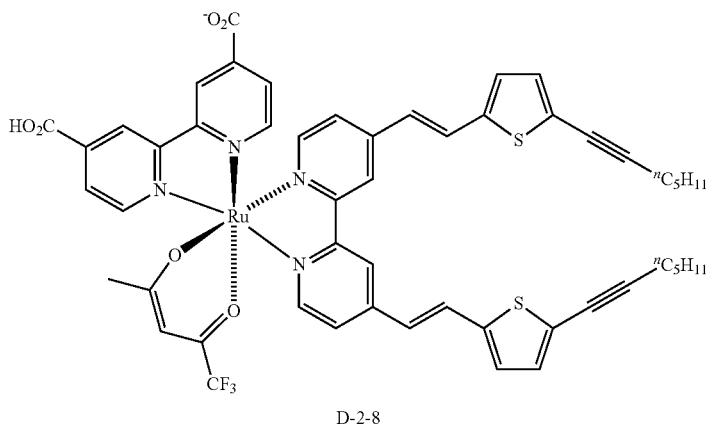

(Preparation of Exemplified Dye D-7-1)
(i) Preparation of Compound d-10-2

To 250 mL of ethylene glycol, 5.0 g of Compound d-10-1 and 1 equivalent of Compound d-1-5 thereto were added, and the resultant mixture was subjected to heating reflux for 1 hour under a nitrogen atmosphere and light-shielded conditions. Then, 1 equivalent of Compound d-1-7 was added, and the resultant mixture was superheated at 130° C. for 2 hours. Then, the resultant organic layer was washed with 250 mL of a saturated aqueous solution of sodium hyposulfite, and filtered. The resultant cake was washed with 100 mL of water and 100 mL of diethyl ether. After drying, 8.2 g of Compound d-10-2 was obtained.

(ii) Preparation of Exemplified Dye D-7-1

To 270 mL of DMF and 135 mL of water, 4.2 g of Compound d-10-2 and 36.4 g of ammonium thiocyanate were added, and the resultant mixture was stirred at 140° C. for 3 hours. After concentration, the resultant mixture was cooled to 3° C., 10 mL of water was added, the resultant mixture was filtered, and a cake was washed with diethyl ether. A crude purified product was dissolved in a methanol solution together with TBAOH (tetrabutylammonium hydroxide), and purified by means of a SephadexLH-20 column. A fraction in the main layer was recovered, and after concentration, 0.2 M of nitric acid was added, precipitates were filtered, washed with water and diethyl ether. The resultant precipitates were dissolved in a methanol solution again, 1M of nitric acid was added, precipitates were filtered, and then washed with water and diethyl ether, and thus 3.4 g of Compound D-7-1 was obtained.

The structure of Compound D-7-1 obtained was confirmed by MS measurement.

MS-ESI m/z: 1111.2 (M-H)$^+$

When the exemplified dye obtained was prepared to be 8.5 μmol/L in the dye concentration with THF/water (=6:4, trifluoroacetic acid 0.1 v/v %) solvent and spectral absorption measurement was carried out, the absorption maximum wavelength was 610 nm.

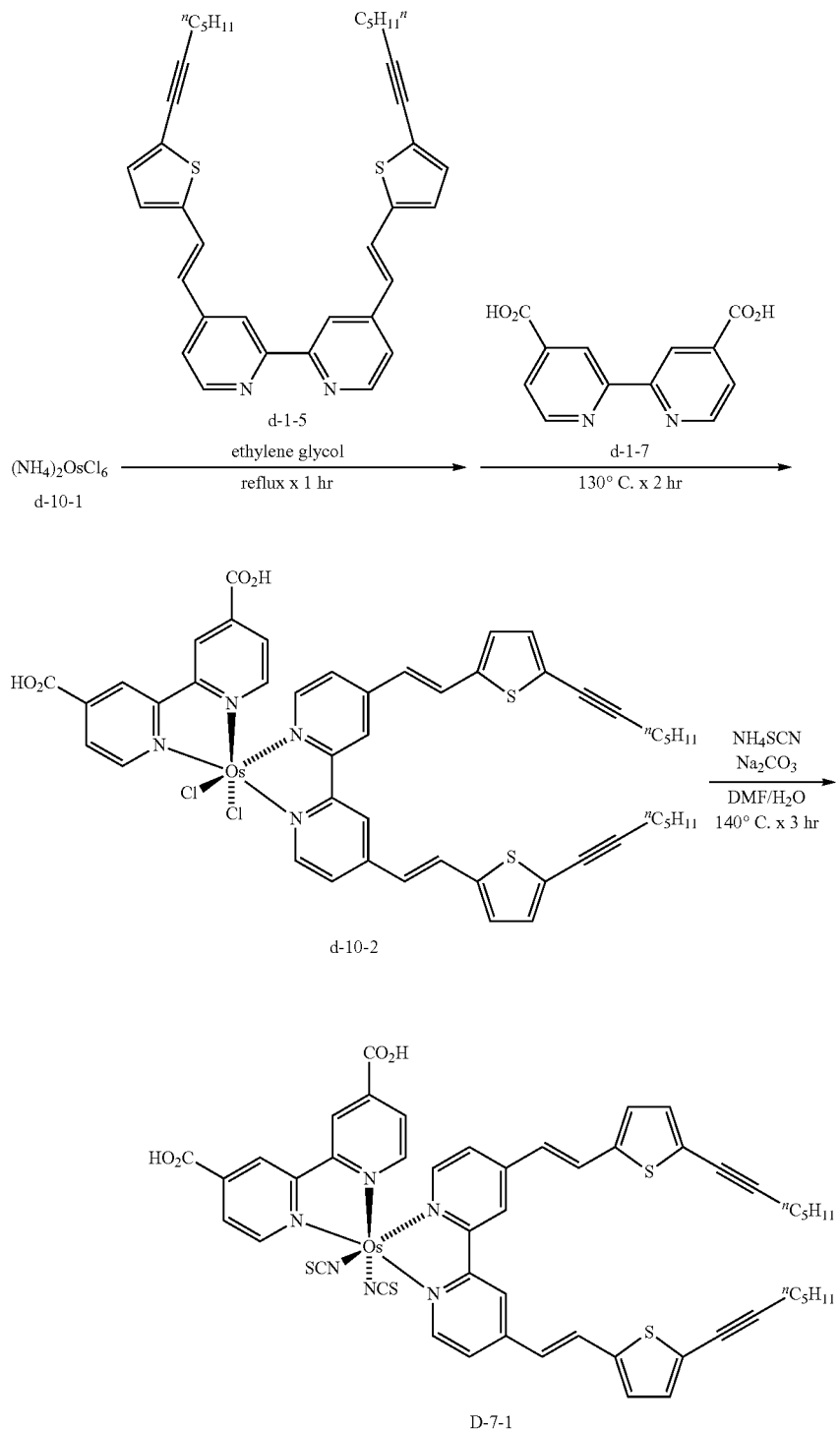

(Preparation of Exemplified Dye D-8-1a)

Exemplified Dye D-8-1a was prepared according to the method shown in the following scheme in a manner similar to Exemplified Dye D-1-1a.

When the exemplified dye D-8-1a obtained was prepared to be 8.5 μmol/L in the dye concentration with THF/water (=6:4, trifluoroacetic acid 0.1 v/v %) solvent and spectral absorption measurement was carried out, the absorption maximum wavelength was 580 nm.

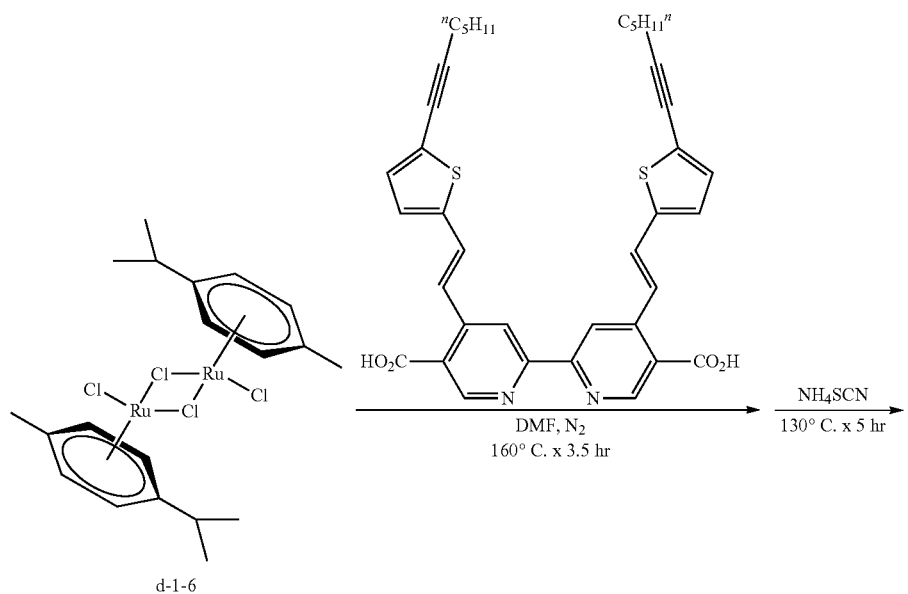
d-1-6
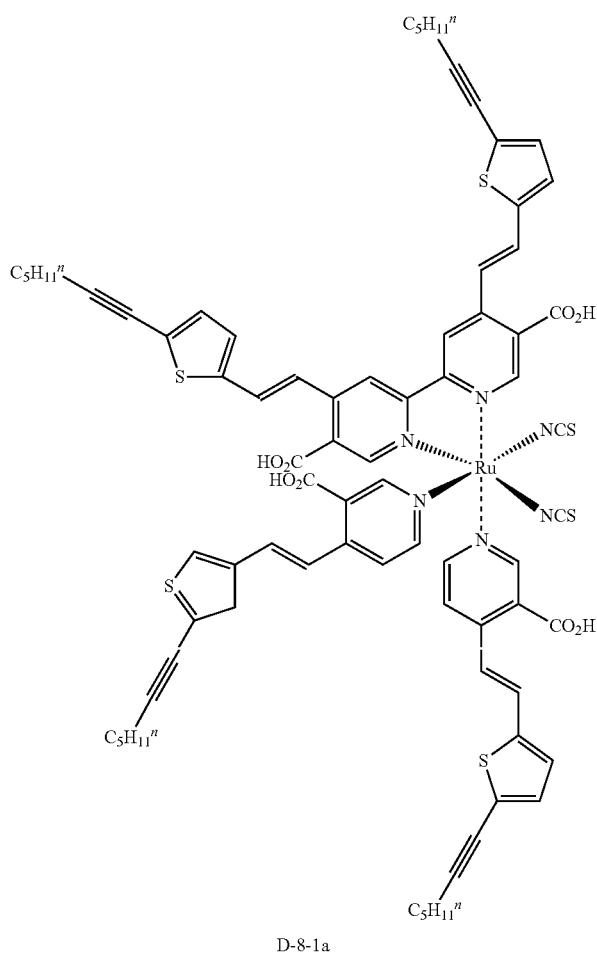
D-8-1a
The metal complex dyes prepared by the above-described methods contains the ones shown below and ones in which counter anions thereof each are a tetrabuthylammonium ion.

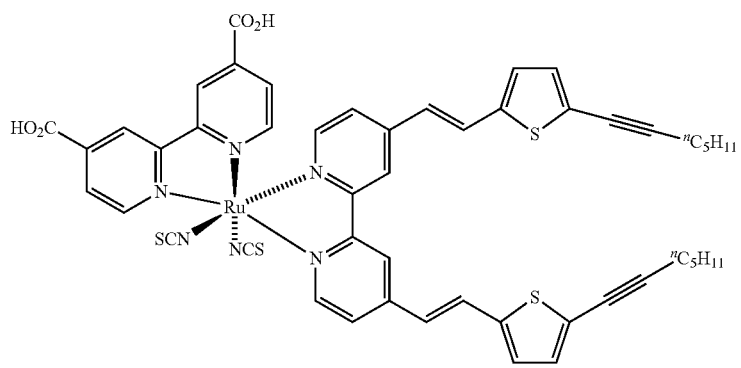
D-1-1a
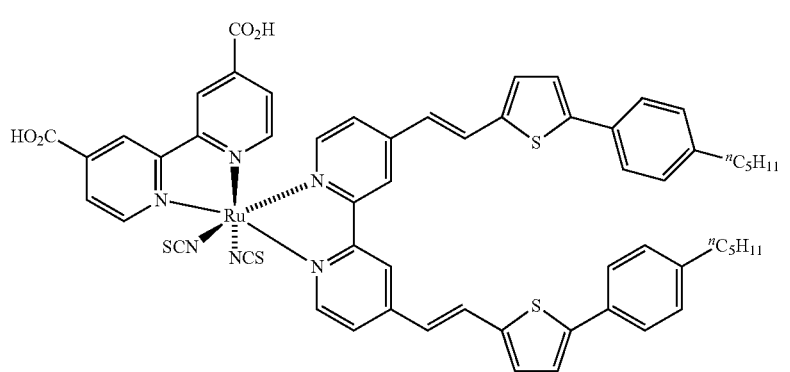
D-1-21a
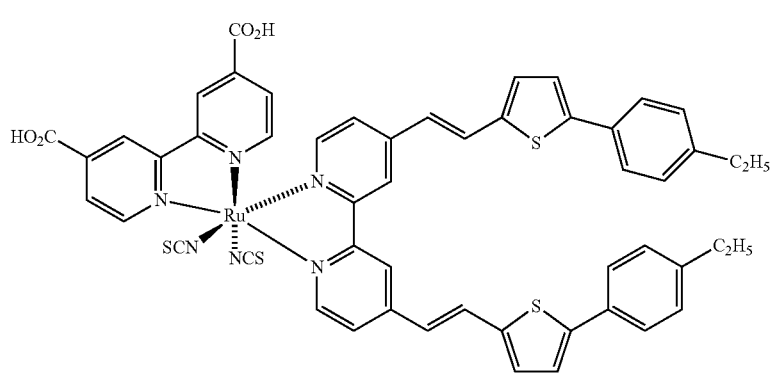
D-1-24a
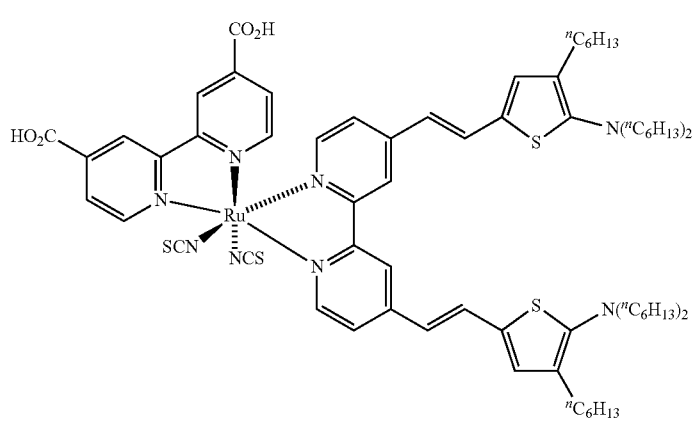
D-1-17a

-continued
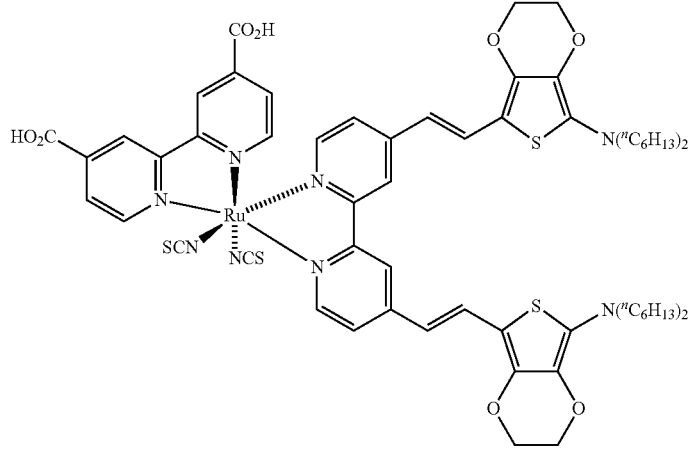
D-1-16a
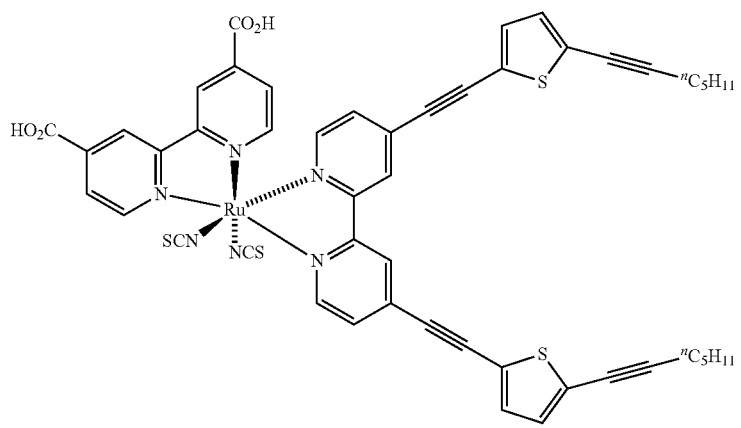
D-1-22a
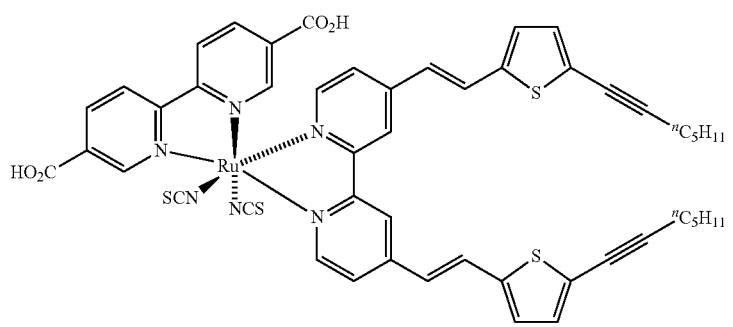
D-9-1a

-continued
D-1-8a
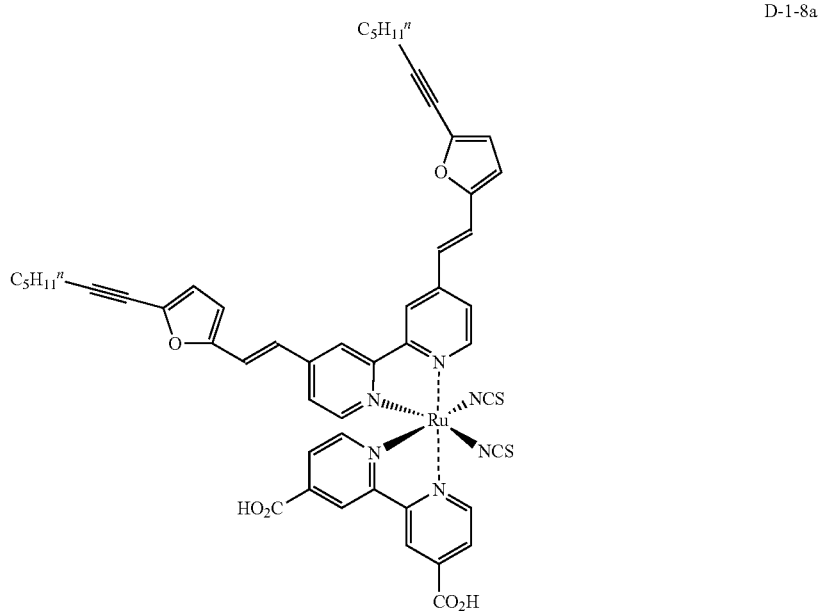
D-7-1
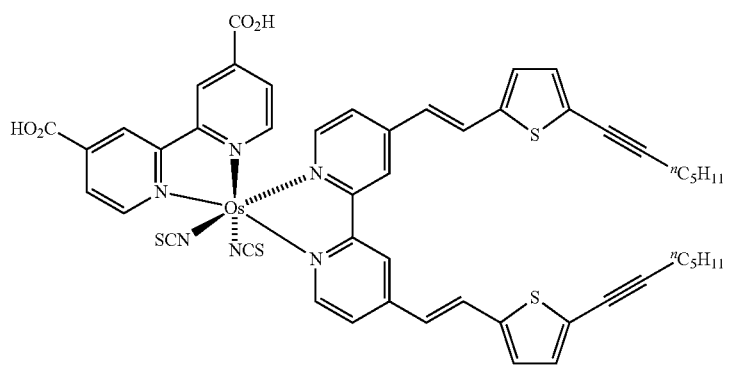
D-1-23a
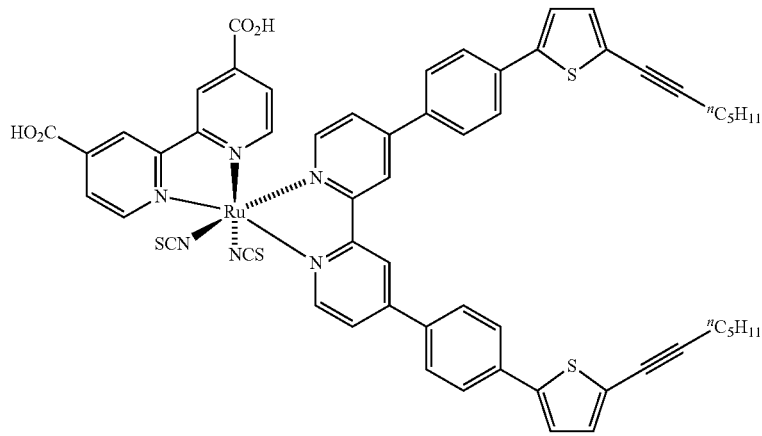

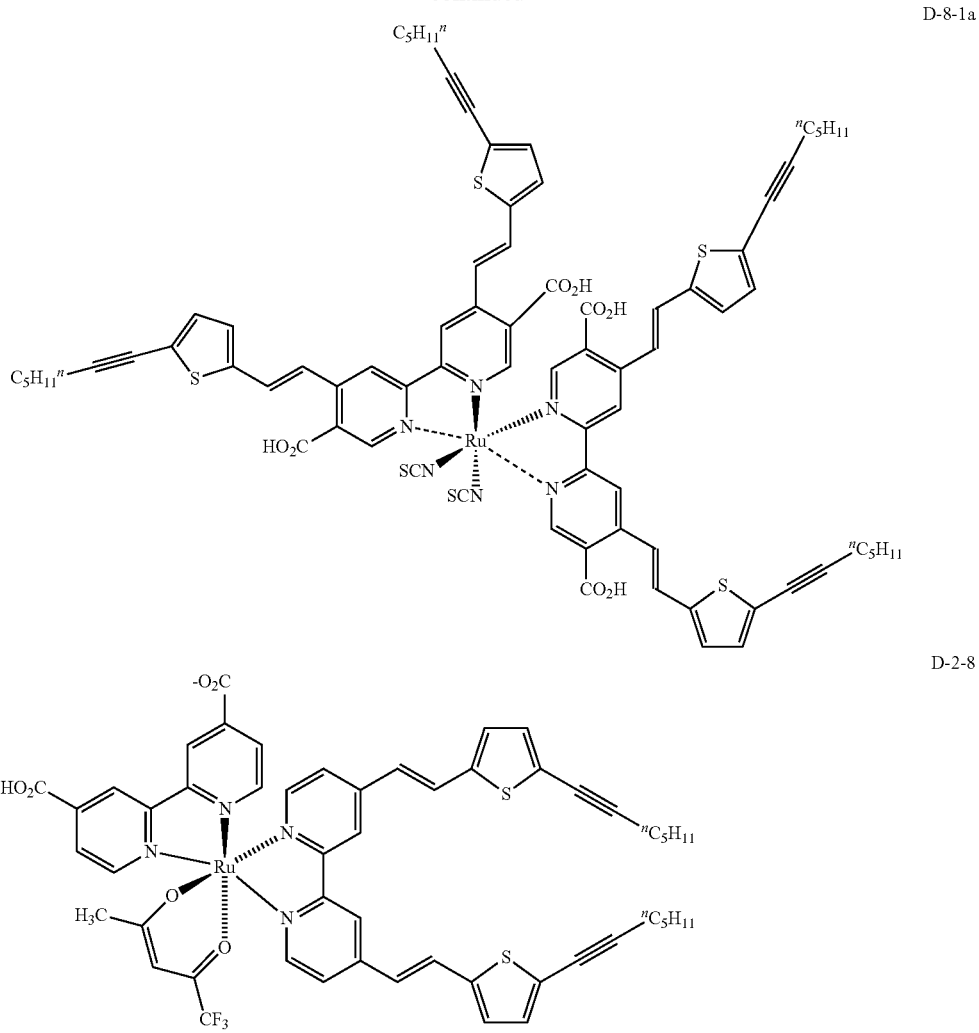

Experiment 1

Production of Photoelectric Conversion Element

On a glass substrate, a film of tin oxide doped with fluorine was formed by sputtering as a transparent conductive film, and this film was scribed with a laser to partition the transparent conductive film into two parts. Anatase type titanium oxide particles (average particle size: 50 nm) were sintered on one part of the electrically conductive films, and thus a light-receiving electrode was prepared. Thereafter, a dispersion liquid containing silica particles and rutile type titanium oxide at a ratio of 40:60 (mass ratio) was prepared, and this dispersion liquid was applied on the light-receiving electrode described above and sintered. Thus, an insulating porous body was formed. Subsequently, a carbon electrode was formed as a counter electrode.

Next, the glass substrate having the insulating porous body formed thereon was immersed for 48 hours in an ethanol solution of each of the sensitizing dyes indicated in the following Table 1 ($3 \times 10^{-4}$ mol/L). The glass dyed with the sensitizing dye was immersed for 30 minutes in a 10% ethanol solution of 4-tert-butylpyridine, and then the glass was washed with ethanol and naturally dried. The photosensitive layer thus obtained had a thickness of 10 μm, and the application amount of the semiconductor fine particles was 20 g/m². The application amount of the sensitizing dye was appropriately selected from the range of 0.1 to 10 mmol/m² according to types of sensitizing dyes.

For an electrolytic liquid, a methoxypropionitrile solution of dimethylpropylimidazolium iodide (0.5 mol/L) and iodine (0.1 mol/L) was used.

(Measurement of Photoelectric Conversion Efficiency)

Pseudo-sunlight which did not include ultraviolet radiation was generated by passing the light of a 500-W xenon lamp (manufactured by Ushio, Inc.) through an AM1.5G filter (manufactured by Oriel Instruments Corp.) and a sharp cutoff filter (Kenko L-42, trade name). The intensity of this light was 89 mW/cm². The produced photoelectric conversion element was irradiated with this light, and the electricity thus generated was measured with a current-voltage measurement device (Keithley-238 type, trade name). The results of measuring the conversion efficiencies of the dye-sensitized solar cells thus determined are presented in the following Table 1. The results were evaluated such that one having a conversion efficiency of 7.5% or more was rated as "⊙"; one having a conversion efficiency of equal to or more than 7.0% and less than 7.5% was rated as "○"; one having a conversion efficiency of equal to or more than 6.7% and less than 7.0% was rated as "●"; one having a conversion efficiency of equal to or more than 6.5% and less than 6.7% was rated as "Δ"; and one having a conversion efficiency of less than 6.5% was rated as "x". One having a conversion efficiency equal to or more than 6.7% was deemed to be passable.

TABLE 1

| Sample No. | Metal complex dye | Conversion efficiency (%) | Remarks |
|---|---|---|---|
| 1-1 | D-1-1a | ⊙ | This invention |
| 1-2 | D-1-1b | ⊙ | This invention |
| 1-3 | D-1-21a | ⊙ | This invention |
| 1-4 | D-1-21b | ⊙ | This invention |
| 1-5 | D-1-24a | ⊙ | This invention |
| 1-6 | D-1-24b | ⊙ | This invention |
| 1-7 | D-1-17a | ⊙ | This invention |
| 1-8 | D-1-17b | ⊙ | This invention |
| 1-9 | D-1-16a | ⊙ | This invention |
| 1-10 | D-1-16b | ⊙ | This invention |
| 1-11 | D-1-22a | ○ | This invention |
| 1-12 | D-9-1a | ○ | This invention |
| 1-13 | D-1-8a | ○ | This invention |
| 1-14 | D-7-1 | ● | This invention |
| 1-15 | D-1-23a | ● | This invention |
| 1-16 | D-8-1a | ● | This invention |
| 1-17 | Sensitizing dye A | X | Comparative example |
| 1-18 | Sensitizing dye B | X | Comparative example |
| 1-19 | Sensitizing dye C | Δ | Comparative example |
| 1-20 | Sensitizing dye D | X | Comparative example |
| 1-21 | Sensitizing dye E | X | Comparative example |

As the comparative metal complex dye, the following sensitizing dyes A to E were used.

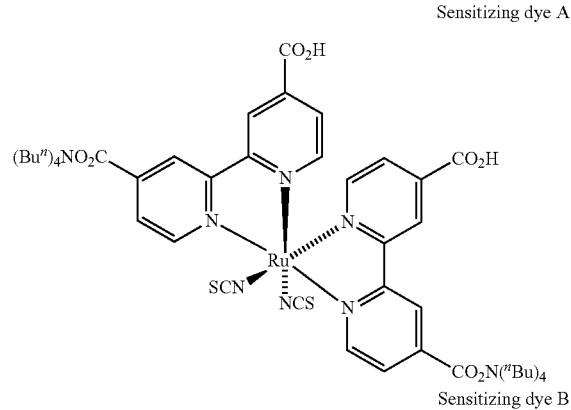

Sensitizing dye A

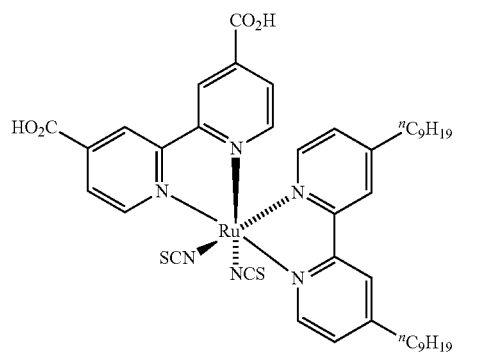

Sensitizing dye B

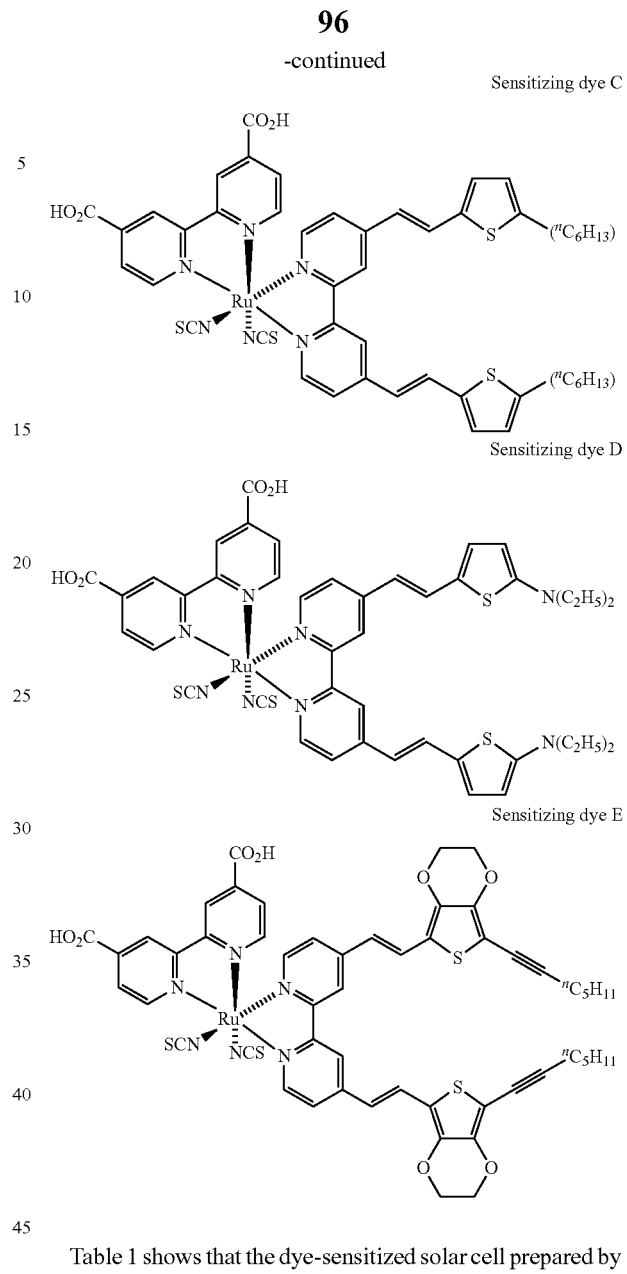

Table 1 shows that the dye-sensitized solar cell prepared by using the metal complex dye of the present invention had a passable level of the conversion efficiency. To the contrary, when the comparative dye was used, the conversion efficiency was low.

Experiment 2

1. Preparation of Raw Material Compound Solution for ITO Film

Were dissolved 5.58 g of indium(III) chloride tetrahydrate and 0.23 g of tin(II) chloride dihydrate in 100 mL of ethanol, and thus a raw material compound solution for ITO film was prepared.

2. Preparation of Raw Material Compound Solution for FTO Film

Was dissolved 0.701 g of tin(IV) chloride pentahydrate in 10 mL of ethanol, and 0.592 g of a saturated aqueous solution of ammonium fluoride was added thereto. This mixture was completely dissolved in an ultrasonic bath over about 20 minutes, and thus a raw material compound solution for FTO film was prepared.

Then, the surface of a heat resistant glass plate having a thickness of 2 mm was subjected to chemical cleaning and was dried. Subsequently, this glass plate was placed in a reactor and was heated with a heater. When the heating temperature of the heater reached 450° C., the raw material compound solution for ITO film obtained was sprayed over the glass plate for 25 minutes through a nozzle having an aperture diameter of 0.3 mm at a pressure of 0.06 MPa with a distance to the glass plate of 400 mm.

After this raw material compound solution for ITO film was sprayed, the glass plate was left to stand for two minutes (during this time period, ethanol was continuously sprayed on the glass substrate surface so as to suppress an increase in the substrate surface temperature), and when the heating temperature of the heater reached 530° C., the raw material compound solution for FTO film obtained was sprayed thereon under the same conditions for 2 minutes and 30 seconds. Thus, there was obtained a transparent electrode plate in which an ITO film having a thickness of 530 nm and an FTO film having a thickness of 170 nm were sequentially formed on a heat resistant glass plate.

For a comparison, a transparent electrode plate having only an ITO film having a thickness of 530 nm formed on a heat resistant glass plate having a thickness of 2 mm, and a transparent electrode plate having only an FTO film having a thickness of 180 nm formed in the same manner were respectively produced.

These three kinds of transparent electrode plates were heated in a heating furnace at 450° C. for 2 hours.

Subsequently, dye-sensitized solar cells having a structure such as shown in FIG. 2 of Japanese Patent No. 4260494 were produced using the three kinds of transparent electrode plates. The formation of an oxide semiconductor porous film 15 was carried out by dispersing titanium oxide fine particles having an average particle size of about 230 nm in acetonitrile to prepare a paste, applying this paste on a transparent electrode 11 by a bar coating method to a thickness of 15 μm, drying the paste, and then calcining the paste at 450° C. for one hour. The dyes indicated in Table 2 were loaded in this oxide semiconductor porous film 15.

Furthermore, a conductive substrate produced by laminating an ITO film and an FTO film on a glass plate was used for the counter electrode 16, and an electrolytic liquid formed from a non-aqueous solution of iodine/iodide was used in the electrolyte layer 17. The plane dimension of the dye-sensitized solar cell was 25 mm×25 mm.

(Measurement of Photoelectric Conversion Efficiency)

Pseudo-sunlight which did not include ultraviolet radiation was generated by passing the light of a 500-W xenon lamp (manufactured by Ushio, Inc.) through an AM1.5G filter (manufactured by Oriel Instruments Corp.) and a sharp cutoff filter (Kenko L-42, trade name). The intensity of this light was 89 mW/cm². The produced photoelectric conversion element was irradiated with this light, and the electricity thus generated was measured with a current-voltage measurement device (Keithley-238 type, trade name). The results of measuring the conversion efficiencies of the dye-sensitized solar cells thus determined are presented in the following Table 2. The results were evaluated such that one having a conversion efficiency of 7.5% or more was rated as "⊙"; one having a conversion efficiency of equal to or more than 7.0% and less than 7.5% was rated as "○"; one having a conversion efficiency of equal to or more than 6.7% and less than 7.0% was rated as "●"; one having a conversion efficiency of equal to or more than 6.5% and less than 6.7% was rated as "Δ"; and one having a conversion efficiency of less than 6.5% was rated as "×". One having a conversion efficiency equal to or more than 6.7% was deemed to be passable.

TABLE 2

| Sample No. | TCO | Metal complex dye | Conversion efficiency (%) | Remarks |
|---|---|---|---|---|
| 2-1 | ITO only | D-1-1a | ○ | This invention |
| 2-2 | FTO only | D-1-1a | ⊙ | This invention |
| 2-3 | ITO + FTO | D-1-1a | ⊙ | This invention |
| 2-4 | ITO only | D-1-21a | ○ | This invention |
| 2-5 | FTO only | D-1-21a | ○ | This invention |
| 2-6 | ITO + FTO | D-1-21a | ⊙ | This invention |
| 2-7 | ITO only | D-1-16a | ○ | This invention |
| 2-8 | FTO only | D-1-16a | ○ | This invention |
| 2-9 | ITO + FTO | D-1-16a | ⊙ | This invention |
| 2-10 | ITO only | D-1-17a | ○ | This invention |
| 2-11 | FTO only | D-1-17a | ○ | This invention |
| 2-12 | ITO + FTO | D-1-17a | ⊙ | This invention |
| 2-13 | ITO only | D-1-22a | ● | This invention |
| 2-14 | FTO only | D-1-22a | ○ | This invention |
| 2-15 | ITO + FTO | D-1-22a | ⊙ | This invention |
| 2-16 | ITO only | D-1-23a | ● | This invention |
| 2-17 | FTO only | D-1-23a | ○ | This invention |
| 2-18 | ITO + FTO | D-1-23a | ⊙ | This invention |
| 2-19 | ITO only | D-8-1a | ● | This invention |
| 2-20 | FTO only | D-8-1a | ○ | This invention |
| 2-21 | ITO + FTO | D-8-1a | ○ | This invention |
| 2-22 | ITO only | Sensitizing dye A | X | Comparative example |
| 2-23 | FTO only | Sensitizing dye A | X | Comparative example |
| 2-24 | ITO + FTO | Sensitizing dye A | Δ | Comparative example |
| 2-25 | ITO only | Sensitizing dye B | X | Comparative example |
| 2-26 | FTO only | Sensitizing dye B | X | Comparative example |
| 2-27 | ITO + FTO | Sensitizing dye B | X | Comparative example |
| 2-28 | ITO only | Sensitizing dye C | Δ | Comparative example |
| 2-29 | FTO only | Sensitizing dye C | X | Comparative example |
| 2-30 | ITO + FTO | Sensitizing dye C | Δ | Comparative example |

Table 2 shows that the conversion efficiency decreased even with the dye-sensitized solar cell of the present invention, when the electrically conductive layer was composed of only an ITO film or only a FTO film, and the conversion efficiency showed an increasing tendency, when the FTO film was formed on the ITO film as the electrically conductive layer. The tendency was similar also in the case of the dye-sensitized solar cell according to the comparative examples. In particular, the dye-sensitized solar cell in which the FTO film was formed on the ITO film as the electrically conductive layer showed a conversion efficiency as high as 7.5% or more. Whereas, the conversion efficiency of the dye-sensitized solar cells according to the comparative examples showed a lower value, as compared with the case of the present invention.

Experiment 3

According to the following methods, test cells (i) and (iv) of dye-sensitized solar cells having different structures were prepared, and the photoelectric conversion characteristics were measured and the conversion efficiency was determined on these test cells.

(Test Cell (i))

Grooves with a depth of 5 μm were formed on the surface of a FTO film-attached glass plate having a size of 100 mm×100 mm in the form of a lattice circuit pattern by an etching method. A pattern was formed by photolithography, and then etching was performed using hydrofluoric acid. A metal conductive layer (seed layer) was formed thereon by a sputtering method for the purpose of enabling plating formation, and a metal wiring layer 3 was further formed thereon by additive plating. The metal wiring layer 3 was formed in a convex lens shape to a height of 3 µm from the surface of the transparent substrate 2. The circuit width was set to 60 µm. An FTO film was formed over the metal wiring layer 3 by a SPD method to a thickness of 400 nm as a shielding layer 5, and the final assembly was used as an electrode substrate (i). The cross-sectional shape of the electrode substrate (i) was as shown in FIG. 2 of JP-A-2004-146425.

A dispersion liquid of titanium oxide having an average particle size of 25 nm was applied and dried on the electrode substrate (i), and the electrode substrate was heated and sintered at 450° C. for one hour. The electrode substrate was immersed into each of the ethanol solutions of the dyes of the present invention for forty minutes, and the dye was carried thereon. The electrode substrate and a platinum sputtered FTO substrate were arranged to face each other, with a thermoplastic polyolefin resin sheet having a thickness of 50 µm interposed therebetween, and the resin sheet portion was melted by heating to fix the two electrode substrates. A methoxyacetonitrile solution containing an iodide salt at 0.5 M and iodine at 0.05 M as main components was injected through an injection port for electrolytic liquid, which had been kept open in advance on the platinum sputtered electrode side, and the methoxyacetonitrile solution was filled in between the electrodes. Furthermore, the peripheral areas and the electrolytic liquid injection port were fully sealed using an epoxy-based sealing resin, and a silver paste was applied on the collecting terminal portions. Thus, a test cell (i) was prepared. The photoelectric conversion characteristics of the test cell (i) were evaluated by using pseudo-sunlight of AM1.5. The results are presented in Table 3.

(Test Cell (iv))

A metal wiring layer 3 (gold circuit) was formed on an FTO film-attached glass substrate having a size of 100×100 mm by an additive plating method. The metal wiring layer 3 (gold circuit) was formed in a lattice form on the substrate surface, and the metal wiring layer had a circuit width of 50 µm and a circuit thickness of 5 µm. An FTO film having a thickness of 300 nm was formed on this surface by an SPD method as a shielding layer 5, and thus the final assembly was used as a test cell (iv). The cross-section of the electrode substrate (iv) was examined using SEM-EDX, and there was slippage which was thought to be attributable to the footing of the plating resist at the wiring bottom, while FTO coating was not provided on shaded areas.

A test cell (iv) was produced using the electrode substrate (iv). The photoelectric conversion characteristics of the test cell (iv) were evaluated by using pseudo-sunlight of AM1.5. The results are presented in Table 3. The results were evaluated such that one having a conversion efficiency of 7.5% or more was rated as "⊙"; one having a conversion efficiency of equal to or more than 7.0% and less than 7.5% was rated as "○"; one having a conversion efficiency of equal to or more than 6.7% and less than 7.0% was rated as "●"; one having a conversion efficiency of equal to or more than 6.5% and less than 6.7% was rated as "Δ"; and one having a conversion efficiency of less than 6.5% was rated as "x". One having a conversion efficiency equal to or more than 6.7% was deemed to be passable.

TABLE 3

| Sample No. | Test cell | Metal complex dye | Conversion efficiency (%) | Remarks |
|---|---|---|---|---|
| 3-1 | (i) | D-1-1a | ⊙ | This invention |
| 3-2 | (iv) | D-1-1a | ○ | This invention |
| 3-3 | (i) | D-1-21a | ⊙ | This invention |
| 3-4 | (iv) | D-1-21a | ○ | This invention |
| 3-5 | (i) | D-1-16a | ⊙ | This invention |
| 3-6 | (iv) | D-1-16a | ○ | This invention |
| 3-7 | (i) | D-1-17a | ⊙ | This invention |
| 3-8 | (iv) | D-1-17a | ○ | This invention |
| 3-9 | (i) | D-1-22a | ○ | This invention |
| 3-10 | (iv) | D-1-22a | ○ | This invention |
| 3-11 | (i) | D-1-23a | ○ | This invention |
| 3-12 | (iv) | D-1-23a | ○ | This invention |
| 3-13 | (i) | D-8-1a | ● | This invention |
| 3-14 | (iv) | D-8-1a | ● | This invention |
| 3-15 | (i) | Sensitizing dye A | Δ | Comparative example |
| 3-16 | (iv) | Sensitizing dye A | X | Comparative example |
| 3-17 | (i) | Sensitizing dye B | Δ | Comparative example |
| 3-18 | (iv) | Sensitizing dye B | X | Comparative example |
| 3-19 | (i) | Sensitizing dye C | Δ | Comparative example |
| 3-20 | (iv) | Sensitizing dye C | Δ | Comparative example |

Table 3 shows that the conversion efficiency of the test cell prepared by using the metal complex dyes of the present invention showed a conversion efficiency as high as 7.5% or more. Whereas, when the comparative dyes were used, the conversion efficiency was equal to 6.5 or more to less than 6.7 at most.

Experiment 4

Sample cells (A) to (D) of the dye-sensitized solar cell were prepared, photoelectric conversion characteristic of each cell were evaluated, and the conversion efficiency was determined.

(Preparation of Sample Cell (A))

1. Preparation of Semiconductor Film 5 g of titanium hydride was suspended in 1 liter of pure water, and 400 g of a 5 mass % hydrogen peroxide solution was added thereto over 30 minutes. Subsequently, the mixture was heated to 80° C. to dissolve, and thus a solution of peroxotitanic acid was prepared. A portion of 90% by volume was separated from the total amount of this solution, and concentrated aqueous ammonia was added thereto to adjust the portion to pH 9. The resultant was placed in an autoclave and was subjected to a hydrothermal treatment at 250° C. for 5 hours under saturated vapor pressure. Thus, titania colloidal particles (A) were prepared. The titania colloidal particles thus obtained were composed of anatase type titanium oxide having high crystallinity as determined by X-ray diffraction.

Subsequently, the titania colloidal particles (A) obtained as described above were concentrated to 10% by mass, and were mixed with the peroxotitanic acid solution. The amount of titanium in the mixed liquid was calculated in terms of $TiO_2$, hydroxypropyl cellulose was added to the mixture as a film forming aid, such that the amount of hydroxypropyl cellulose reached 30% by mass relative to the mass of $TiO_2$. Thus, a coating liquid for semiconductor film formation was prepared.

Subsequently, the coating liquid was applied on a transparent glass substrate on which fluorine-doped tin oxide was formed as an electrode layer, and was naturally dried. The coating liquid was then irradiated with ultraviolet radiation in an amount of 6000 mJ/cm$^2$ using a low pressure mercury lamp to decompose peroxo acid, and thereby the coating film was cured. The coating film was heated at 300° C. for 30 minutes, and thereby decomposition of hydroxypropyl cellulose and annealing were carried out. Thus, a metal oxide semiconductor film (A) was formed on the glass substrate.

2. Adsorption of Metal Complex Dye

Next, an ethanol solution of each of the metal complex dyes described in Table 3 at a concentration of $3 \times 10^{-4}$ mol/L was prepared. These metal complex dye solution was applied on the metal oxide semiconductor film (A) with a 100-rpm spinner, and was dried. This application and drying processes were repeated five times.

3. Preparation of Sample Cell (A)

In a mixed solvent of acetonitrile and ethylene carbonate at a volume ratio of 1:5 (acetonitrile:(ethylene carbonate)), tetrapropylammonium iodide was dissolved to a concentration of 0.46 mol/L, and iodine to a concentration of 0.07 mol/L. Thus, an electrolyte solution was prepared.

The glass substrate produced in the above was used as one electrode, and a transparent glass substrate in which fluorine-doped tin oxide was formed as an electrode and platinum was supported thereon, was used as the other electrode, so that these electrodes were arranged to face each other. The lateral sides were sealed with a resin, and the electrolyte solution prepared above was included between the electrodes. Furthermore, lead wires were connected between the electrodes, and thus a sample cell (A) was produced.

(Preparation of Sample Cell (B))

A metal oxide semiconductor film (B) was formed in the same manner as in the case of the metal oxide semiconductor film (A), except that the film was cured by irradiating with ultraviolet radiation to decompose peroxo acid, and then the film was irradiated with ions of Ar gas (manufactured by Nissin Electric Co., Ltd.: ion injection device, irradiated at 200 eV for 10 hours). A metal oxide semiconductor film on which the dye was adsorbed was prepared by allowing the metal complex dye described in the following Table 4 to adsorb thereon. A sample cell (B) was prepared using this semiconductor film in a manner similar to the sample cell (A).

(Preparation of Sample Cell (C))

Was diluted 18.3 g of titanium tetrachloride with pure water, and an aqueous solution containing 1.0% by mass of the titanium compound in terms of $TiO_2$ was obtained. While this aqueous solution was stirred, a 15 mass % aqueous ammonia solution was added thereto, and thus a white slurry at pH 9.5 was obtained. This slurry was filtered and washed, and thus a cake of hydrated titanium oxide gel at a concentration of 10.2% by mass in terms of $TiO_2$ was obtained. This cake was mixed with 400 g of a 5 mass % hydrogen peroxide solution, and then the mixture was heated to 80° C. to dissolve. Thus, a solution of peroxotitanic acid was prepared. A portion of 90% by volume was separated from the total amount of this solution, and concentrated aqueous ammonia was added thereto to adjust the portion to pH 9. The resultant was placed in an autoclave and was subjected to a hydrothermal treatment at 250° C. for 5 hours under saturated vapor pressure. Thus, titania colloidal particles (C) were prepared.

Subsequently, a metal oxide semiconductor film (C) was formed in the same manner as in the case of the metal oxide semiconductor film (A), using the peroxotitanic acid solution and the titania colloidal particles (C) obtained as described above. A metal oxide semiconductor film on which the dye was adsorbed was prepared by allowing the metal complex dye described in the following Table 4 to adsorb thereon. A sample cell (C) was prepared using the semiconductor film in a manner similar to the sample cell (A).

(Preparation of Sample Cell (D))

18.3 g of titanium tetrachloride was diluted with pure water, and an aqueous solution containing 1.0% by mass of the titanium compound in terms of $TiO_2$ was obtained. While this aqueous solution was stirred, a 15 mass % aqueous ammonia solution was added thereto, and thus a white slurry at pH 9.5 was obtained. This slurry was filtered and washed, and then was suspended in pure water. Thus, a slurry of hydrated titanium oxide gel at a concentration 0.6% by mass in terms of $TiO_2$ was obtained. Hydrochloric acid was added to this slurry to adjust the pH to 2. Subsequently, the slurry was placed in an autoclave, and was subjected to a hydrothermal treatment at 180° C. for 5 hours under saturated vapor pressure, and thus titania colloidal particles (D) were prepared.

Next, the titania colloidal particles (D) were concentrated to 10% by mass, and hydroxypropyl cellulose was added to the particles as a film forming aid such that the amount of hydroxypropyl cellulose reached 30% by mass in terms of $TiO_2$. Thus, a coating liquid for semiconductor film formation was prepared. Subsequently, the coating liquid was applied on a transparent glass substrate on which fluorine-doped tin oxide was formed as an electrode layer, and was naturally dried. Subsequently, the coating liquid was irradiated with ultraviolet radiation in an amount of 6000 mJ/$cm^2$ using a low pressure mercury lamp, and thereby the film was cured. The film was further heated at 300° C. for 30 minutes to perform decomposition of hydroxypropyl cellulose and annealing. Thus, a metal oxide semiconductor film (D) was formed. A metal oxide semiconductor film on which the dye was adsorbed was prepared by allowing the metal complex dye described in the following Table 4 to adsorb thereon. A sample cell (D) was prepared using the semiconductor film in a manner similar to the sample cell (A).

(Measurement of Photoelectric Conversion Characteristics)

Each of the test cells (A) to (D) was exposed to light having an intensity of 100 W/$cm^2$ by using a solar simulator, and Voc (voltage in open-circuit), Joc (electric current density caused in short of circuit), FF (curve factor) and 11 (conversion efficiency) were determined. The results of the conversion efficiency are shown in Table 4.

The results were evaluated such that one having a conversion efficiency of 7.5% or more was rated as "⊙"; one having a conversion efficiency of equal to or more than 7.0% and less than 7.5% was rated as "○"; one having a conversion efficiency of equal to or more than 6.5% and less than 7.0% was rated as "Δ"; and one having a conversion efficiency of less than 6.5% was rated as "x". One having a conversion efficiency equal to or more than 7.0% was deemed to be passable.

TABLE 4

| Sample No. | Sample cell | Used dye | Conversion efficiency (%) | Remarks |
|---|---|---|---|---|
| 4-1 | (A) | D-1-1a | ⊙ | This invention |
| 4-2 | (B) | D-1-1a | ⊙ | This invention |
| 4-3 | (C) | D-1-1a | ⊙ | This invention |
| 4-4 | (D) | D-1-1a | ○ | This invention |
| 4-5 | (A) | D-1-21a | ⊙ | This invention |
| 4-6 | (B) | D-1-21a | ⊙ | This invention |
| 4-7 | (C) | D-1-21a | ⊙ | This invention |
| 4-8 | (D) | D-1-21a | ○ | This invention |
| 4-9 | (A) | Sensitizing dye A | Δ | Comparative example |
| 4-10 | (B) | Sensitizing dye A | Δ | Comparative example |
| 4-11 | (C) | Sensitizing dye A | Δ | Comparative example |
| 4-12 | (D) | Sensitizing dye A | X | Comparative example |
| 4-13 | (A) | Sensitizing dye B | Δ | Comparative example |
| 4-14 | (B) | Sensitizing dye B | X | Comparative example |
| 4-15 | (C) | Sensitizing dye B | X | Comparative example |
| 4-16 | (D) | Sensitizing dye B | X | Comparative example |
| 4-17 | (A) | Sensitizing dye C | Δ | Comparative example |

TABLE 4-continued

| Sample No. | Sample cell | Used dye | Conversion efficiency (%) | Remarks |
|---|---|---|---|---|
| 4-18 | (B) | Sensitizing dye C | Δ | Comparative example |
| 4-19 | (C) | Sensitizing dye C | Δ | Comparative example |
| 4-20 | (D) | Sensitizing dye C | X | Comparative example |

Table 4 shows that the dye-sensitized solar cell prepared by using the metal complex dye of the present invention has a passable level of the conversion efficiency. Whereas, when the comparative dye was used, the conversion efficiency was low.

Experiment 5

The photoelectric conversion element was produced using semiconductor fine particles obtained by changing the methods for preparation of titanium oxide, photoelectric conversion characteristics were evaluated, and the conversion efficiency was determined.

(1) Preparation of Titanium Oxide According to Heat Treatment Method Titanium Oxide 1A (Brookite Type), Titanium Oxide 1B (Anatase Type) and Titanium Oxide 2B (Rutile Type)

Commercially available anatase type titanium oxide 1B (manufactured by Ishihara Sangyo Kaisha, Ltd., trade name: ST-01) was used, and this product was heated to about 900° C. to convert it to brookite type titanium oxide 1A, and was further heated to about 1,200° C. to convert it to rutile type titanium oxide 2B.

(2) Synthesis of Titanium Oxide According to a Wet Synthesis Method Titanium Oxide 2A (Brookite Type)

A reaction tank equipped with a reflux condenser was charged with 954 mL of distilled water, and the distilled water was heated to 95° C. While the stirring speed was maintained at about 200 rpm, 46 mL of an aqueous solution of titanium tetrachloride (Ti content: 16.3% by mass, specific gravity 1.59, purity 99.9%) was added dropwise to this distilled water in the reaction tank at a rate of about 5.0 mL/min. At this time, caution was taken to prevent the temperature of the reaction liquid from falling. As a result, the concentration of titanium tetrachloride was 0.25 mol/L (2% by mass in terms of titanium oxide). In the reaction tank, the reaction liquid began to turn cloudy immediately after the dropwise addition, but the reaction liquid was maintained at that temperature. After completion of the dropwise addition, the temperature was further increased to heat the reaction liquid close to the boiling point (104° C.), and the reaction liquid was maintained in this state for 60 minutes to completely terminate the reaction.

A sol obtained by the reaction was filtered, and then the sol was made into a powder using a vacuum dryer at 60° C. This powder was quantitatively analyzed by an X-ray diffraction method. As a result, the ratio of (peak intensity of the brookite type 121 plane)/(peak intensity at the position where the three types overlap) was 0.38, and the ratio of (main peak intensity of the rutile type)/(peak intensity at the position where the three types overlap) was 0.05. From an analysis of these data, the titanium oxide was crystalline, composed of about 70.0% by mass of the brookite type, about 1.2% by mass of the rutile type, and about 28.8% by mass of the anatase type. Furthermore, the fine particles were observed with a transmission electron microscope, and the average particle size of the primary particles was 0.015 μm.

Titanium Oxide 3A (Brookite Type)

An aqueous solution of titanium trichloride (Ti content: 28% by mass, specific gravity 1.5, purity 99.9%) was diluted with distilled water, and a solution at a concentration of 0.25 mol/L in terms of titanium was obtained. At this time, the solution was ice-cooled to prevent the temperature of the liquid from rising, and thus the solution was maintained at 50° C. or below. Subsequently, 500 mL of this solution was introduced into a reaction tank equipped with a reflux condenser, and while this solution was heated to 85° C., ozone gas with a purity of 80% generated from a ozone gas generating apparatus was bubbled into the solution at a rate of 1 L/min to induce an oxidation reaction. The system was maintained in this state for 2 hours, and thus the reaction was completely terminated. A sol thus obtained was filtered and dried in a vacuum to obtain a powder. This powder was quantitatively analyzed by an X-ray diffraction method. As a result, the ratio of (peak intensity of the brookite type 121 plane)/(peak intensity at the position where the three types overlapped) was 0.85, and the ratio of (main peak intensity of the rutile type)/(peak intensity at the position where the three types overlapped) was 0. From an analysis of these data, the titanium dioxide was composed of about 98% by mass of the brookite type, 0% by mass of the rutile type, 0% by mass of the anatase type, and about 2% of amorphous titanium dioxide. Furthermore, the fine particles were observed with a transmission electron microscope, and the average particle size of the primary particles was 0.05 μm.

Titanium Oxide 3B (Anatase Type)

To 855 mL of distilled water, 145 mL of titanium sulfate solution (Ti: 30% by mass, specific gravity 1.65) was added. A titanium sulfate concentration at this time was 1.5 mol/L. The solution was heated to 100° C. to allow hydrolysis, and thus white precipitates were obtained. These precipitates were filtered and washed, and dried using a vacuum dryer at 60° C., and powderized. X-ray diffraction analysis shows that the sample was an anatase type. Furthermore, the fine particles were observed with a transmission electron microscope, and the average particle size of the primary particles was 0.025 μm.

Comparative Titanium Oxide 4 (Rutile Type)

A titanyl sulfate solution was thermally decomposed according to an ordinary method, and 80 g of 48 vol % NaOH solution was charged into 950 g of filtered and washed hydrous titanium oxide slurry (corresponding to 100 g of $TiO_2$ equivalent) while stirring, and the resultant mixture was heated at 95° C. for 4 hours. Subsequently, 600 g of 30 mass % hydrochloric acid was charged into 2 kg of slurry obtained by sufficiently washing the treated matter while stirring, and the resultant mixture was heated at 98° C. for 5 hours, and thus a titania sol was prepared. The titania sol showed a rutile type crystal structure in X-ray diffraction. An average particle size of the thus obtained titanium oxide fine particles having the rutile type crystal structure was 0.012 μm.

(Production and Evaluation of Dye-Sensitized Photoelectric Conversion Element)

The titanium oxides prepared in the above-described sections were used as semiconductor, and photoelectric conversion elements having a configuration as shown in FIG. 1 of JP-A-2000-340269 were produced as follows. Fluorine-doped tin oxide was coated on a glass substrate, and this was used as a conductive transparent electrode. A paste containing each type of the titanium oxide particles as a raw material was prepared, and the paste was applied on the electrode surface by a bar coating method to a thickness of 50 μm. Subsequently, the paste was calcined at 500° C., and thus a thin layer having a thickness of about 20 μm was formed. An ethanol solution of the metal complex dye described in Table 5 below at a molar concentration of $3 \times 10^{-4}$ M was prepared, and the glass substrate on which a thin layer of titanium oxide was formed was immersed in this ethanol solution and was maintained therein for 12 hours at room temperature. As a result, the complex above was adsorbed on the thin layer of titanium oxide.

An acetonitrile solution of an iodide salt of tetrapropylammonium and lithium iodide was used as an electrolytic liquid, and platinum was used as a counter electrode. Thus, a photoelectric conversion element having the configuration shown in FIG. 1 of JP-A-2000-340269 was produced. For the photoelectric conversion, the element was irradiated with light from a high pressure mercury lamp (the infrared portion was cut with a filter) at a power of 160 W, and the conversion efficiency at that time was measured. The results are shown in Table 5. The results are represented such that one having a conversion efficiency of 7.5% or more is indicated with "⊙"; one having a conversion efficiency of equal to or more than 7.0% and less than 7.5% is indicated with "○"; one having a conversion efficiency of equal to or more than 6.5% and less than 7.0% is indicated with "Δ"; and one having a conversion efficiency of less than 6.5% is indicated with "x". One having a conversion efficiency equal to or more than 7.0% was deemed to be passable.

constitutes a photoelectrode were prepared, and a dye-sensitized solar cell was produced using this paste.

[Preparation of Paste]

First, a paste for forming a semiconductor layer or a light scattering layer for a semiconductor electrode that constitutes a photoelectrode, was prepared by the following procedure.

(Paste 1)

Spherical-shaped $TiO_2$ particles (anatase type, average particle size: 25 nm; hereinafter, referred to as spherical $TiO_2$ particles 1) were introduced into a nitric acid solution and stirred. Thus, a titania slurry was prepared. Subsequently, a cellulose-based binder was added to the titania slurry as a thickening agent, and the mixture was kneaded. Thus, a paste was prepared.

(Paste 2)

Spherical $TiO_2$ particles 1 and spherical-shaped $TiO_2$ particles (anatase type, average particle size: 200 nm; hereinafter, referred to as spherical $TiO_2$ particles 2) were introduced into a nitric acid solution and stirred. Thus, a titania slurry was prepared. Subsequently, a cellulose-based binder was added to the titania slurry as a thickening agent, and the mixture was kneaded. Thus, a paste (mass of the $TiO_2$ particles 1:mass of the $TiO_2$ particles 2=30:70) was prepared.

TABLE 5

| Sample No. | Titanium oxide | Metal complex dye | Conversion efficiency (%) | Remarks |
|---|---|---|---|---|
| 5-1 | Titanium oxide 1A | D-1-1a | ⊙ | This invention |
| 5-2 | Titanium oxide 1B | D-1-1a | ○ | This invention |
| 5-3 | Titanium oxide 2A | D-1-1a | ⊙ | This invention |
| 5-4 | Titanium oxide 3A | D-1-1a | ⊙ | This invention |
| 5-5 | Titanium oxide 2B | D-1-1a | ○ | This invention |
| 5-6 | Titanium oxide 3B | D-1-1a | ○ | This invention |
| 5-7 | Titanium oxide 1A | D-1-21a | ○ | This invention |
| 5-8 | Titanium oxide 1B | D-1-21a | ○ | This invention |
| 5-9 | Titanium oxide 2A | D-1-21a | ⊙ | This invention |
| 5-10 | Titanium oxide 3A | D-1-21a | ⊙ | This invention |
| 5-11 | Titanium oxide 2B | D-1-21a | ○ | This invention |
| 5-12 | Titanium oxide 3B | D-1-21a | ○ | This invention |
| 5-13 | Titanium oxide 1A | Sensitizing dye A | Δ | Comparative example |
| 5-14 | Titanium oxide 1B | Sensitizing dye A | X | Comparative example |
| 5-15 | Titanium oxide 2A | Sensitizing dye A | Δ | Comparative example |
| 5-16 | Titanium oxide 3A | Sensitizing dye A | Δ | Comparative example |
| 5-17 | Titanium oxide 2B | Sensitizing dye A | X | Comparative example |
| 5-18 | Titanium oxide 3B | Sensitizing dye A | X | Comparative example |
| 5-19 | Titanium oxide 1A | Sensitizing dye B | X | Comparative example |
| 5-20 | Titanium oxide 1B | Sensitizing dye B | X | Comparative example |
| 5-21 | Titanium oxide 2A | Sensitizing dye B | X | Comparative example |
| 5-22 | Titanium oxide 3A | Sensitizing dye B | Δ | Comparative example |
| 5-23 | Titanium oxide 2B | Sensitizing dye B | X | Comparative example |
| 5-24 | Titanium oxide 3B | Sensitizing dye B | X | Comparative example |
| 5-25 | Titanium oxide 1A | Sensitizing dye C | Δ | Comparative example |
| 5-26 | Titanium oxide 1B | Sensitizing dye C | Δ | Comparative example |
| 5-27 | Titanium oxide 2A | Sensitizing dye C | X | Comparative example |
| 5-28 | Titanium oxide 3A | Sensitizing dye C | Δ | Comparative example |
| 5-29 | Titanium oxide 2B | Sensitizing dye C | X | Comparative example |
| 5-30 | Titanium oxide 3B | Sensitizing dye C | X | Comparative example |

Table 5 shows that the conversion efficiency showed a passable level value even by changing titanium oxides when the metal complex dye of the present invention was used. However, when the comparative dye was used, any of the conversion efficiency decreased.

Experiment 6

Various kinds of pastes for forming a semiconductor layer or a light-scattering layer of a semiconductor electrode that (Paste 3)

The paste 1 was mixed with rod-shaped $TiO_2$ particles (anatase type, diameter: 100 nm, aspect ratio: 5; hereinafter, referred to as rod-shaped $TiO_2$ particles 1), and thus a paste having a ratio of the mass of the rod-shaped $TiO_2$ particles 1 to the mass of the paste 1 of 10:90 was prepared.

(Paste 4)

The paste 1 was mixed with the rod-shaped $TiO_2$ particles 1, and thus a paste having a ratio of the mass of the rod-shaped $TiO_2$ particles 1 to the mass of the paste 1 of 30:70 was prepared.

(Paste 5)

The paste 1 was mixed with the rod-shaped $TiO_2$ particles 1, and thus a paste having a ratio of the mass of the rod-shaped $TiO_2$ particles 1 to the mass of the paste 1 of 50:50 was prepared.

(Paste 6)

The paste 1 was mixed with plate-shaped mica particles (diameter: 100 nm, aspect ratio: 6; hereinafter, referred to as plate-shaped mica particles 1), and thus a paste having a ratio of the mass of the plate-shaped mica particles 1 to the mass of the paste 1 of 20:80 was prepared.

(Paste 7)

The paste 1 was mixed with rod-shaped $TiO_2$ particles (anatase type, diameter: 30 nm, aspect ratio: 6.3; hereinafter, referred to as rod-shaped $TiO_2$ particles 2), and thus a paste having a ratio of the mass of the rod-shaped $TiO_2$ particles 2 to the mass of the paste 1 of 30:70 was prepared.

(Paste 8)

The paste 1 was mixed with rod-shaped $TiO_2$ particles (anatase type, diameter: 50 nm, aspect ratio: 6.1; hereinafter, referred to as rod-shaped $TiO_2$ particles 3), and thus a paste having a ratio of the mass of the rod-shaped $TiO_2$ particles 3 to the mass of the paste 1 of 30:70 was prepared.

(Paste 9)

The paste 1 was mixed with rod-shaped $TiO_2$ particles (anatase type, diameter: 75 nm, aspect ratio: 5.8; hereinafter, referred to as rod-shaped $TiO_2$ particles 4), and thus a paste having a ratio of the mass of the rod-shaped $TiO_2$ particles 4 to the mass of the paste 1 of 30:70 was prepared.

(Paste 10)

The paste 1 was mixed with rod-shaped $TiO_2$ particles (anatase type, diameter: 130 nm, aspect ratio: 5.2; hereinafter, referred to as rod-shaped $TiO_2$ particles 5), and thus a paste having a ratio of the mass of the rod-shaped $TiO_2$ particles 5 to the mass of the paste 1 of 30:70 was prepared.

(Paste 11)

The paste 1 was mixed with rod-shaped $TiO_2$ particles (anatase type, diameter: 180 nm, aspect ratio: 5; hereinafter, referred to as rod-shaped $TiO_2$ particles 6), and thus a paste having a ratio of the mass of the rod-shaped $TiO_2$ particles 6 to the mass of the paste 1 of 30:70 was prepared.

(Paste 12)

The paste 1 was mixed with rod-shaped $TiO_2$ particles (anatase type, diameter: 240 nm, aspect ratio: 5; hereinafter, referred to as rod-shaped $TiO_2$ particles 7), and thus a paste having a ratio of the mass of the rod-shaped $TiO_2$ particles 7 to the mass of the paste 1 of 30:70 was prepared.

(Paste 13)

The paste 1 was mixed with rod-shaped $TiO_2$ particles (anatase type, diameter: 110 nm, aspect ratio: 4.1; hereinafter, referred to as rod-shaped $TiO_2$ particles 8), and thus a paste having a ratio of the mass of the rod-shaped $TiO_2$ particles 8 to the mass of the paste 1 of 30:70 was prepared.

(Paste 14)

The paste 1 was mixed with rod-shaped $TiO_2$ particles (anatase type, diameter: 105 nm, aspect ratio: 3.4; hereinafter, referred to as rod-shaped $TiO_2$ particles 9), and thus a paste having a ratio of the mass of the rod-shaped $TiO_2$ particles 9 to the mass of the paste 1 of 30:70 was prepared.

(Dye-Sensitized Solar Cell 1)

A photoelectrode having the same configuration as that of the photoelectrode 12 shown in FIG. 5 of JP-A-2002-289274 was produced by the procedure described below, and using this photoelectrode, a dye-sensitized solar cell 1 which has a dimension of 10×10 mm and has the same configuration as that of the dye-sensitized solar cell 20 except for the photoelectrode, was produced.

A transparent electrode in which fluorine-doped $SnO_2$ conductive film (thickness: 500 nm) was formed on a glass substrate, was provided. On this $SnO_2$ conductive film, the above-described paste 2 was applied by screen printing, and then the paste was dried. Thereafter, the paste was calcined under the conditions of 450° C. in air. Furthermore, a semiconductor electrode having the same configuration as that of the semiconductor electrode 2 shown in FIG. 5 (area of light-receiving surface: 10 mm×10 mm, layer thickness: 10 µm, thickness of the semiconductor layer: 6 µm, thickness of the light scattering layer: 4 µm, and content of the rod-shaped $TiO_2$ particles 1 contained in the light scattering layer: 30% by mass) was formed on a $SnO_2$ conductive film by repeating these processes of screen printing and calcination using the paste 4. Thus, a photoelectrode which did not contain any sensitizing dye was produced.

Subsequently, a dye was adsorbed on the semiconductor electrode as follows. First, anhydrous ethanol which had been dehydrated with magnesium ethoxide was used as a solvent, and the metal complex dye described in Table 6 was dissolved in this anhydrous ethanol to a concentration of $3\times10^{-4}$ mol/L. Thus, a dye solution was prepared. Subsequently, the semiconductor electrode was immersed in this solution, and thereby, the dye was adsorbed on the semiconductor electrode in an amount of about $1.5\times10^{-7}$ mol/cm$^2$. Thus, a photoelectrode 10 was completed.

Subsequently, a platinum electrode (thickness of Pt thin film: 100 nm) having the same shape and size as those of the photoelectrode described above was produced as a counter electrode, and an iodine-based redox solution containing iodine and lithium iodide was prepared as an electrolyte E. Furthermore, a spacer-S (trade name: "Surlyn") manufactured by DuPont Company, which had a shape matching the size of the semiconductor electrode, was prepared. As shown in FIG. 3 of JP-A-2002-289274, the photoelectrode 10 and the counter electrode CE were arranged to face each other, with the spacer-S interposed therebetween, and the electrolyte described above was filled in the inside. Thus, a dye-sensitized solar cell was completed.

(Dye-Sensitized Solar Cell 2)

A photoelectrode having the same configuration as that of the photoelectrode 10 shown in FIG. 1 of JP-A-2002-289274, and a dye-sensitized solar cell 2 having the same configuration as that of the dye-sensitized solar cell 20 shown in FIG. 3 of JP-A-2002-289274 were produced by the same procedure as that used for the dye-sensitized solar cell 1, except that the production of the semiconductor electrode was carried out in the manner described below.

Herein, adsorption of the dye on the semiconductor electrode was performed in a manner similar to the case of the dye-sensitized solar cell 1. First, anhydrous ethanol which had been dehydrated with magnesium ethoxide was used as a solvent, and the metal complex dye described in Table 6 was dissolved in this anhydrous ethanol to a concentration of $3\times10^{-4}$ mol/L. Thus, a dye solution was prepared. Subsequently, the semiconductor electrode was immersed in this solution, and thereby, the dye was adsorbed on the semiconductor electrode in an amount of about $1.5\times10^{-7}$ mol/cm$^2$. Thus, a photoelectrode 10 was completed. Adsorption of the dye on the semiconductor electrode in the following dye-sensitized solar cells was performed in a similar manner.

The paste 2 was used as a paste for semiconductor layer formation. The paste 2 was applied on the $SnO_2$ conductive film by screen printing, and then was dried. Subsequently, the paste was calcined under the conditions of 450° C. in air, and thus a semiconductor layer was formed.

The paste 3 was used as a paste for the innermost layer formation of the light scattering layer. Also, the paste 5 was used as a paste for the outermost layer formation of the light scattering layer. Then, a light scattering layer was formed on the semiconductor layer in the same manner as in the case of the dye-sensitized solar cell 1.

A semiconductor electrode (area of light-receiving surface: 10 mm×10 mm, layer thickness: 10 μm, thickness of semiconductor layer: 3 μm, thickness of the innermost layer: 4 μm, content ratio of the rod-shaped $TiO_2$ particles 1 contained in the innermost layer: 10% by mass, thickness of the outermost layer: 3 μm, and content ratio of the rod-shaped $TiO_2$ particles 1 contained in the innermost layer: 50% by mass) having the same configuration as that of the semiconductor electrode 2 shown in FIG. 1 of JP-A-2002-289274 was formed on the $SnO_2$ conductive film. Thus, a photoelectrode that did not contain a sensitizing dye was produced. In the same manner as in the case of the dye-sensitized solar cell 1, the photoelectrode and the counter electrode CE were arranged to face each other, with the spacer-S interposed therebetween, and the electrolyte was filled inside. Thus, a dye-sensitized solar cell 2 was completed.

(Dye-Sensitized Solar Cell 3)

During the production of the semiconductor electrode, a photoelectrode having the same configuration as that of the photoelectrode 10 shown in FIG. 5, and a dye-sensitized solar cell 3 having the same configuration as that of the dye-sensitized solar cell 20 shown in FIG. 3 described in JP-A-2002-289274 were produced by the same procedure as that used for the dye-sensitized solar cell 1, except that the paste 1 was used as the paste for semiconductor layer formation, and the paste 4 was used as the paste for light scattering layer formation. The semiconductor electrode had a configuration as follows: area of the light receiving surface: 10 mm×10 mm, layer thickness: 10 μm, thickness of the semiconductor layer: 5 μm, thickness of light scattering layer: 5 μm, and content ratio of the rod-shaped $TiO_2$ particles 1 contained in the light scattering layer: 30% by mass.

(Dye-Sensitized Solar Cell 4)

During the production of the semiconductor electrode, a photoelectrode having the same configuration as that of the photoelectrode 10 shown in FIG. 5, and a dye-sensitized solar cell 4 having the same configuration as that of the dye-sensitized solar cell 20 shown in FIG. 3 described in JP-A-2002-289274 were produced by the same procedure as that used for the dye-sensitized solar cell 1, except that the paste 2 was used as the paste for semiconductor layer formation, and the paste 6 was used as the paste for light scattering layer formation. The semiconductor electrode had a configuration as follows: area of the light receiving surface: 10 mm×10 mm, layer thickness: 10 μm, thickness of the semiconductor layer: 6.5 μm, thickness of light scattering layer: 3.5 μm, and content ratio of the plate-shaped mica particles 1 contained in the light scattering layer: 20% by mass.

(Dye-Sensitized Solar Cell 5)

During the production of the semiconductor electrode, a photoelectrode and a dye-sensitized solar cell 5 were produced by the same procedure as that used for the dye-sensitized solar cell 1, except that the paste 2 was used as the paste for semiconductor layer formation, and the paste 8 was used as the paste for light scattering layer formation. The content ratio of the rod-shaped $TiO_2$ particles 3 contained in the light scattering layer of the semiconductor electrode: 30% by mass.

(Dye-Sensitized Solar Cell 6)

During the production of the semiconductor electrode, a photoelectrode and a dye-sensitized solar cell 6 were produced by the same procedure as that used for the dye-sensitized solar cell 1, except that the paste 2 was used as the paste for semiconductor layer formation, and the paste 9 was used as the paste for light scattering layer formation. The content ratio of the rod-shaped $TiO_2$ particles 4 contained in the light scattering layer of the semiconductor electrode: 30% by mass.

(Dye-Sensitized Solar Cell 7)

During the production of the semiconductor electrode, a photoelectrode and a dye-sensitized solar cell 7 were produced by the same procedure as that used for the dye-sensitized solar cell 1, except that the paste 2 was used as the paste for semiconductor layer formation, and the paste 10 was used as the paste for light scattering layer formation. The content ratio of the rod-shaped $TiO_2$ particles 5 contained in the light scattering layer of the semiconductor electrode: 30% by mass.

(Dye-Sensitized Solar Cell 8)

During the production of the semiconductor electrode, a photoelectrode and a dye-sensitized solar cell 8 were produced by the same procedure as that used for the dye-sensitized solar cell 1, except that the paste 2 was used as the paste for semiconductor layer formation, and the paste 11 was used as the paste for light scattering layer formation. The content ratio of the rod-shaped $TiO_2$ particles 6 contained in the light scattering layer of the semiconductor electrode: 30% by mass.

(Dye-Sensitized Solar Cell 9)

During the production of the semiconductor electrode, a photoelectrode and a dye-sensitized solar cell 9 were produced by the same procedure as that used for the dye-sensitized solar cell 1, except that the paste 2 was used as the paste for semiconductor layer formation, and the paste 13 was used as the paste for light scattering layer formation. The content ratio of the rod-shaped $TiO_2$ particles 8 contained in the light scattering layer of the semiconductor electrode: 30% by mass.

(Dye-Sensitized Solar Cell 10)

During the production of the semiconductor electrode, a photoelectrode and a dye-sensitized solar cell 10 were produced by the same procedure as that used for the dye-sensitized solar cell 1, except that the paste 2 was used as the paste for semiconductor layer formation, and the paste 14 was used as the paste for light scattering layer formation. The content ratio of the rod-shaped $TiO_2$ particles 9 contained in the light scattering layer of the semiconductor electrode: 30% by mass.

(Dye-Sensitized Solar Cell 11)

During the production of the semiconductor electrode, a photoelectrode and a dye-sensitized solar cell 11 were produced by the same procedure as that used for the dye-sensitized solar cell 1, except that a semiconductor electrode (area of light-receiving surface: 10 mm×10 mm, and layer thickness: 10 μm) having only a semiconductor layer was produced using only the paste 2.

(Dye-Sensitized Solar Cell 12)

During the production of the semiconductor electrode, a photoelectrode and a dye-sensitized solar cell 12 were produced by the same procedure as that used for the dye-sensitized solar cell 1, except that the paste 2 was used as the paste for semiconductor layer formation, and the paste 7 was used as the paste for light scattering layer formation. The content ratio of the rod-shaped $TiO_2$ particles 2 contained in the light scattering layer of the semiconductor electrode: 30% by mass.

[Cell Characterization Test]

A cell characterization test was carried out, and the conversion efficiencies of the dye-sensitized solar cells were measured. The cell characteristics evaluation test was carried out using a solar simulator (manufactured by Wacom Electric Co., Ltd., WXS-85-H type), under the measurement conditions in which the condition for irradiation with pseudo-sunlight from a xenon lamp through an AM1.5 filter was set at 1000 W/cm$^2$. The current-voltage characteristics were measured using an I-V tester, and the conversion efficiency η [%] was determined. The results are shown in Table 6. The results are represented such that one having a conversion efficiency of 7.5% or more is indicated with "⊙"; one having a conversion efficiency of equal to or more than 7.0% and less than 7.5% is indicated with "○"; one having a conversion efficiency of equal to or more than 6.5% and less than 7.0% is indicated with "Δ"; and one having a conversion efficiency of less than 6.5% is indicated with "x". One having a conversion efficiency equal to or more than 7.0% was deemed to be passable.

TABLE 6

| Sample No. | Dye-sensitized solar cell | Metal complex dye | Conversion efficiency (%) | Remarks |
| --- | --- | --- | --- | --- |
| 6-1 | Dye-sensitized solar cell 1 | D-1-1a | ⊙ | Ex |
| 6-2 | Dye-sensitized solar cell 2 | D-1-1a | ⊙ | Ex |
| 6-3 | Dye-sensitized solar cell 3 | D-1-1a | ⊙ | Ex |
| 6-4 | Dye-sensitized solar cell 4 | D-1-1a | ⊙ | Ex |
| 6-5 | Dye-sensitized solar cell 5 | D-1-1a | ⊙ | Ex |
| 6-6 | Dye-sensitized solar cell 6 | D-1-1a | ⊙ | Ex |
| 6-7 | Dye-sensitized solar cell 7 | D-1-1a | ⊙ | Ex |
| 6-8 | Dye-sensitized solar cell 8 | D-1-1a | ⊙ | Ex |
| 6-9 | Dye-sensitized solar cell 9 | D-1-1a | ⊙ | Ex |
| 6-10 | Dye-sensitized solar cell 10 | D-1-1a | ⊙ | Ex |
| 6-11 | Dye-sensitized solar cell 11 | D-1-1a | ○ | Ex |
| 6-12 | Dye-sensitized solar cell 12 | D-1-1a | ○ | Ex |
| 6-13 | Dye-sensitized solar cell 1 | D-1-21a | ⊙ | Ex |
| 6-14 | Dye-sensitized solar cell 2 | D-1-21a | ⊙ | Ex |
| 6-15 | Dye-sensitized solar cell 3 | D-1-21a | ⊙ | Ex |
| 6-16 | Dye-sensitized solar cell 4 | D-1-21a | ⊙ | Ex |
| 6-17 | Dye-sensitized solar cell 5 | D-1-21a | ○ | Ex |
| 6-18 | Dye-sensitized solar cell 6 | D-1-21a | ⊙ | Ex |
| 6-19 | Dye-sensitized solar cell 7 | D-1-21a | ○ | Ex |
| 6-20 | Dye-sensitized solar cell 8 | D-1-21a | ⊙ | Ex |
| 6-21 | Dye-sensitized solar cell 9 | D-1-21a | ⊙ | Ex |
| 6-22 | Dye-sensitized solar cell 10 | D-1-21a | ⊙ | Ex |
| 6-23 | Dye-sensitized solar cell 11 | D-1-21a | ○ | Ex |
| 6-24 | Dye-sensitized solar cell 12 | D-1-21a | ○ | Ex |
| 6-25 | Dye-sensitized solar cell 1 | Sensitizing dye A | Δ | C Ex |
| 6-26 | Dye-sensitized solar cell 2 | Sensitizing dye A | Δ | C Ex |
| 6-27 | Dye-sensitized solar cell 3 | Sensitizing dye A | Δ | C Ex |
| 6-28 | Dye-sensitized solar cell 4 | Sensitizing dye A | Δ | C Ex |
| 6-29 | Dye-sensitized solar cell 5 | Sensitizing dye A | Δ | C Ex |
| 6-30 | Dye-sensitized solar cell 6 | Sensitizing dye A | Δ | C Ex |
| 6-31 | Dye-sensitized solar cell 7 | Sensitizing dye A | Δ | C Ex |
| 6-32 | Dye-sensitized solar cell 8 | Sensitizing dye A | Δ | C Ex |
| 6-33 | Dye-sensitized solar cell 9 | Sensitizing dye A | Δ | C Ex |
| 6-34 | Dye-sensitized solar cell 10 | Sensitizing dye A | Δ | C Ex |
| 6-35 | Dye-sensitized solar cell 11 | Sensitizing dye A | X | C Ex |
| 6-36 | Dye-sensitized solar cell 12 | Sensitizing dye A | X | C Ex |
| 6-37 | Dye-sensitized solar cell 1 | Sensitizing dye B | X | C Ex |
| 6-38 | Dye-sensitized solar cell 2 | Sensitizing dye B | Δ | C Ex |
| 6-39 | Dye-sensitized solar cell 3 | Sensitizing dye B | X | C Ex |
| 6-40 | Dye-sensitized solar cell 4 | Sensitizing dye B | Δ | C Ex |
| 6-41 | Dye-sensitized solar cell 5 | Sensitizing dye B | X | C Ex |
| 6-42 | Dye-sensitized solar cell 6 | Sensitizing dye B | X | C Ex |
| 6-43 | Dye-sensitized solar cell 7 | Sensitizing dye B | X | C Ex |
| 6-44 | Dye-sensitized solar cell 8 | Sensitizing dye B | X | C Ex |
| 6-45 | Dye-sensitized solar cell 9 | Sensitizing dye B | X | C Ex |
| 6-46 | Dye-sensitized solar cell 10 | Sensitizing dye B | X | C Ex |
| 6-47 | Dye-sensitized solar cell 11 | Sensitizing dye B | X | C Ex |
| 6-48 | Dye-sensitized solar cell 12 | Sensitizing dye B | X | C Ex |
| 6-49 | Dye-sensitized solar cell 1 | Sensitizing dye C | Δ | C Ex |
| 6-50 | Dye-sensitized solar cell 2 | Sensitizing dye C | Δ | C Ex |
| 6-51 | Dye-sensitized solar cell 3 | Sensitizing dye C | Δ | C Ex |
| 6-52 | Dye-sensitized solar cell 4 | Sensitizing dye C | Δ | C Ex |
| 6-53 | Dye-sensitized solar cell 5 | Sensitizing dye C | Δ | C Ex |
| 6-54 | Dye-sensitized solar cell 6 | Sensitizing dye C | Δ | C Ex |
| 6-55 | Dye-sensitized solar cell 7 | Sensitizing dye C | Δ | C Ex |
| 6-56 | Dye-sensitized solar cell 8 | Sensitizing dye C | Δ | C Ex |
| 6-57 | Dye-sensitized solar cell 9 | Sensitizing dye C | Δ | C Ex |
| 6-58 | Dye-sensitized solar cell 10 | Sensitizing dye C | Δ | C Ex |
| 6-59 | Dye-sensitized solar cell 11 | Sensitizing dye C | Δ | C Ex |
| 6-60 | Dye-sensitized solar cell 12 | Sensitizing dye C | X | C Ex |

"Ex" means Example according to this invention.
"C Ex" means Comparative Example.

Table 6 shows that the photoelectrochemical cell prepared by using the metal complex dye of the present invention has a passable level of conversion efficiency. Whereas, when the comparative dye was used, the conversion efficiency was low.

Experiment 7

A metal alkoxide was added to the metal oxide fine particles, and the mixture was made into a slurry. The slurry was applied on a conductive substrate, and then the slurry was subjected to irradiation with UV ozone, irradiation with UV and/or drying, and thus electrodes were produced. Thereafter, photoelectrochemical cells were produced, and the conversion efficiencies were measured.

(Metal Oxide Fine Particles)

Titanium oxide was used for the metal oxide fine particles. As the titanium oxide, P25 powder (manufactured by Degussa GmbH, trade name) which is composed of 30% of the rutile type and 70% of the anatase type on a mass basis, and has an average particle size of 25 nm, was used.

(Pretreatment of Metal Oxide Fine Particle Powder)

The metal oxide fine particles were heat-treated in advance, and thereby organic materials and moisture on the surface were eliminated. In the case of titanium oxide fine particles, the particles were heated for 30 minutes in an oven at 450° C. in open air.

(Measurement of Amount of Moisture Contained in Metal Oxide Fine Particles)

The amounts of moisture contained in the titanium oxide and the P25 powder (manufactured by Degussa GmbH, trade name), which had been stored in an environment at a temperature of 26° C. and a humidity of 72%, were quantitatively measured by weight reduction during thermal weight measurement and by Karl Fischer titration of the amount of moisture desorbed when heated to 300° C.

The amounts of moisture desorbed when titanium oxide and the P25 powder (manufactured by Degussa GmbH, trade name) were heated to 300° C., were quantitatively measured by Karl Fischer titration, and 0.253 mg of water was contained in 0.1033 g of a titanium oxide fine powder. More specifically, the titanium oxide fine powder contained about 2.5 wt % of moisture. The metal oxide fine particle powder was heat treated for 30 minutes, and then stored in a desiccators, and used.

(Preparation of Metal Alkoxide Paste)

As the metal alkoxide that plays the role of binding the metal oxide fine particles, titanium (IV) tetraisopropoxide (TTIP) as a titanium raw material, zirconium (IV) tetra-n-propoxide as a zirconium raw material, and niobium (V) pentaethoxide as a niobium raw material (all manufactured by Sigma-Aldrich Company) were used.

The molar concentration ratio of the metal oxide fine particles and the metal alkoxide was appropriately adjusted in accordance with the metal oxide fine particle diameter, so that the amorphous layer produced as a result of hydrolysis of the metal alkoxide would not become excessively thick, and binding between the particles could be sufficiently achieved. The metal alkoxides were all used in the form of a 0.1 M ethanol solution. In the case of mixing the titanium oxide fine particles and titanium (IV) tetraisopropoxide (TTIP), 3.55 g of a 0.1 M TTIP solution was mixed with 1 g of the titanium oxide fine particles. At this time, the concentration of titanium oxide in the paste thus obtained was about 22% by mass, and the paste had a viscosity appropriate for application. Furthermore, at this time, the ratio of titanium oxide, TTIP and ethanol was 1:0.127:3.42 on a mass basis, and 1:0.036:5.92 on a molar basis.

Similarly, mixed pastes of titanium oxide fine particles and alkoxides other than TTIP were also prepared such that the concentration of the fine particles was 22% by mass. In the paste which used zinc oxide and tin oxide fine particles, the concentration of the fine particles was set to 16% by mass. In the case of zinc oxide and tin oxide, the metal alkoxide solution was mixed at a ratio of 5.25 g to 1 g of the metal oxide fine particles.

The metal oxide fine particles and the metal alkoxide solution were stirred with a magnetic stirrer for 2 hours in a sealed container, and thus a uniform paste was obtained. In regard to the method of applying the paste on a conductive substrate, a doctor blade method, a screen printing method, a spray coating method or the like can be used, and an appropriate paste viscosity was appropriately selected according to the application method. In this embodiment, a method of applying the paste with a glass rod (similar to the doctor blade method) was conveniently used. In this case, the concentration of the metal oxide fine particles that resulted in an appropriate paste viscosity was approximately in the range of 5% to 30% by mass.

The thickness of the layer of amorphous metal oxide that was produced as a result of decomposition of the metal alkoxide was in the range of about 0.1 to 0.6 nm in the present Example, and could be adjusted in an appropriate range.

(Application and Air Drying Treatment of Paste on Conductive Substrate)

On a polyethylene terephthalate (PET) film substrate attached with a tin-doped indium oxide (ITO) conductive film (20 $\Omega/cm^2$) or on a glass substrate attached with a fluorine-doped tin oxide (FTO) conductive film (10 $\Omega/cm^2$), two sheets of adhesive tape were adhered in parallel at a certain distance as spacers, and each of the pastes prepared according to the methods described above was uniformly applied on the substrate using a glass rod.

After the paste was applied, a porous film was produced, prior to dye adsorption, by changing the conditions on the presence or absence of a UV ozone treatment, a UV irradiation treatment and/or a drying treatment.

(Drying Treatment)

The film obtained after the application on the conductive substrate was air dried in open air at room temperature for about 2 minutes. During this process, the metal alkoxides in the pastes were hydrolyzed due to the moisture in air, and titanium oxide, zirconium oxide, and niobium oxide, all being amorphous, were formed respectively from Ti alkoxide, Zr alkoxide, and Nb alkoxide.

Since the amorphous metal oxides thus produced accomplished the role of adhering metal oxide fine particles to other metal oxide fine particles, and adhering the film to the conductive substrate, porous films having excellent mechanical strength and adhesiveness were obtained only by air drying.

(UV Ozone Treatment)

A UV ozone cleaner, NL-UV253, manufactured by Nippon Laser Electronics Lab Co., Ltd. was used for the UV ozone treatment. The UV light source included three 4.5-W mercury lamps each having emission lines at 185 nm and 254 nm, and the sample was disposed horizontally at a distance of about 6.5 cm from the light source. When an oxygen gas stream is introduced into the chamber, ozone is generated. In the present Example, this UV ozone treatment was carried out for 2 hours. No decrease was observed in the conductivity of the ITO film and the FTO film due to this UV ozone treatment.

(UV Treatment)

The UV treatment was carried out for 2 hours in the same manner as in the UV ozone treatment, except that the treatment was performed by purging the chamber with nitrogen. No decrease was observed in the conductivity of the ITO film and the FTO film due to this UV treatment.

(Dye Adsorption)

For the dye, a 0.5 mM ethanol solution was prepared using each of the dyes described in Table 7. In the present experiment, a porous film produced by the process described above was dried for one hour in an oven at 100° C., and then was immersed in a solution of the sensitizing dye. The porous film was left immersed at room temperature for 50 minutes, so that the dye was adsorbed on the surface of titanium oxide. The sample after the adsorption of the dye was washed with ethanol and was air dried.

(Production of Photoelectrochemical Cell and Evaluation of Cell Characteristics)

The conductive substrate in which a porous film was formed after dye adsorption was used as a photoelectrode, and this photoelectrode and an ITO/PET film or FTO/glass counter electrode which had been modified with platinum fine particles by sputtering, were arranged to face each other. Thus, a photoelectrochemical cell was produced. The effective area of the photoelectrode was adjusted to about 0.2 cm$^2$. A 3-methoxypropionitrile solution containing 0.5M LiI, 0.05M I$_2$, and 0.5M t-butylpyridine was used as an electrolyte solution, and this solution was introduced into the gap between the two electrodes by means of the capillary phenomenon.

The evaluation of the cell performance was carried out by the measurement of a photocurrent action spectrum under irradiation with a definite number of photons (10$^{16}$ cm$^{-2}$), and by I-V measurement under irradiation with AM1.5 pseudo-sunlight (100 mW/cm$^2$). These measurements were carried out using a CEP-2000 type spectral response measurement apparatus manufactured by Bunkoukeiki Co., Ltd., to evaluate the conversion efficiency. The results are presented such that one having a conversion efficiency of 5.0% or more is indicated with "⊙"; one having a conversion efficiency of equal to or more than 4.5% and less than 5.0% is indicated with "○"; one having a conversion efficiency of equal to or more than 4.0% and less than 4.5% is indicated with "Δ"; and one having a conversion efficiency of less than 4.0% is indicated with "x". One having a conversion efficiency equal to or more than 4.5% was deemed to be passable.

TABLE 7

| Sample No. | TCO substrate (*1) | TiO$_2$ | Metal complex dye | UV | UV ozone | Drying | Conversion efficiency (%) | Remarks |
|---|---|---|---|---|---|---|---|---|
| 7-1 | FTO/GL | Conducted | D-1-1a | ○ | X | ○ | ⊙ | This invention |
| 7-2 | FTO/GL | Conducted | D-1-1a | X | ○ | ○ | ⊙ | This invention |
| 7-3 | FTO/GL | Conducted | D-1-1a | X | X | ○ | ○ | This invention |
| 7-4 | FTO/GL | Conducted | D-1-1a | X | X | X | ○ | This invention |
| 7-5 | FTO/GL | Not conducted | D-1-1a | X | X | ○ | ○ | This invention |
| 7-6 | FTO/GL | Conducted | D-1-1a | ○ | X | ○ | ○ | This invention |
| 7-7 | ITO/PET | Conducted | D-1-1a | ○ | X | ○ | ⊙ | This invention |
| 7-8 | ITO/PET | Conducted | D-1-1a | X | X | ○ | ○ | This invention |
| 7-9 | FTO/GL | Conducted | D-1-21a | ○ | X | ○ | ⊙ | This invention |
| 7-10 | FTO/GL | Conducted | D-1-21a | X | ○ | ○ | ⊙ | This invention |
| 7-11 | FTO/GL | Conducted | D-1-21a | X | X | ○ | ○ | This invention |
| 7-12 | FTO/GL | Conducted | D-1-21a | X | X | X | ○ | This invention |
| 7-13 | FTO/GL | Not conducted | D-1-21a | X | X | ○ | ○ | This invention |
| 7-14 | FTO/GL | Conducted | D-1-21a | ○ | X | ○ | ○ | This invention |
| 7-15 | ITO/PET | Conducted | D-1-21a | ○ | X | ○ | ⊙ | This invention |
| 7-16 | ITO/PET | Conducted | D-1-21a | X | X | ○ | ○ | This invention |
| 7-17 | FTO/GL | Conducted | Sensitizing dye A | ○ | X | ○ | Δ | Comparative example |
| 7-18 | FTO/GL | Conducted | Sensitizing dye A | X | ○ | ○ | Δ | Comparative example |
| 7-19 | FTO/GL | Conducted | Sensitizing dye A | X | X | ○ | Δ | Comparative example |
| 7-20 | FTO/GL | Conducted | Sensitizing dye A | X | X | X | Δ | Comparative example |
| 7-21 | FTO/GL | Not conducted | Sensitizing dye A | X | X | ○ | X | Comparative example |
| 7-22 | FTO/GL | Conducted | Sensitizing dye A | ○ | X | ○ | X | Comparative example |
| 7-23 | ITO/PET | Conducted | Sensitizing dye A | ○ | X | ○ | Δ | Comparative example |
| 7-24 | ITO/PET | Conducted | Sensitizing dye A | X | X | ○ | X | Comparative example |
| 7-25 | FTO/GL | Conducted | Sensitizing dye B | ○ | X | ○ | X | Comparative example |
| 7-26 | FTO/GL | Conducted | Sensitizing dye B | X | ○ | ○ | X | Comparative example |
| 7-27 | FTO/GL | Conducted | Sensitizing dye B | X | X | ○ | X | Comparative example |
| 7-28 | FTO/GL | Conducted | Sensitizing dye B | X | X | X | Δ | Comparative example |
| 7-29 | FTO/GL | Not conducted | Sensitizing dye B | X | X | ○ | X | Comparative example |
| 7-30 | FTO/GL | Conducted | Sensitizing dye B | ○ | X | ○ | X | Comparative example |
| 7-31 | ITO/PET | Conducted | Sensitizing dye B | ○ | X | ○ | Δ | Comparative example |
| 7-32 | ITO/PET | Conducted | Sensitizing dye B | X | X | ○ | X | Comparative example |
| 7-33 | FTO/GL | Conducted | Sensitizing dye C | ○ | X | ○ | Δ | Comparative example |
| 7-34 | FTO/GL | Conducted | Sensitizing dye C | X | ○ | ○ | Δ | Comparative example |
| 7-35 | FTO/GL | Conducted | Sensitizing dye C | X | X | ○ | X | Comparative example |
| 7-36 | FTO/GL | Conducted | Sensitizing dye C | X | X | X | Δ | Comparative example |
| 7-37 | FTO/GL | Not conducted | Sensitizing dye C | X | X | ○ | Δ | Comparative example |
| 7-38 | FTO/GL | Conducted | Sensitizing dye C | ○ | X | ○ | X | Comparative example |
| 7-39 | ITO/PET | Conducted | Sensitizing dye C | ○ | X | ○ | Δ | Comparative example |
| 7-40 | ITO/PET | Conducted | Sensitizing dye C | X | X | ○ | Δ | Comparative example |

(*1): GL: Glass

In Table 7, the columns for the items "UV ozone", "UV" and "Drying" represent the presence or absence of the UV ozone treatment, UV irradiation treatment and drying treatment, respectively, after the formation of the porous film and before the adsorption of the sensitizing dye. Treated samples are indicated with "○", and untreated samples are indicated with "x".

The column for the item "Pre-treatment of TiO$_2$" in Table 7 represents the presence or absence of a pretreatment (heat treatment for 30 minutes in an oven at 450° C.) of the titanium oxide fine particles. Samples 7-6, 7-14, 7-22, 7-30 and 7-38 represent samples obtained by using a paste with a high TTIP concentration (the molar ratio of titanium oxide:TTIP was 1:0.356). The other samples (samples 7-1 to 7-5, 7-7 to 7-13, 7-23 to 7-29, 7-31 to 7-37, 7-39 and 7-40) were all obtained by using a paste having a molar ratio of titanium oxide:TTIP of 1:0.0356.

Table 7 shows that the photoelectrochemical cell prepared by using the metal complex dye of the present invention consistently had a higher conversion efficiency of the photoelectrochemical cell, as compared with the case where the dye was used alone, and a passable level of conversion efficiency was achieved, irrespective of presence or absence of the UV ozone treatment, UV irradiation treatment, or drying treatment, before the adsorption of the sensitizing dye and after the formation of the porous film.

Whereas, when the comparative dye was used, the conversion efficiency was found to be low.

Experiment 8

An electrolyte solution in which 0.1 mol/L of lithium iodide, 0.05 mol/L of iodine, and 0.62 mol/L of dimethylpropylimidazolium iodide were dissolved was prepared using acetonitrile as a solvent. To this solution, the benzimidazole-based compounds of No. 1 to No. 8 shown below were separately added so as to be a concentration of 0.5 mol/L each, and the compounds were dissolved therein.

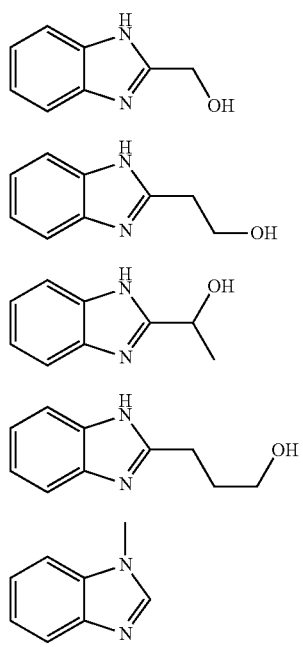

No. 1

No. 2

No. 3

No. 4

No. 5

-continued

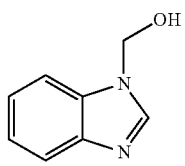

No. 6

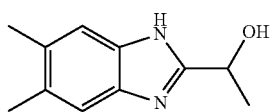

No. 7

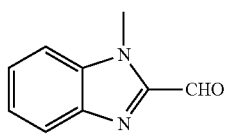

No. 8

Electrolyte solutions of the benzimidazole-based compounds of No. 1 to No. 8 each were added dropwise to a porous titanium oxide semiconductor thin film (thickness 15 μm) with an electrically conductive glass plate on which the metal complex dye of the present invention was carried. A frame type spacer (thickness 25 μm) made of a polyethylene film was mounted thereon, and this spacer was covered with a platinum counter electrode. Thus, a photoelectric conversion element was produced.

Photoelectric conversion elements thus obtained were irradiated with light at an intensity of 100 mW/cm$^2$ using a Xe lamp as a light source. The open circuit voltages and photoelectric conversion efficiencies thus obtained are shown in Table 8. The results are presented such that one having an open circuit voltage of 0.75 V or more is indicated with "⊙"; one having an open circuit voltage of equal to or more than 0.70 V and less than 0.75 is indicated with "○"; one having an open circuit voltage of equal to or more than 0.65 V and less than 0.70 V is indicated with "Δ"; and one having an open circuit voltage of less than 0.65 V is indicated with "x". Further, the results are presented such that one having a conversion efficiency of 7.5% or more is indicated with "⊙"; one having a conversion efficiency of equal to or more than 7.0% and less than 7.5% is indicated with "○"; one having a conversion efficiency of equal to or more than 6.5% and less than 7.0% is indicated with "Δ"; and one having a conversion efficiency of less than 6.5% is indicated with "x". One having an open circuit voltage equal to or more than 0.70 V, and a conversion efficiency equal to or more than 7.0% was deemed to be passable.

In addition, Table 8 also shows the results obtained with a photoelectric conversion element which used an electrolytic liquid without any added benzimidazole-based compound.

TABLE 8

| Sample No | Benzimidazole-based compound | Metal complex dye | Open circuit voltage/V (%) | Conversion efficiency | Remarks |
|---|---|---|---|---|---|
| 8-1 | No. 1 | D-1-1a | ⊙ | ⊙ | This invention |
| 8-2 | No. 2 | D-1-1a | ⊙ | ⊙ | This invention |
| 8-3 | No. 3 | D-1-1a | ⊙ | ⊙ | This invention |
| 8-4 | No. 4 | D-1-1a | ⊙ | ⊙ | This invention |
| 8-5 | No. 5 | D-1-1a | ⊙ | ⊙ | This invention |
| 8-6 | No. 6 | D-1-1a | ⊙ | ⊙ | This invention |
| 8-7 | No. 7 | D-1-1a | ○ | ⊙ | This invention |
| 8-8 | No. 8 | D-1-1a | ○ | ○ | This invention |
| 8-9 | None | D-1-1a | ○ | ○ | This invention |
| 8-10 | No. 1 | D-21-1a | ⊙ | ⊙ | This invention |

TABLE 8-continued

| Sample No | Benzimidazole-based compound | Metal complex dye | Open circuit voltage/V (%) | Conversion efficiency | Remarks |
|---|---|---|---|---|---|
| 8-11 | No. 2 | D-21-1a | ☉ | ☉ | This invention |
| 8-12 | No. 3 | D-21-1a | ☉ | ☉ | This invention |
| 8-13 | No. 4 | D-21-1a | ☉ | ☉ | This invention |
| 8-14 | No. 5 | D-21-1a | ☉ | ☉ | This invention |
| 8-15 | No. 6 | D-21-1a | ☉ | ☉ | This invention |
| 8-16 | No. 7 | D-21-1a | ○ | ☉ | This invention |
| 8-17 | No. 8 | D-21-1a | ○ | ○ | This invention |
| 8-18 | None | D-21-1a | ○ | ○ | This invention |
| 8-19 | No. 1 | Sensitizing dye A | Δ | Δ | Comparative example |
| 8-20 | No. 2 | Sensitizing dye A | Δ | Δ | Comparative example |
| 8-21 | No. 3 | Sensitizing dye A | Δ | Δ | Comparative example |
| 8-22 | No. 4 | Sensitizing dye A | X | X | Comparative example |
| 8-23 | No. 5 | Sensitizing dye A | Δ | Δ | Comparative example |
| 8-24 | No. 6 | Sensitizing dye A | Δ | Δ | Comparative example |
| 8-25 | No. 7 | Sensitizing dye A | Δ | Δ | Comparative example |
| 8-26 | No. 8 | Sensitizing dye A | Δ | Δ | Comparative example |
| 8-27 | None | Sensitizing dye A | X | X | Comparative example |
| 8-28 | No. 1 | Sensitizing dye B | X | X | Comparative example |
| 8-29 | No. 2 | Sensitizing dye B | X | X | Comparative example |
| 8-30 | No. 3 | Sensitizing dye B | Δ | Δ | Comparative example |
| 8-31 | No. 4 | Sensitizing dye B | X | X | Comparative example |
| 8-32 | No. 5 | Sensitizing dye B | Δ | Δ | Comparative example |
| 8-33 | No. 6 | Sensitizing dye B | X | X | Comparative example |
| 8-34 | No. 7 | Sensitizing dye B | Δ | Δ | Comparative example |
| 8-35 | No. 8 | Sensitizing dye B | X | Δ | Comparative example |
| 8-36 | None | Sensitizing dye B | X | X | Comparative example |
| 8-37 | No. 1 | Sensitizing dye C | Δ | Δ | Comparative example |
| 8-38 | No. 2 | Sensitizing dye C | Δ | Δ | Comparative example |
| 8-39 | No. 3 | Sensitizing dye C | X | Δ | Comparative example |
| 8-40 | No. 4 | Sensitizing dye C | Δ | Δ | Comparative example |
| 8-41 | No. 5 | Sensitizing dye C | Δ | Δ | Comparative example |
| 8-42 | No. 6 | Sensitizing dye C | Δ | Δ | Comparative example |
| 8-43 | No. 7 | Sensitizing dye C | Δ | Δ | Comparative example |
| 8-44 | No. 8 | Sensitizing dye C | Δ | Δ | Comparative example |
| 8-45 | None | Sensitizing dye C | X | X | Comparative example |

Table 8 shows that any of the photoelectric conversion elements prepared by using the metal complex dyes of the present invention had a passable level of the open circuit voltage and the conversion efficiency.

Whereas, when the comparative dye was used, the open circuit voltage and the conversion efficiency were found to be low.

Experiment 9

Dye-sensitized solar cells <1> to <4> were produced according to the following methods. In these dye-sensitized solar cells, sample Nos. 9-1 to 9-20 were obtained by allowing the metal complex dyes shown in the following Table 9 to adsorb thereon.

(Dye-Sensitized Solar Cell <1>)

A photoelectrode having the same configuration as that of the photoelectrode 10 shown in FIG. 1 described in JP-A-2004-152613 (provided that the semiconductor electrode 2 was made to have a bilayer structure), was produced by the procedure shown below. Further, a dye-sensitized solar cell (area of the light-receiving surface F2 of the semiconductor electrode 2: 1 cm$^2$) having the same configuration as that of the dye-sensitized solar cell 20 shown in FIG. 1 described in JP-A-2004-152613, except for the use of the above-described photoelectrode, was produced. In regard to the respective layers of the semiconductor electrode 2 having a bilayer structure, the layer disposed closer to the transparent electrode 1 is referred to as a "first layer", and the layer disposed closer to the porous substance layer PS is referred to as a "second layer".

First, P25 powder having an average particle diameter of 25 nm (manufactured by Degussa GmbH, trade name), and titanium oxide particles having a different particle size, P200 powder (average particle diameter: 200 nm, manufactured by Degussa GmbH, trade name), were used; and acetylacetone, ion-exchanged water, and a surfactant (manufactured by Tokyo Chemical Industry Co., Ltd.; trade name: Triton-X) were added to those powders and kneaded, such that the total content of P25 and P200 was 15% by mass, and the mass ratio of P25 and P200 was P25:P200=30:70. Thus, a slurry for second layer formation (hereinafter, referred to as "slurry 1") was prepared.

Next, a slurry for first layer formation (content of P1: 15% by mass; hereinafter, referred to as "slurry 2") was prepared by the same production procedure as that used for the slurry 1, except that only P25 was used, without using P200.

Meanwhile, a transparent electrode (thickness: 1.1 mm) in which a fluorine-doped SnO$_2$ conductive film (thickness: 700 nm) was formed on a glass substrate (transparent conductive glass), was prepared. The slurry 2 described above was applied on this SnO$_2$ conductive film with a bar coater, and subsequently, the slurry 2 was dried. Thereafter, the slurry 2 was calcined at 450° C. for 30 minutes in air. In this manner, a first layer of the semiconductor electrode 2 was formed on the transparent electrode.

Furthermore, a second layer was formed on the first layer by using the slurry 1 and repeating application and calcination as described above. In this manner, a semiconductor electrode 2 (area of light-receiving surface: 1.0 cm$^2$, total thickness of the first layer and the second layer: 10 μm (thickness of the first layer: 3 μm, thickness of the second layer: 7 μm)) was formed on the SnO$_2$ conductive film, and thus a photoelectrode 10 not containing any sensitizing dye, was produced.

Next, an ethanol solution of each of the dye described in Table 9 (concentration of sensitizing dye: $3\times10^{-4}$ mol/L) was prepared as the dye. The photoelectrode 10 was immersed in this solution, and the photoelectrode was left immersed for 20 hours under the conditions of a temperature of 80° C. Thereby, the dye was adsorbed to the interior of the semiconductor electrode in an amount of about $1.0\times10^{-7}$ mol/cm$^2$.

Next, a counter electrode CE having the same shape and size as the photoelectrode was produced. First, an isopropanol solution of chloroplatinic acid hexahydrate was added dropwise on a transparent conductive glass, dried in air, and then was calcination treated for 30 minutes at 450° C. Thus, a platinum sintered counter electrode CE was obtained. This counter electrode CE was provided in advance with a hole (diameter 1 mm) for the injection of an electrolyte E.

Next, zinc iodide, 1,2-dimethyl-3-propylimidazolium iodide, iodine, and 4-tert-butylpyridine were dissolved in methoxyacetonitrile, which served as a solvent, and thereby a liquid electrolyte (concentration of zinc iodide: 10 mmol/L, concentration of dimethylpropylimidazolium iodide: 0.6 mol/L, concentration of iodine: 0.05 mol/L, and concentration of 4-tert-butylpyridine: 1 mol/L) was prepared.

Subsequently, a spacer S (trade name: "Himilan", an ethylene/methacrylic acid random copolymer ionomer film) manufactured by Mitsui-DuPont Polychemical, Ltd., which had a shape matching the size of the semiconductor electrode, was prepared, and as shown in FIG. 1 described in JP-A-2004-152613, the photoelectrode and the counter electrode were arranged to face each other, with the spacer interposed therebetween. The electrodes were respectively pasted by heat fusion. Thus, a casing of a cell (not filled with an electrolyte) was obtained.

Subsequently, the liquid electrolyte was injected into the case through the hole on the counter electrode, and then the hole was closed with a member made of the same material as the spacer. This member was further thermally fused to the hole of the counter electrode to seal the hole. Thus, a dye-sensitized solar cell <1> was completed.

(Dye-Sensitized Solar Cell <2>)

A dye-sensitized solar cell <2> was produced by the same procedure and the same conditions as in the case of the dye-sensitized solar cell <1>, except that the concentration of zinc iodide in the liquid electrolyte was changed to 50 mmol/L.

(Dye-Sensitized Solar Cell <3>)

A dye-sensitized solar cell <3> was produced by the same procedure and the same conditions as in the case of the dye-sensitized solar cell <1>, except that lithium iodide was added instead of zinc iodide in the liquid electrolyte, and the concentration of lithium iodide in the liquid electrolyte was changed to 20 mmol/L.

(Dye-Sensitized Solar Cell <4>)

A dye-sensitized solar cell <4> was produced by the same procedure and the same conditions as in the case of the dye-sensitized solar cell <1>, except that lithium iodide was added instead of zinc iodide in the liquid electrolyte, and the concentration of lithium iodide in the liquid electrolyte was changed to 100 mmol/L.

[Cell Characteristics Evaluation Test]

The photoelectric conversion efficiencies ($\eta$ (%)) of the dye-sensitized solar cells of the sample Nos. 9-1 to 9-20 described in the following Table 9 were measured by performing the cell characteristics evaluation tests according to the following procedures.

The cell characteristics evaluation test was carried out using a solar simulator (manufactured by Wacom Electric Co., Ltd., trade name: "WXS-85-H type"), under the measurement conditions in which the condition for irradiation with pseudo-sunlight from a xenon lamp light source through an AM filter (AM1.5) was set at 100 mW/cm$^2$ (irradiation condition of so-called "1 Sun").

For each of the dye-sensitized solar cells of the sample Nos. 9-1 to 9-20, the current-voltage characteristics were measured at room temperature using an I-V tester, and the photoelectric conversion efficiency $\eta$ [%] was determined from these characteristics. The results thus obtained are indicated in Table 9 (irradiation conditions for 1 Sun). Furthermore, values of reduction ratio in photoelectric conversion efficiency ($\eta$ (%)) after a lapse of 300 hours at 80° C. in a dark place are also shown in Table 9.

TABLE 9

| | | | Conversion efficiency (%) | | |
|---|---|---|---|---|---|
| Sample No. | Dye-sensitized solar cell No. (*1) | Metal complex dye | Initial value | Reduction ratio after storage in dark place | Remarks |
| 9-1 | <1> | D-1-1a | 7.7 | 4 | This invention |
| 9-2 | <2> | D-1-1a | 7.7 | 4 | This invention |
| 9-3 | <3> | D-1-1a | 7.8 | 6 | This invention |
| 9-4 | <4> | D-1-2a | 7.7 | 7 | This invention |
| 9-5 | <1> | D-1-21a | 7.6 | 4 | This invention |
| 9-6 | <2> | D-1-21a | 7.5 | 5 | This invention |
| 9-7 | <3> | D-1-21a | 7.5 | 7 | This invention |
| 9-8 | <4> | D-1-21a | 7.4 | 8 | This invention |
| 9-9 | <1> | Sensitizing dye A | 6.6 | 28 | Comparative example |
| 9-10 | <2> | Sensitizing dye A | 6.4 | 26 | Comparative example |
| 9-11 | <3> | Sensitizing dye A | 6.6 | 47 | Comparative example |
| 9-12 | <4> | Sensitizing dye A | 6.5 | 53 | Comparative example |
| 9-13 | <1> | Sensitizing dye B | 5.4 | 16 | Comparative example |
| 9-14 | <2> | Sensitizing dye B | 5.1 | 16 | Comparative example |
| 9-15 | <3> | Sensitizing dye B | 5.2 | 18 | Comparative example |
| 9-16 | <4> | Sensitizing dye B | 5.3 | 18 | Comparative example |
| 9-17 | <1> | Sensitizing dye C | 6.6 | 14 | Comparative example |
| 9-18 | <2> | Sensitizing dye C | 6.4 | 13 | Comparative example |
| 9-19 | <3> | Sensitizing dye C | 6.6 | 15 | Comparative example |
| 9-20 | <4> | Sensitizing dye C | 6.5 | 17 | Comparative example |

*1: The number of the dye-sensitized solar cell

As is clear from the results presented in Table 9, the dyes of the present invention were found to show a high conversion efficiency, even when zinc iodide was added to the electrolyte. Whereas, the dye-sensitized solar cell prepared by using the comparative dye was found to have a decreased conversion efficiency after a lapse of 300 hours.

Experiment 10

1. Preparation of Titanium Dioxide Dispersion Liquid

In a stainless steel vessel having an internal capacity of 200 mL and having the inside coated with a fluororesin, 15 g of titanium dioxide fine particles (manufactured by Nippon Aerosil Co., Ltd., Degussa P-25), 45 g of water, 1 g of a dispersant (manufactured by Sigma-Aldrich Company, Triton X-100), and 30 g of zirconia beads having a diameter of 0.5 mm (manufactured by Nikkato Corp.) were placed, and the mixture was subjected to a dispersing treatment at 1500 rpm for 2 hours using a sand grinder mill (manufactured by Aimex, Ltd.). The zirconia beads were separated by filtration from the dispersion liquid thus obtained. The average particle diameter of the titanium dioxide fine particles in the dispersion liquid thus obtained was 2.5 μm. The particle diameter was measured using a Mastersizer (trade name) manufactured by Malvern Instruments, Ltd.

2. Production of Dye-Adsorbed Titanium Oxide Fine Particle Layer (Electrode A)

A conductive glass plate (manufactured by Asahi Glass Co., Ltd., TCO Glass-U, surface resistance: about 30 Ω/m$^2$) having a size of 20 mm×20 mm and coated with fluorine-doped tin oxide, was prepared, and an adhesive tape for use as a spacer was affixed at the two ends (areas having a width of 3 mm from the edge) on the conductive layer side. Subsequently, the dispersion liquid described above was applied on the conductive layer using a glass rod. After the application of the dispersion liquid, the adhesive tape was detached, and the dispersion liquid was air dried for one day at room temperature. Subsequently, this semiconductor-coated glass plate was placed in an electrical furnace (muffle furnace FP-32 type, manufactured by Yamato Scientific Co., Ltd.), and was calcined at 450° C. for 30 minutes. The semiconductor-applied glass plate was taken out and cooled, and then the glass plate was immersed in an ethanol solution of the dye indicated in Table 10 (concentration: 3×10$^{-4}$ mol/L) for 3 hours. The semiconductor-applied glass plate adsorbed with the dye was immersed in 4-tert-butylpyridine for 15 minutes, subsequently washed with ethanol, and naturally dried, to obtain a dye-sensitized titanium oxide fine particle layer. The thickness of the dye-sensitized titanium oxide fine particle layer thus obtained was 10 μm, and the application amount of the titanium oxide fine particles was 20 g/m$^2$. The amount of adsorption of the dye varied in the range of 0.1 to 10 mmol/m$^2$, in accordance with the type of the dye.

3. Production of Dye-Sensitized Solar Cell

Three types of dye-sensitized solar cells a to c were produced according to the following methods. In these dye-sensitized solar cells, sample Nos. 10-1 to 10-15 were obtained using the metal complex dyes, the nitrogen-containing polymer, and the electrophile shown in the following Table 10.

(A) Production of Dye-Sensitized Solar Cell A

A mixture of acetonitrile and 3-methyl-2-oxazolidinone at a volume ratio of 90/10 was used as the solvent. Iodine and an iodine salt of 1-methyl-3-hexylimidazolium as an electrolyte salt were added to this solvent, and thus a solution containing 0.5 mol/L of the electrolyte salt and 0.05 mol/L of iodine was prepared. To this solution, 10 parts by mass of a nitrogen-containing polymer compound (a) was added relative to 100 parts by mass of a mixture of (solvent+nitrogen-containing polymer compound+salt). Furthermore, an electrophile (β) for the reactive nitrogen atoms of the nitrogen-containing polymer compound was mixed in an amount of 0.1 moles, and thus a uniform reaction solution was obtained.

On the other hand, a counter electrode formed from a glass plate deposited with platinum was disposed, with the platinum thin film side facing downward, on the dye-sensitized titanium oxide fine particle layer formed on the conductive glass plate, with a spacer interposed between the two plates, and thereby the conductive glass plate and the platinum-deposited glass plate were fixed. An open end of the assembly thus obtained was immersed in the electrolyte solution described above, and thus the reaction solution was caused to penetrate into the dye-sensitized titanium oxide fine particle layer by the capillary phenomenon.

Subsequently, the assembly was heated at 80° C. for 30 minutes, and thereby a crosslinking reaction was carried out. In this manner, a dye-sensitized solar cell a-1 (Sample No. 10-1) of the present invention was obtained, in which a dye-sensitized titanium oxide fine particle layer 20, an electrolyte layer 30, and a counter electrode 40 formed from a platinum thin film 42 and a glass plate 41 were laminated in this order on a conductive layer 12 of a conductive glass plate 10 as shown in FIG. 2 described in JP-A-2000-323190.

Furthermore, dye-sensitized solar cells a-2 to a-5 having a different photosensitive layer 20 and/or a different charge transport layer 30 were obtained by repeating the steps described above, except that the dye was changed as shown in Table 10.

(b) Dye-Sensitized Solar Cell b

An electrode A (20 mm×20 mm) formed from a titanium oxide fine particle layer which was dye-sensitized by a dye of the present invention as described above, was superimposed on a platinum-deposited glass plate having the same size, with a spacer interposed therebetween. Subsequently, an electrolytic liquid (a solution of 0.05 mol/L of iodine and 0.5 mol/L of lithium iodide in a mixture of acetonitrile and 3-methyl-2-oxazolidinone at a volume ratio of 90/10 as a solvent) was caused to penetrate into the gap between the two glass plates by utilizing the capillary phenomenon, and thus a dye-sensitized solar cell b-1 (Sample No. 10-2) was produced. Furthermore, dye-sensitized solar cells b-2 to b-5 were obtained by repeating the above steps except that the dye was changed as indicated in Table 10.

(C) Dye-Sensitized Solar Cell c (Electrolyte Described in JP-A-9-27352)

An electrolytic liquid was applied on the electrode A (20 mm×20 mm) formed from a titanium oxide fine particle layer which was dye-sensitized by a dye of the present invention as described above, and thus the electrode A was impregnated with the electrolytic liquid. The electrolytic liquid was obtained by dissolving 500 mg of lithium iodide in a mixed liquid containing 1 g of hexaethylene glycol methacrylate (manufactured by Nippon Oil & Fats Co., Ltd., Blenmer PE-350), 1 g of ethylene glycol, and 20 mg of 2-hydroxy-2-methyl-1-phenyl-propan-1-one (manufactured by Ciba-Geigy Japan, Ltd., Darocur 1173) as a polymerization initiator, and degassing the solution in a vacuum for 10 minutes.

Subsequently, the porous titanium oxide layer impregnated with the mixed solution was left under reduced pressure to remove air bubbles in the porous titanium oxide layer. Penetration of the monomer was accelerated and then the monomer was polymerized by irradiation with ultraviolet radiation, and thereby a uniform gel of a polymer compound was filled within the fine pores of the porous titanium oxide layer. The product thus obtained was exposed to an iodine atmosphere for 30 minutes to diffuse iodine into the polymer compound, and then a platinum-deposited glass plate was superimposed thereon. Thus, a dye-sensitized solar cell c-1 (Sample No. 10-3) was obtained. Furthermore, dye-sensitized solar cells c-2 to c-5 were obtained by repeating the steps described above, except that the dye was changed as indicated in Table 10.

5. Measurement of Photoelectric Conversion Efficiency

Pseudo-sunlight not containing ultraviolet rays was obtained by passing light from a 500-W xenon lamp (manufactured by Ushio, Inc.) through an AM1.5 filter (manufactured by Oriel Instruments Corp.) and a sharp cut filter (Kenko L-42). The light intensity was set at 89 mW/cm$^2$.

The conductive glass plate 10 and the platinum-deposited glass plate 40 of the photoelectrochemical cell were each connected to an alligator clip, and the respective alligator clips were connected to a current-voltage measurement device (Keithley SMU238 type (trade name)). This photoelectrochemical cell was irradiated with pseudo-sunlight from the side of the conductive glass plate 10, and the electricity thus generated was measured using the current-voltage measurement device. The initial values of the conversion efficiency ($\eta$) of the photoelectrochemical cells determined thereby, and the rates of decrease in conversion efficiency after storage for 300 hours in a dark place are summarized in Table 10. One having an initial value of the conversion efficiency equal to or more than 7.0% was deemed to be passable, and one have a reduction ratio in conversion efficiency after a lapse of 300 hours equal to or less than 7.0% was deemed to be passable.

(Remarks)
(1) The symbols of the dyes are as described in the detailed description of the invention.
(2) The nitrogen-containing polymer α and the electrophile β each represent the following compound.

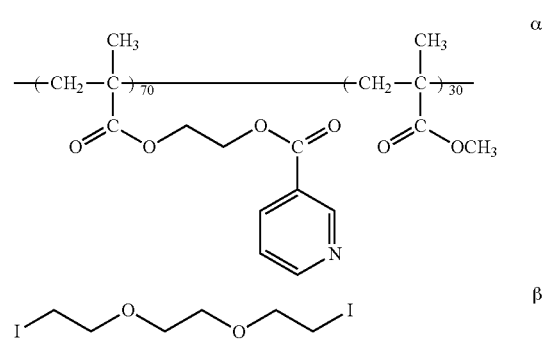

Table 10 shows that the photoelectrochemical cells prepared by using the dyes of the present invention each had a passable level of the initial values of conversion efficiencies, and further had an excellent durability in which a reduction ratio in conversion efficiency after a lapse of 300 hours is equal to or less than 7.0%.

Experiment 11

1. Preparation of Titanium Dioxide Dispersion Liquid

In a stainless steel vessel having an internal capacity of 200 mL and having the inside coated with a fluororesin, 15 g of titanium dioxide fine particles (manufactured by Nippon Aerosil Co., Ltd., Degussa P-25), 45 g of water, 1 g of a dispersant (manufactured by Sigma-Aldrich Company, Triton X-100), and 30 g of zirconia beads having a diameter of 0.5 mm (manufactured by Nikkato Corp.) were placed, and the mixture was subjected to a dispersing treatment at 1500

TABLE 10

| Sample No. | Dye-sensitized solar cell No. | Nitrogen-containing polymer | Electrophile | Metal complex dye | Conversion efficiency (%) Initial value | Reduction ratio after 300 h | Remarks |
|---|---|---|---|---|---|---|---|
| 10-1 | a-1 | α | β | D-1-1a | 7.8 | 2 | This invention |
| 10-2 | b-1 | None | None | D-1-1a | 7.4 | 6 | This invention |
| 10-3 | c-1 | None | None | D-1-1a | 7.2 | 4 | This invention |
| 10-4 | a-2 | α | β | D-1-16a | 7.4 | 3 | This invention |
| 10-5 | b-2 | None | None | D-1-16a | 7.2 | 7 | This invention |
| 10-6 | c-2 | None | None | D-1-16a | 7 | 4 | This invention |
| 10-7 | a-3 | α | β | Sensitizing dye A | 6.5 | 24 | Comparative example |
| 10-8 | b-3 | None | None | Sensitizing dye A | 6.3 | 68 | Comparative example |
| 10-9 | c-3 | None | None | Sensitizing dye A | 6.2 | 40 | Comparative example |
| 10-10 | a-4 | α | β | Sensitizing dye B | 5.5 | 12 | Comparative example |
| 10-11 | b-4 | None | None | Sensitizing dye B | 5.4 | 19 | Comparative example |
| 10-12 | c-4 | None | None | Sensitizing dye B | 5.3 | 14 | Comparative example |
| 10-13 | a-5 | α | β | Sensitizing dye C | 6.4 | 13 | Comparative example |
| 10-14 | b-5 | None | None | Sensitizing dye C | 6.5 | 15 | Comparative example |
| 10-15 | c-5 | None | None | Sensitizing dye C | 6.4 | 12 | Comparative example | rpm for 2 hours using a sand grinder mill (manufactured by Aimex, Ltd.). The zirconia beads were separated by filtration from the dispersion liquid thus obtained. The average particle diameter of the titanium dioxide fine particles in the dispersion liquid thus obtained was 2.5 μm. The particle diameter was measured using a Mastersizer (trade name) manufactured by Malvern Instruments, Ltd.

2. Production of Dye-Adsorbed Titanium Oxide Fine Particle Layer (Electrode A)

A conductive glass plate (manufactured by Asahi Glass Co., Ltd., TCO Glass-U, surface resistance: about 30 Ω/m²) having a size of 20 mm×20 mm and coated with fluorine-doped tin oxide, was prepared, and an adhesive tape for use as a spacer was affixed at the two ends (areas having a width of 3 mm from the edge) on the conductive layer side. Subsequently, the dispersion liquid described above was applied on the conductive layer using a glass rod. After the application of the dispersion liquid, the adhesive tape was detached, and the dispersion liquid was air dried for one day at room temperature. Subsequently, this semiconductor-coated glass plate was placed in an electrical furnace (muffle furnace FP-32 type, manufactured by Yamato Scientific Co., Ltd.), and was calcined at 450° C. for 30 minutes. The semiconductor-applied glass plate was taken out and cooled, and then the glass plate was immersed in an ethanol solution of the dye indicated in Table 11 (concentration: 3×10⁻⁴ mol/L) for 3 hours. The semiconductor-applied glass plate adsorbed with the dye was immersed in 4-tert-butylpyridine for 15 minutes, subsequently washed with ethanol, and naturally dried, to obtain a dye-adsorbed titanium oxide fine particle layer (electrode A). The thickness of the dye-sensitized titanium oxide fine particle layer of electrode A thus obtained was 10 μm, and the application amount of the titanium oxide fine particles was 20 g/m². The amount of adsorption of the dye varied in the range of 0.1 to 10 mmol/m², in accordance with the type of the dye.

3. Production of Dye-Sensitized Solar Cell

The dye-sensitized electrode A (20 mm×20 mm) prepared as described above was superposed on a platinum-deposited glass plate having a size same therewith. Next, an electrolyte composition was infiltrated into a clearance between both glass plates utilizing a capillary phenomenon, and an electrolyte was introduced into a titanium oxide electrode. Thus, as shown in FIG. 1, a dye-sensitized solar cell was produced in which an electrically conductive support 1 composed of an electrically conductive glass plate (an electrically conductive layer being placed on a glass transparent substrate), a photoconductor 2, a charge transfer object 3, a counter electrode 4 composed of platinum, and a glass transparent substrate (not shown) were laminated in this order, and sealed with an epoxy-based sealant. When the viscosity of the electrolyte composition was high, and infiltration of the electrolyte composition utilizing the capillary phenomenon was difficult, the dye-sensitized solar cell was produced in a similar manner by warming the electrolyte composition to 50° C., applying the composition to a titanium oxide electrode, and then placing this electrode under reduced pressure, and by superposing the platinum-deposited glass plate (counter electrode) after the electrolyte composition was sufficiently permeated and air in the electrode was released.

Dye-sensitized solar cells of sample Nos. 11-1 to 11-10 were produced according to the above-described process by changing dyes. As the electrolyte composition used for each dye-sensitized solar cell, one containing 98% by mass of the following heterocyclic quaternary salt compound, and 2% by mass of iodine was used.

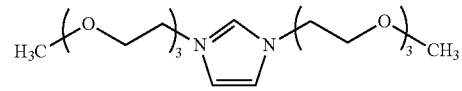

4. Measurement of Photoelectric Conversion Efficiency

Pseudo-sunlight not containing ultraviolet rays was obtained by passing light from a 500-W xenon lamp (manufactured by Ushio, Inc.) through an AM1.5 filter (manufactured by Oriel Instruments Corp.) and a sharp cut filter (Kenko L-37). The light intensity was set at 70 mW/cm². The dye-sensitized solar cell was irradiated with this pseudo-sunlight at 50° C., and the thus generated electricity was measured using a current-voltage measurement device (Keithley SMU238 type). The reduction ratio in conversion efficiency after storage at 85° C. for 1,000 hours in a dark place, and the reduction ratio in conversion efficiency after continuous light irradiation for 500 hours were also measured. The results are shown in the following Table 11.

TABLE 11

| Sample No. | Dye | Conversion efficiency | Reduction ratio of conversion efficiency after storage in dark place (%) | Reduction ratio of conversion efficiency after continuous light irradiation (%) | Remarks |
|---|---|---|---|---|---|
| 11-1 | D-1-1a | 7.4 | 5 | 8 | This invention |
| 11-2 | D-1-21a | 7.4 | 6 | 9 | This invention |
| 11-3 | D-1-16a | 7.3 | 7 | 8 | This invention |
| 11-4 | D-1-17a | 7.5 | 7 | 9 | This invention |
| 11-5 | D-1-22a | 7.0 | 8 | 9 | This invention |
| 11-6 | D-1-23a | 7.0 | 8 | 9 | This invention |
| 11-7 | D-8-1a | 6.5 | 12 | 11 | This invention |
| 11-8 | Sensitizing dye A | 6.0 | 52 | 32 | Comparative example |
| 11-9 | Sensitizing dye B | 5.6 | 21 | 29 | Comparative example |
| 11-10 | Sensitizing dye C | 6.0 | 18 | 23 | Comparative example |

As shown in Table 11, any of the dye-sensitized solar cells of the present invention showed initial conversion efficiency values as high as 6.5% or more. After storage in the dark place and continuous light irradiation, any of the cells had a reduction ratio of 12% or less, and thus the durability was found to be improved, as compared with the comparative examples.

Experiment 12

A dye-sensitized solar cell was produced according to the method described below, and the cell was evaluated. The results are shown in Table 12.

(1) Production of Transparent Electrically Conductive Support

As a support for photosensitive electrode, a flexible transparent electrically conductive support obtained by uniformly applying a conductive thin film of tin oxide to a thickness of 200 nm, on one surface of a sheet having a thickness of 0.4 mm and having the surfaces coated with fluorine, was used.

(2) Production of Conductive Sheet for Counter Electrode

A platinum film having a thickness of 300 nm was uniformly coated by a vacuum sputtering method, on one surface of a Kapton (registered trademark) film made of polyimide and having a thickness of 0.4 mm. The surface resistance was 5 $\Omega/cm^2$.

(3) Preparation of Semiconductor Fine Particle Dispersion Liquids

A dispersion liquid of anatase type titanium dioxide containing titanium dioxide at a concentration of 11% by mass was synthesized according to the production method described in C. J. Barbe et al., J. Am. Ceramic Soc., Vol. 80, p. 3157, using titanium tetraisopropoxide as a titanium raw material and setting the temperature of the polymerization reaction in an autoclave at 230° C. The size of the primary particles of the obtained titanium dioxide particles was 10 to 30 nm. The obtained dispersion liquid was subjected to an ultracentrifuge to separate the particles, and the aggregates were dried. Subsequently, the aggregates were pulverized in an agate mortar, and thus semiconductor fine particles a were obtained as white powder. The semiconductor fine particles a were added to 100 mL of a mixed solvent formed from water and acetonitrile at a volume ratio of 4:1, at a concentration of 32 g per 100 mL of the solvent, and the mixture was uniformly dispersed and mixed using a mixing conditioner of rotation/revolution combination type. As a result, the obtained white semiconductor fine particle dispersion liquids became highly viscous pastes having viscosities of 50 to 150N·s/$m^2$, and it was found that the paste had liquid properties adequate to be used directly in the coating. In the sample No. 12-6, the powder of polyethylene glycol (PEG) having an average molecular weight of 500,000 was compounded in an amount of 7.7 g per 100 mL of solvent. In the other semiconductor fine particle dispersion liquids, no solids excluding semiconductor fine particles were added.

(4) Measurement of Solids in Semiconductor Fine Particle Dispersion Liquid

Each of the dispersion liquids was applied to a thickness of 40 to 70 μm, on an alkali-free glass substrate having a thickness of 1.9 mm, using an applicator, and the dispersion liquid coating was dried for one hour at room temperature. Subsequently, the assembly was heated in air at 350° C. for 0.5 hours, and the weight change before and after the heating was measured. The content of solids excluding the semiconductor fine particles of the semiconductor fine particle dispersion used in the sample No. 12-6 was 1.0%. The contents of solids excluding the semiconductor fine particles in the other samples were all 0.3%.

(5) Preparation of Semiconductor Fine Particle Layer

The dispersion liquid prepared in the above item (3) was applied on the transparent electrically conductive support prepared in the above item (1), using an applicator, and the dispersion liquid coating was dried one hour at room temperature. Thereby, a uniform coating layer having a thickness of 40 to 70 μm was formed. This resultant coating layer was further treated under the conditions described in Table 12 to produce a porous semiconductor fine particle layer for dye sensitization. The final average thickness of the porous semiconductor fine particle layer was 6 to 7 μm in all cases.

(6) Preparation of Solution for Dye Adsorption

The dyes described in the Table 12 given below each were dissolved in a mixed solvent of dry acetonitrile:t-butanol: ethanol at a volume ratio of 2:1:1, to obtain a dye concentration of $3\times10^{-4}$ moles/L. In this dye solution, an organic sulfonic acid derivative having a structure of p-$C_9H_{19}$—$C_6H_4$—O—$(CH_2CH_2$—$O)_3$—$(CH_2)_4$—$SO_3Na$ was dissolved as an additive to obtain a concentration of 0.025 mol/L, and thus a solution for dye adsorption was prepared.

(7) Adsorption of Dye

The substrate coated with a porous semiconductor fine particle layer was immersed in the dye solution for adsorption described above, and was left immersed under stirring for 3 hours at 40° C.

Thus, the dye-sensitized electrodes (photosensitive electrodes) to be used for the photosensitive layer were prepared by allowing the dyes to adsorb on the semiconductor fine particle layer.

(8) Production of Dye-Sensitized Solar Cell

A dye-adsorbed porous semiconductor fine particle layer was subjected to finishing, and thereby a circular photosensitive electrode having a light-receiving area of 1.0 $cm^2$ (diameter about 1.1 cm) was formed. A platinum-deposited glass substrate as a counter electrode was superposed against the photosensitive electrode, with a frame type spacer (thickness 20 μm) produced from a thermally pressed polyethylene film inserted between the electrodes. The spacer areas were heated to 120° C., and the two substrates were pressed. Furthermore, the edge areas of the cell were sealed with an epoxy resin adhesive. Through a small hole for electrolyte liquid injection preliminarily provided at a corner area of the substrate of the counter electrode, a room temperature molten salt formed of any one of compositions of imidazolium ions E1 to E4/iodine=50:1 (mass ratio) described later as an electrolyte solution was infiltrated into a space between the electrodes by utilizing the capillary phenomenon.

E1: 1,2-dimethyl-3-propylimidazolium iodide
E2: 1-butyl-3-methylimidazolium iodide
E3: 1-methyl-3-propylimidazolium iodide
E4: 1,3-di(2-(2-(2-methoxyethoxy)ethoxy)ethyl)imidazolium iodide The process of cell construction and the process of electrolyte liquid injection described above were all carried out in dry air having a dew point of −60° C. as described above. After the injection of the molten salt, the cell was suctioned in a vacuum for several hours, and degassing of the inside of the cell containing the photosensitive electrode and the molten salt was performed. Finally, the small hole was sealed with low melting point glass. Thereby, a dye-sensitized solar cell in which an electrically conductive support, a porous semiconductor fine particle electrode adsorbed with a dye (photosensitive electrode), a electrolyte liquid, a counter electrode, and a support were laminated in this sequence, was produced.

(9) Evaluation of Dye-Sensitized Solar Cell

A xenon lamp of 500 W power (manufactured by Ushio, Inc.) was mounted with a correction filter for sunlight simulation (trade name: AM1.5 direct, manufactured by LOT-Oriel AG), and the dye-sensitized solar cell was irradiated with a pseudo-sunlight having an incident light intensity of 100 mW/cm², from the side of the porous semiconductor fine particle electrode (photosensitive electrode). The dye-sensitized solar cell was fixed closely on the stage of a thermostat, and the temperature during irradiation was controlled to 50° C. The photocurrent-voltage characteristics were measured by scanning the DC voltage applied to the device using a current voltage analyzer (Source Measure Unit Model 238, manufactured by Keithley Instruments, Inc.) at a constant rate of 10 mV/sec, and thereby measuring the photocurrent output by the cell. The energy conversion efficiencies (ii) determined thereby are described in Table 12, together with the contents of the constituent elements of the cells (semiconductor fine particles and sensitizing dyes). Furthermore, a rate of decrease in conversion efficiency after light irradiation for 24 consecutive hours was also measured. The results of these measurements are shown in the following Table 12.

When the porous semiconductor fine particle layer was prepared by applying a dispersion liquid having 1.0% by mass of the content of solids to the support made of the electrically conductive polymer and heating the layer, and the dye of the present invention was adsorbed thereon, as compared with the case where the comparative dye was adsorbed, the dye-sensitized solar cell having a high conversion efficiency was found to be obtained (comparison of sample No. 12-6 with sample Nos. 12-16 to 12-19). In the case of the dye-sensitized solar cell using the comparative dye, a reduction ratio in conversion efficiency after continuous light irradiation became as high as 40% or more. Whereas, in the case of the dye-sensitized solar cell using the dye of the present invention, a reduction ratio in conversion efficiency after continuous light irradiation was as low as 10% or less, and thus the cell was found to be excellent in durability.

TABLE 12

| | Condition for producing cell | | | | | Cell performance | | |
|---|---|---|---|---|---|---|---|---|
| Sample No. | Electrically conductive support | Metal complex dye | Electrolyte solution | Solid content (%) *1 | Heat treatment after coating/UV treatment | Conversion efficiency (%) | Decrease rate (%) *2 | Remarks |
| 12-1 | PEN | D-1-1a | E3 | 0.3 | 120° C./UV treatment | 5.4 | 5 | This invention |
| 12-2 | PEN | D-1-21a | E3 | 0.3 | 120° C./UV treatment | 5.3 | 4 | This invention |
| 12-3 | PEN | D-1-1b | E3 | 0.3 | 120° C./UV treatment | 5.4 | 5 | This invention |
| 12-4 | PC | D-1-1a | E3 | 0.3 | 120° C./UV treatment | 5.2 | 4 | This invention |
| 12-5 | PEN | D-1-17a | E3 | 0.3 | 120° C./UV treatment | 5.1 | 4 | This invention |
| 12-6 | PEN | D-1-1a | E3 | 1 | 120° C./UV treatment | 4.4 | 9 | This invention |
| 12-7 | PC | D-1-1a | E3 | 0.3 | 90° C./UV treatment | 4.6 | 6 | This invention |
| 12-8 | PEN | D-1-1a | E3 | 0.3 | 90° C./UV treatment | 4.6 | 8 | This invention |
| 12-9 | PEN | D-1-1b | E3 | 0.3 | 90° C./UV treatment | 4.5 | 7 | This invention |
| 12-10 | PEN | D-1-1a | E3 | 0.3 | 150° C./UV treatment | 5.4 | 5 | This invention |
| 12-11 | PEN | D-1-21a | E3 | 0.3 | 150° C./UV treatment | 5.2 | 4 | This invention |
| 12-12 | PEN | D-1-16a | E3 | 0.3 | 150° C./UV treatment | 5.1 | 4 | This invention |
| 12-13 | PEN | D-1-1a | E3 | 0.3 | 200° C./UV treatment | 4.7 | 5 | This invention |
| 12-14 | PEN | D-1-21a | E3 | 0.3 | 200° C./UV treatment | 4.5 | 4 | This invention |
| 12-15 | PEN | D-1-1b | E3 | 0.3 | 200° C./UV treatment | 4.5 | 5 | This invention |
| 12-16 | PEN | Sensitizing dye A | E3 | 0.3 | 120° C./UV treatment | 4.1 | 48 | Comparative example |
| 12-17 | PC | Sensitizing dye A | E3 | 0.3 | 90° C./UV treatment | 3.5 | 56 | Comparative example |
| 12-18 | PEN | Sensitizing dye A | E3 | 0.3 | 150° C./UV treatment | 4.1 | 48 | Comparative example |
| 12-19 | PEN | Sensitizing dye A | E3 | 0.3 | 200° C./UV treatment | 3.4 | 50 | Comparative example |
| 12-20 | PEN | D-1-1a | E2 | 0.3 | 120° C./UV treatment | 5.4 | 5 | This invention |
| 12-21 | PEN | D-1-1a | E1 | 0.3 | 120° C./UV treatment | 5.5 | 4 | This invention |
| 12-22 | PEN | D-1-1a | E4 | 0.3 | 120° C./UV treatment | 5.3 | 5 | This invention |
| 12-23 | PEN | D-1-1b | E4 | 0.3 | 120° C./UV treatment | 5.6 | 5 | This invention |

*1 Content of solids excluding semiconductor fine particles in dispersion liquid (%)
*2 Rate of decrease in conversion efficiency after consecutive light irradiation (%)

As shown in Table 12, when the porous semiconductor fine particle layer adsorbing the dye of the present invention was formed on the electrically conductive support made of the electrically conductive polymer, the dye-sensitized solar cell having the photoelectric conversion efficiency of a practical use level was obtained (sample Nos. 12-1 to 12-15, and 12-20 to 12-23). In particular, when the porous semiconductor fine particle layer was prepared by applying a dispersion liquid having 0.3% of the content of solids other than the semiconductor fine particles to the support, performing heat treatment at 120° C. to 150° C., irradiating the layer with ultraviolet light, and then allowing the dye of the present invention to adsorb thereon, the photoelectric conversion efficiency became as high as 5% or more (sample Nos. 12-1 to 12-5, 12-10 to 12-12, and 12-20 to 12-23).

Experiment 13

A dye-sensitized solar cell was produced in a similar manner except that a sealant paste was used in which glass spheres having a diameter of 25 μm were substantially uniformly dispersed in a resin composition composed of Epicoat 828 (trade name, manufactured by Japan Epoxy Resins, Co., Ltd.) as an epoxy-based sealant, a curing agent, and a plastic paste in <Experiment 11>, and the photoelectric conversion efficiency was measured.

The conversion efficiency (η), the reduction ratio in conversion efficiency after storage at 85° C. for 1,000 hours in a dark place, and the reduction ratio in conversion efficiency after light irradiation for 500 consecutive hours of each dye-sensitized solar cell determined in this way are shown in the following Table 13.

TABLE 13

| Sample No. | Metal complex dye | Conversion efficiency (%) | Reduction ratio of conversion efficiency after storage in dark place (%) | Reduction ratio of conversion efficiency after continuous irradiation (%) | Remarks |
|---|---|---|---|---|---|
| 13-1 | D-1-1a | 7.4 | 5 | 5 | This invention |
| 13-2 | D-1-1b | 7.3 | 5 | 6 | This invention |
| 13-3 | D-1-21a | 7.4 | 6 | 7 | This invention |
| 13-4 | D-1-24b | 7.2 | 6 | 7 | This invention |
| 13-5 | D-1-16a | 7.6 | 7 | 8 | This invention |
| 13-6 | D-1-17a | 7.5 | 7 | 8 | This invention |
| 13-7 | D-1-22a | 7.1 | 8 | 9 | This invention |
| 13-8 | D-9-1a | 7.4 | 9 | 10 | This invention |
| 13-9 | D-1-8b | 7.0 | 6 | 8 | This invention |
| 13-10 | D-7-1 | 6.5 | 5 | 7 | This invention |
| 13-11 | D-1-23a | 6.7 | 7 | 11 | This invention |
| 13-12 | D-8-1a | 6.4 | 9 | 12 | This invention |
| 13-13 | Sensitizing dye A | 6.0 | 52 | 32 | Comparative example |
| 13-14 | Sensitizing dye B | 5.6 | 21 | 29 | Comparative example |
| 13-15 | Sensitizing dye C | 6.0 | 18 | 23 | Comparative example |
| 13-16 | Sensitizing dye D | 6.1 | 17 | 22 | Comparative example |
| 13-17 | Sensitizing dye E | 6.1 | 18 | 23 | Comparative example |

As shown in Table 13, any of the dye-sensitized solar cells of the present invention showed an initial conversion efficiency value as high as 7.0% or more. After storage in the dark place and continuous light irradiation, any of the cells had a reduction ratio equal to or less than 9%, and thus the durability was found to be superior, as compared with the cells in the comparative examples.

Experiment 14

A TiO$_2$ suspension prepared according to a sol-gel method was used. A porous layer of TiO$_2$ was applied to a FTO glass plate by screen printing, and calcined at 450° C. A dye was adsorbed on this TiO$_2$ porous layer by immersing this FTO glass substrate with the TiO$_2$ porous layer into a 10$^{-4}$ mol/L ethanol solution of a metal complex dye of the present invention, or a comparative sensitizing dye.

Independently, 100 mg of 2,2',7,7'-tetrakis(diphenylamino)-9,9'-spirobifluorene was dissolved in 5 mL of chloroform. The solution obtained was lightly applied to a surface of the above-described FTO glass substrate with the TiO$_2$ porous layer, and thus this solution was infiltrated into pores of the layer. Next, one drop of the solution was directly placed on the surface of the above-described FTO glass substrate with the TiO$_2$ porous layer, and the substrate was dried at room temperature. Subsequently, the above-described FTO glass substrate with the TiO$_2$ porous layer was mounted in a deposition apparatus, and a 100 nm-thick layer of 2,2',7,7'-tetrakis(diphenylamino)-9,9'-spirobifluorene was further arranged by thermal deposition under about 10$^{-5}$ mb vacuum. A 200 nm-thick gold layer was further coated on this above-described FTO glass substrate with the TiO$_2$ porous layer (coating support) in the deposition apparatus to serve as a counter electrode.

The thus prepared sample was attached to an optical device containing a high pressure lamp, an optical filter, a lens, and a mounting. The intensity could be changed by use of the filter, and moving the lens. Contact points were attached to a gold layer and a SnO$_2$ layer, respectively, and the sample was attached to a current measurement apparatus while irradiating the sample with light. For measurement, light having a wavelength less than 430 nm was shielded using a suitable optical filter. The apparatus was further adjusted such that the radiation intensity substantially corresponded to about 1,000 W/m$^2$.

The contact points were attached to the gold layer and the SnO$_2$ layer, respectively, and both contact points were connected to a potentiostat while irradiating the sample with light. Without applying external voltage, a current of about 90 nA was generated in a sample using the comparative sensitizing dye (Comparative Example: sensitizing dye A), but a current of about 190 nA was generated in the sample using the metal complex dye of the present invention (Example: D-1-1b). The current disappeared without irradiation in any of the samples.

Experiment 15

Also in a tandem cell prepared in a manner similar to Example 1 in JP-A-2000-90989, a higher conversion efficiency was confirmed in the metal complex dye of the present invention, as compared with the sample using the comparative dye.

Experiment 16

A dye-sensitized type solar cell shown in FIG. 1 of JP-A-2003-217688 was produced according to the procedure shown below.

First, 125 mL of titanium isopropoxide was added dropwise to 750 mL of 0.1 M nitric acid aqueous solution (manufactured by Kishida Chemical Co., Ltd.), and the resultant mixture was heated at 80° C. for 8 hours to allow a hydrolysis reaction, and a sol solution was prepared. The sol solution obtained was then subjected to particle growth at 250° C. for 15 hours in an autoclave made of titanium. The sol solution was further subjected to ultrasonic dispersion for 30 minutes, and thus a colloidal solution containing titanium oxide particles having an average primary particle size of 20 nm was prepared.

The colloidal solution obtained that contains titanium oxide particles was slowly concentrated to a titanium oxide solution of 10 mass % by means of an evaporator, and then polyethylene glycol (manufactured by Kishida Chemical Co., Ltd., mass average molecular weight: 200,000) was added at a mass ratio of 40% to titanium oxide, and thus a dispersion liquid in which titanium oxide particles were dispersed was obtained.

The prepared titanium oxide suspension liquid was applied by a doctor blade method to a side of a transparent electrically conductive film 2 of a glass substrate 1 in which a $SnO_2$ film was formed as the transparent electrically conductive film 2, and thus a coating film having an area of about 10 mm×10 mm was obtained. This coating film was preliminarily dried at 120° C. for 30 minutes, further calcined at 500° C. for 30 minutes under an oxygen environment, and thus a titanium oxide film having a film thickness of about 10 μm was formed to constitute a first layer porous semiconductor layer of a first layer porous photoelectric conversion layer 4.

Next, 4.0 g of commercially available titanium oxide fine particles (manufactured by TAYCA Corporation, product name: TITANIX JA-1, particle size about 180 nm) and 0.4 g of magnesium oxide powder (manufactured by Kishida Chemical Co., Ltd.) were put in 20 mL of distilled water, and the resultant dispersion liquid was adjusted to pH=1 with hydrochloric acid. Zirconia beads were further added, this mixed liquid was subjected to dispersion treatment for 8 hours by means of a paint shaker, and then the beads were removed. Then, polyethylene glycol (manufactured by Kishida Chemical Co., Ltd., mass average molecular weight: 200,000) was added at a mass ratio of 40% to titanium oxide, the resultant mixture was stirred, and thus a dispersion liquid in which titanium oxide particles were dispersed was obtained.

The prepared titanium oxide suspension liquid was applied by the doctor blade method to the first layer porous semiconductor layer of the glass substrate 1 on which the titanium oxide film of the first layer porous semiconductor layer was formed, and thus a coating film was obtained. This coating film was preliminarily dried at 80° C. for 20 minutes, further calcined at about 500° C. for 60 minutes under an oxygen environment, and thus a titanium oxide film 1 having a film thickness of about 22 μm was formed to constitute a second layer porous semiconductor layer of a second layer porous photoelectric conversion layer 5. When a haze ratio of the porous semiconductor layer was measured, the haze ratio was 84%.

As a dye (first dye) having a maximum sensitivity absorption wavelength region in an absorption spectrum in a short wavelength side, the following merocyanine dye S-2 was dissolved in ethanol, and thus a dye solution for adsorption having a concentration of $3\times10^{-4}$ mol/L for the first dye was prepared.

The maximum absorption wavelength of the merocyanine dye S-2 on the longest wavelength side in THF/water (=6:4, trifluoroacetic acid 0.1 v/v %) solution was 412 nm.

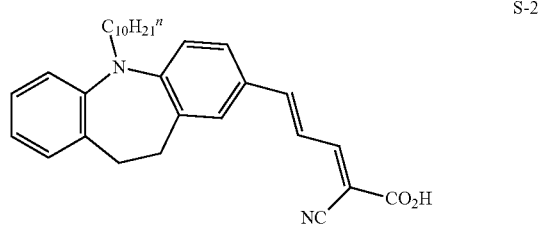

The glass substrate 1 provided with the transparent electrically conductive film 2 and the porous semiconductor layer 3 was immersed into a dye solution for adsorption for the first dye warmed to about 50° C. for 10 minutes to allow the first dye to adsorb on the porous semiconductor layer 3. Then, the glass substrate 1 was washed with absolute ethanol several times, and dried at about 60° C. for about 20 minutes. Subsequently, the glass substrate 1 was immersed into 0.5 N-hydrochloric acid for about 10 minutes, and then washed with ethanol to desorb the first dye adsorbed on the second layer porous semiconductor layer. The glass substrate 1 was further dried at 60° C. for about 20 minutes.

Next, as a dye (second dye) having a maximum sensitivity absorption wavelength region in an absorption spectrum on a long wavelength side, a dye solution for adsorption having a concentration of $3\times10^{-4}$ mol/L for a second dye was prepared by dissolving a comparative dye or a metal complex dye of the present invention in ethanol.

Herein, the maximum absorption wavelength of the dye used on the longest wavelength side in THF/water (=6:4, trifluoroacetic acid 0.1 v/v %) solution was 568 nm for the metal complex dye D-1-1a of the present invention, and 552 nm for the comparative dye A.

The glass substrate 1 including the transparent electrically conductive film 2 and the porous semiconductor layer 3 was immersed into a dye solution for adsorption for the second dye at room temperature and under normal pressure for 15 minutes to allow the second dye to adsorb on the porous semiconductor layer 3. Then, the glass substrate 1 was washed with absolute ethanol several times, and dried at about 60° C. for about 20 minutes. When a haze ratio of the porous semiconductor layer was measured, the haze ratio was 84% (when the comparative dye was used), and 85% (when the metal complex dye of the present invention was used).

Next, a redox electrolyte was prepared by dissolving, in 3-methoxypropionitrile solvent, dimethylpropyl imidazolium iodide to have a concentration of 0.5 mol/L, lithium iodide to have a concentration of 0.1 mol/L, and iodine to have a concentration of 0.05 mol/L. A side of the porous semiconductor layer 3 of the glass substrate 1 provided with the porous semiconductor layer 3 on which the first dye and the second dye were adsorbed, and a side of platinum of the support 20 in the counter electrode side composed of an ITO glass plate having platinum as a counter electrode layer 8 were installed to be opposed, the prepared redox electrolyte was injected into a space between the two sides, and a circumference was sealed with a sealing agent 9 of an epoxy-based resin, and thus a dye-sensitized type solar cell was completed.

A titanium oxide film 2 was prepared in a manner similar to the titanium oxide film 1 except that the second layer porous semiconductor layer was formed as a layer identical with the first porous semiconductor layer, more specifically, the second layer porous semiconductor layer was formed using the titanium oxide suspension liquid for forming the first porous semiconductor layer, and a solar cell was produced using the same in a similar manner, and evaluated. A haze ratio of the porous photoelectric conversion layer was 15% (when the comparative dye was used), and 16% (when the metal complex dye of the present invention was used).

The results of evaluating the solar cells obtained, according to measuring conditions: AM-1.5 (100 mW/cm$^2$) were shown in Table 14. The results were evaluated such that one having a conversion efficiency of 3.5% or more was rated as "⊙"; one having a conversion efficiency of equal to or more than 2.5% and less than 3.5% was rated as "○"; one having a conversion efficiency of equal to or more than 2.0% and less than 2.5% was rated as "Δ"; and one having a conversion efficiency of less than 2.0% was rated as "x".

TABLE 14

| Sample No. | Titanium oxide film | Dye | Conversion efficiency | Remarks |
|---|---|---|---|---|
| 14-1 | 1 | D-1-1a | ⊙ | This invention |
| 14-2 | 2 | D-1-1a | ⊙ | This invention |
| 14-3 | 1 | Sensitizing dye A | Δ | Comparative example |
| 14-4 | 2 | Sensitizing dye A | X | Comparative example |

The metal complex dyes of the present invention are excellent in the photoelectric conversion efficiency, and found to be effective also in this system.

Experiment 17

Were dispersed 4.0 g of commercially available titanium oxide particles (manufactured by TAYCA Corporation, average particle size 20 nm) and 20 mL of diethylene glycol monomethyl ether using hard glass beads by means of a paint shaker for 6 hours, and then the beads were removed, and a titanium oxide suspension liquid was prepared. Subsequently, this titanium oxide suspension liquid was applied using a doctor blade to a glass plate (electrode layer) on which a tin oxide electrically conductive layer was attached beforehand, the glass plate was preliminarily dried at 100° C. for 30 minutes, and then calcined at 500° C. for 40 minutes in an electric furnace, and thus a titanium oxide film (semiconductor material) was formed on the glass plate. Apart from the above, a photosensitizing dye solution was obtained by dissolving the sensitizing dye of the present invention or a comparative dye in ethanol.

The concentration of this photosensitizing dye solution was $5 \times 10^{-4}$ mol/L. Next, the above-described glass plate on which film-shaped titanium oxide was formed was put in this solution to allow dye adsorption at 60° C. for 60 minutes, and then dried. Thus, a photoelectric conversion layer composed of the semiconductor material and the photosensitizing dye was formed on the glass plate (as a sample A). On the photoelectric conversion layer of the above-described sample A, a toluene solution (1%) of polyvinylcarbazole (mass average molecular weight 3,000) as a hole transport material was applied, and subjected to drying under reduced pressure, and thus a hole transport layer was formed (as a sample B). In 100 mL of acetone, 1.95 g of ethylcarbazole as an intermolecular charge transfer complex, and 2.03 g of 5-nitronaphthoquinone were dissolved, and the solution obtained was repeatedly applied onto the hole-transporting layer of the sample B, and thus a conduction layer was formed. Subsequently, a gold electrode (counter electrode) was deposited on the conduction layer, and thus a photoelectric conversion element was obtained (as a sample C). The photoelectric conversion element (sample C) obtained was irradiated with light having an intensity of 100 W/m² by means of a solar simulator. The results are shown in Table 15. The results were evaluated such that one having a conversion efficiency of 1.5% or more was rated as "⊙"; one having a conversion efficiency of equal to or more than 1.0% and less than 1.5% was rated as "○"; one having a conversion efficiency of equal to or more than 0.5% and less than 1.0% was rated as "Δ"; and one having a conversion efficiency of less than 0.5% was rated as "x".

TABLE 15

| Sample No. | Dye | Conversion efficiency | Remarks |
|---|---|---|---|
| 15-1 | D-1-1b | ⊙ | This invention |
| 15-2 | D-1-17a | ○ | This invention |
| 15-3 | D-1-17b | ○ | This invention |
| 15-4 | Sensitizing dye A | X | Comparative example |
| 15-5 | Sensitizing dye B | X | Comparative example |
| 15-6 | Sensitizing dye C | Δ | Comparative example |

The metal complex dyes of the present invention are excellent in the photoelectric conversion efficiency, and found to be effective also in this system.

Example 18

(1) Formation of a First Photoelectric Conversion Layer

Were dispersed 4.0 g of commercially available titanium oxide particles (manufactured by TAYCA Corporation, average particle size 30 nm) and 20 mL of diethylene glycol monomethyl ether using hard glass beads by means of a paint shaker for 6 hours, and then the beads were removed, and thus a titanium oxide suspension liquid was prepared. Subsequently, the titanium oxide suspension liquid was applied using a doctor blade to a glass plate on which a tin oxide electrically conductive layer was attached beforehand, the glass plate was preliminarily dried at 100° C. for 30 minutes, and then calcined at 500° C. for 40 minutes in an electric furnace, and thus a glass plate with a titanium oxide film was obtained.

Apart from the above, a dye [cis-dithiocyanine-N-bis(2,2'-bipyridyl-4,4'-dicarboxylic acid) ruthenium] represented by the following S-3 was dissolved in ethanol.

In addition, the maximum absorption wavelength of S-3 on the longest wavelength side in THF/water (=6:4, trifluoroacetic acid 0.1 v/v %) solution was 552 nm.

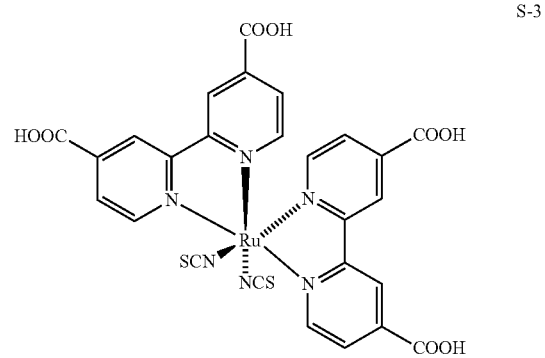

S-3

The concentration of this dye was $3 \times 10^{-4}$ mol/L. Next, the above-described glass plate on which the film-shaped titanium oxide was formed was put in this solution to allow dye adsorption at 60° C. for 720 minutes, and then dried, and thus a first photoelectric conversion layer (sample A) of the present invention was obtained.

(2) Formation of a Second Photoelectric Conversion Layer

Were dispersed 4.0 g of commercially available nickel oxide particles (manufactured by Kishida Chemical Co., Ltd, average particle size 100 nm) and 20 mL of diethylene glycol monomethyl ether using glass beads by means of a paint shaker for 8 hours, and then the beads were removed, and thus a nickel oxide suspension liquid was prepared. Subsequently, this nickel oxide suspension liquid was applied using a doctor blade to a glass plate on which a tin oxide electrically conductive layer was attached, the glass plate was preliminarily dried at 100° C. for 30 minutes, and then calcined at 300° C. for 30 minutes, and thus a glass plate with a nickel oxide film was obtained.

Apart from the above, a metal complex dye of the present invention or a comparative dye was dissolved in dimethyl sulfoxide.

Herein, the maximum absorption wavelength of the dyes used on the longest wavelength side in THF/water (=6:4, trifluoroacetic acid 0.1 v/v %) solution was 568 nm for the metal complex dye D-1-1a of the present invention, 568 nm for the metal complex dye D-1-1b of the present invention, and 552 nm for the comparative dye A.

The concentration of the dye was $1 \times 10^{-4}$ mol/L. Next, the glass plate on which the film-shaped nickel oxide was formed was put in the solution to allow dye adsorption at 70° C. for 60 minutes, and then dried, and thus a second photoelectric conversion layer (sample B) of the present invention was obtained.

(3) the Sample B was Placed on the Above-Described Sample A

A Liquid electrolyte was put in a space between the two electrodes, a lateral side thereof was sealed with a resin, and then a lead wire was attached thereto, and thus a photoelectric conversion element (device constitution C) of the present invention was produced. Herein, the liquid electrolyte was used in which tetrapropylammonium iodide and iodine were dissolved in a mixed solvent of acetonitrile/ethylene carbonate (1:4 in a volume ratio) to be 0.46 mol/L and 0.06 mol/L in the concentration, respectively.

A transparent electrically conductive glass plate was used in which the above-described sample A was provided as one electrode, and platinum was carried thereon as a counter electrode. A liquid electrolyte was put in a space between the two electrodes, a lateral side thereof was sealed with a resin, and then a lead wire was attached thereto, and thus a comparative photoelectric conversion element (device constitution D) of the present invention was produced.

The photoelectric conversion elements (the sample C and the sample D) obtained were irradiated with light having an intensity of 100 W/m² by means of a solar simulator. The results were evaluated such that one having a conversion efficiency of 6.5% or more was rated as "⊙"; one having a conversion efficiency of equal to or more than 6.0% and less than 6.5% was rated as "○"; one having a conversion efficiency of equal to or more than 5.0% and less than 6.0% was rated as "Δ"; and one having a conversion efficiency of less than 5.0% was rated as "x".

TABLE 16

| Sample No. | Device constitution | First dye | Second dye | Conversion efficiency | Remarks |
|---|---|---|---|---|---|
| 16-1 | C | S-3 | D-1-1a | ⊙ | This invention |
| 16-2 | C | S-3 | D-1-1b | ⊙ | This invention |
| 16-3 | C | S-3 | Sensitizing dye A | Δ | Comparative example |

TABLE 16-continued

| Sample No. | Device constitution | First dye | Second dye | Conversion efficiency | Remarks |
|---|---|---|---|---|---|
| 16-4 | D | S-3 | — | X | Comparative example |

The dyes of the present invention are excellent in the photoelectric conversion efficiency, and found to be effective also in this system.

Experiment 19

An example is described in which a dye-sensitized type solar cell produced by using the polymer electrolyte described in JP-A-2001-210390 was produced.

As a coating liquid for preparing a titanium oxide film, 4.0 g of commercially available titanium oxide particles (manufactured by TAYCA Corporation, trade name AMT-600, an anatase type crystal, an average particle size 30 nm, and a specific surface area 50 m²/g) and 20 mL of diethylene glycol monomethyl ether were dispersed using glass beads by means of a paint shaker for 7 hours, and then the beads were removed, and thus a titanium oxide suspension liquid was prepared. This titanium oxide suspension liquid was applied using a doctor blade on a side of a transparent electrically conductive film on a substrate on which $SnO_2$ was prepared on a glass substrate 1 as the transparent electrically conductive film at a film thickness of about 11 μm and an area of about 10 mm×10 mm, the glass plate was preliminarily dried at 100° C. for 30 minutes, and calcined at 460° C. for 40 minutes under oxygen. As a result, a titanium oxide film A having a film thickness of about 8 μm was prepared.

Next, a metal complex dye of the present invention or a comparative dye was dissolved in absolute ethanol at a concentration of $3 \times 10^{-4}$ mol/L, and thus a dye solution for adsorption was prepared. This dye solution for adsorption and the transparent substrate provided with the titanium oxide film and the transparent electrically conductive film obtained as described above were put in a container, respectively, to allow the dye to adsorb by allowing the dye to permeate thereinto at 40° C. for about 4 hours. Then, the substrate was washed with absolute ethanol several times, and dried at 60° C. for about 20 minutes.

Next, among methacrylate-based monomer units of the polymer compound represented by Formula (P), a monomer unit was used as constituted of a butanetetrayl group, as R, having a methyl group, and as A, a core containing 8 polyethylene oxide groups and two polypropylene oxide groups.

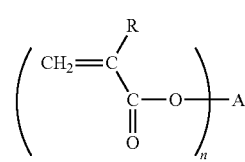

Formula (P)

In Formula (P), R represents a methyl group, A represents a residue bonded with the ester group through a carbon atom, and n represents 2 to 4.

This monomer unit was dissolved in propylene carbonate (hereinafter, described as PC) at a concentration of 20% by mass, and azobisisobutyronitril (AIBN) as a polymerization initiator for thermal polymerization was dissolved at a concentration of 1% by mass based on the monomer unit, and thus a monomer solution was prepared. A procedure for impregnating this monomer solution into the titanium oxide film is shown below.

A container such as a beaker was installed in a vacuum vessel, the above-described titanium oxide film A on the transparent substrate containing the transparent electrically conductive film and having the dye absorbed thereon was put in the container, and the vacuum vessel was evacuated for about 10 minutes by means of a rotary pump. The monomer solution was injected into the beaker while keeping the inside of the vacuum vessel under vacuum conditions to allow the monomer solution to be impregnated thereinto for about 15 minutes, and thus the monomer solution was sufficiently infiltrated into titanium oxide. A separator made of polyethylene, a PET film and a presser plate were installed, and fixed with a jig. Then, the polymer compound was prepared by allowing thermal polymerization by heating at about 85° C. for 30 minutes.

Next, a redox electrolyte to be impregnated into the polymer compound was prepared. The redox electrolyte was prepared by using polycarbonate (PC) as a solvent, and dissolving lithium iodide to a concentration of 0.5 mol/L, and iodine to a concentration of 0.05 mol/L. The above-mentioned polymer compound prepared on the titanium oxide film A was immersed into this solution for about 2 hours to infiltrate the redox electrolyte into the polymer compound, and thus the polymer electrolyte was prepared.

Then, an electrically conductive substrate provided with a platinum film was installed, a circumference was sealed with an epoxy-based sealant, and thus a device A was prepared.

Moreover, after dye adsorption on the titanium oxide film A, a device B was prepared, not by performing the monomer impregnation treatment as mentioned above, but by directly injecting into a space to the counter electrode the oxidation reduction electrolyte prepared using polycarbonate (PC) as a solvent, and dissolving lithium iodide to a concentration of 0.5 mol/L, and iodine to a concentration of 0.05 mol/L. The device A and the device B were irradiated with light having an intensity of 1,000 W/m$^2$ by means of a solar simulator. The results are shown in Table 17. The results were evaluated such that one having a conversion efficiency of 3.5% or more was rated as "⊙"; one having a conversion efficiency of equal to or more than 2.5% and less than 3.5% was rated as "○"; one having a conversion efficiency of equal to or more than 2.0% and less than 2.5% was rated as "Δ"; and one having a conversion efficiency of less than 2.0% was rated as "x".

TABLE 17

| Sample No. | Device | Dye | Conversion efficiency | Remarks |
|---|---|---|---|---|
| 17-1 | A | D-1-1b | ⊙ | This invention |
| 17-2 | B | D-1-1b | ⊙ | This invention |
| 17-3 | A | Sensitizing dye A | X | Comparative example |
| 17-4 | B | Sensitizing dye A | Δ | Comparative example |

Table 17 shows that the samples prepared by using the metal complex dyes of the present invention are excellent in the photoelectric conversion efficiency, and the dyes are found to be effective also in this system.

Experiment 20

Production of Photoelectric Conversion Element

The photoelectric conversion element shown in FIG. 1 was produced as described below.

On a glass substrate, a film of tin oxide doped with fluorine was formed by sputtering as a transparent conductive film, and this film was scribed with a laser to partition the transparent conductive film into two parts.

Next, 32 g of anatase type titanium oxide (P-25 (trade name) manufactured by Nippon Aerosil Co., Ltd.) was added to 100 mL of a mixed solvent formed from water and acetonitrile at a volume ratio of 4:1, and the mixture was uniformly dispersed and mixed using a mixing conditioner of rotation/revolution combination type, to obtain semiconductor fine particle dispersion liquid. This dispersion liquid was applied to the transparent electrically conductive film, heating was carried out at 500° C., and thus a light-receiving electrode was prepared.

Then, a dispersion liquid containing silica particles and rutile type titanium dioxide at 40:60 (mass ratio) was prepared in a similar manner, this dispersion liquid was applied to the above-described light-receiving electrode, heating was carried out at 500° C., and thus an insulating porous body was formed. Subsequently, a carbon electrode was formed as a counter electrode.

Next, the glass substrate on which the above-described insulating porous body was formed was immersed for 5 hours into an ethanol solution of a sensitizing dye (in combination with a plurality of dyes or alone) described in the following Table 18. A glass substrate on which the sensitizing dye was dyed was immersed into a 4-tert-butylpyridine 10% ethanol solution for 30 minutes, then, washed with ethanol, and dried naturally. The thickness of the thus obtained photosensitive layer was 10 μm, and an application amount of semiconductor fine particles was 20 g/m$^2$. As the electrolyte, a methoxypropionitrile solution containing dimethylpropylimidazolium iodide (0.5 mol/L) and iodine (0.1 mol/L) was used.

Herein, the maximum absorption wavelength of the dye used on the longest wavelength side in THF/water (=6:4, trifluoroacetic acid 0.1 v/v %) solution was 581 nm for the sensitizing dye F, 581 nm for the sensitizing dye G, and 776 nm for the sensitizing dye H.

(Measurement of Photoelectric Conversion Efficiency)

Pseudo-sunlight which did not include ultraviolet radiation was generated by passing the light of a 500-W xenon lamp (manufactured by Ushio, Inc.) through an AM1.5G filter (manufactured by Oriel Instruments Corp.) and a sharp cutoff filter (Kenko L-42, trade name). The intensity of this light was 89 mW/cm$^2$. The produced photoelectric conversion element was irradiated with this light, and the electricity thus generated was measured with a current-voltage measurement device (Keithley-238 type, trade name). The results of measuring the conversion efficiencies of the photoelectrochemical cells thus determined are presented in the following Table 18. The results were evaluated such that one having a conversion efficiency of 8.5% or more was rated as "☆"; one having a conversion efficiency of equal to or more than 7.5% and less than 8.5% was rated as "⊙"; one having a conversion efficiency of equal to or more than 7.3% and less than 7.5% was rated as "○"; one having a conversion efficiency of equal to or more than 7.1% and less than 7.3% was rated as "Δ"; and one having a conversion efficiency of less than 7.1% was rated as "x".

TABLE 18

| Sample No. | Sensitizing dye 1 (Adsorption solution concentration × $10^{-4}$ mol/L) | Sensitizing dye 2 (Adsorption solution concentration × $10^{-4}$ mol/L) | Conversion efficiency | Remarks |
| --- | --- | --- | --- | --- |
| 18-1 | Sensitizing dye D (0.1) | D-1-1a (0.1) | ⊙ | This invention |
| 18-2 | Sensitizing dye E (0.1) | D-1-1a (0.1) | ⊙ | This invention |
| 18-3 | Sensitizing dye F (0.1) | D-1-1a (0.1) | ☆ | This invention |
| 18-4 | Sensitizing dye F (0.1) | D-1-1b (0.2) | ☆ | This invention |
| 18-5 | Sensitizing dye D (0.1) | D-1-21a (0.1) | ⊙ | This invention |
| 18-6 | Sensitizing dye E (0.1) | D-1-21a (0.1) | ⊙ | This invention |
| 18-7 | Sensitizing dye F (0.1) | D-1-21a (0.1) | ☆ | This invention |
| 18-8 | Sensitizing dye D (0.1) | D-1-17b (0.1) | ⊙ | This invention |
| 18-9 | Sensitizing dye E (0.1) | D-1-17b (0.1) | ⊙ | This invention |
| 18-10 | Sensitizing dye F (0.1) | D-1-17b (0.1) | ☆ | This invention |
| 18-11 | Sensitizing dye D (0.1) | D-1-16b (0.1) | ⊙ | This invention |
| 18-12 | Sensitizing dye E (0.1) | D-1-16b (0.1) | ⊙ | This invention |
| 18-13 | Sensitizing dye F (0.1) | D-1-16b (0.1) | ☆ | This invention |
| 18-14 | Sensitizing dye D (0.1) | D-1-22a (0.1) | ○ | This invention |
| 18-15 | Sensitizing dye D (0.1) | D-9-1a (0.1) | ○ | This invention |
| 18-16 | Sensitizing dye D (0.1) | D-1-8a (0.1) | ○ | This invention |
| 18-17 | Sensitizing dye D (0.1) | D-7-1 (0.1) | ○ | This invention |
| 18-18 | Sensitizing dye D (0.1) | D-1-23a (0.1) | ○ | This invention |
| 18-19 | Sensitizing dye D (0.1) | D-8-1a (0.1) | ○ | This invention |
| 18-20 | Sensitizing dye D (0.1) | None | Δ | Comparative example |
| 18-21 | Sensitizing dye E (0.1) | None | Δ | Comparative example |
| 18-22 | Sensitizing dye F (0.1) | None | X | Comparative example |
| 18-23 | None | D-8-1a (0.1) | X | Comparative example |

The structures of the sensitizing dyes F to H are shown below.

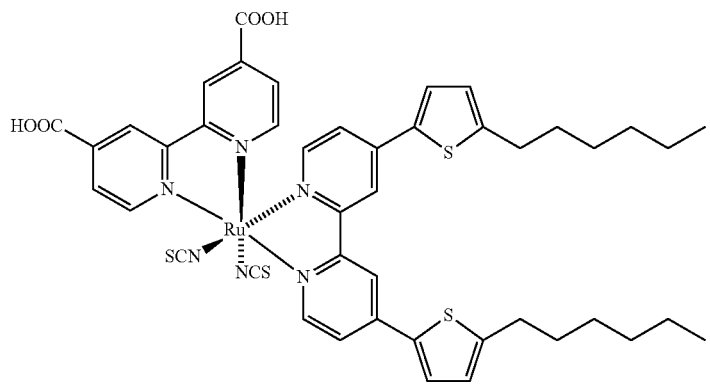

Sensitizing dye F

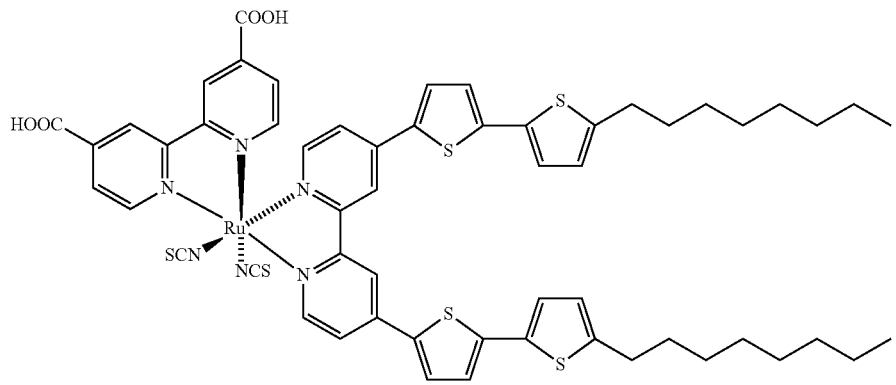

Sensitizing dye G

Sensitizing dye H

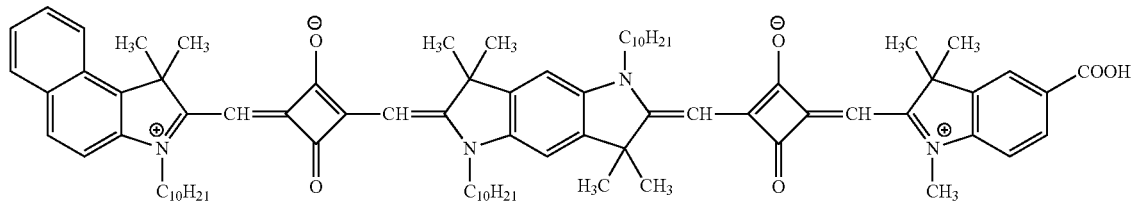

As shown in Table 18, the electrochemical cell prepared using the dye of the present invention showed a value of the conversion efficiency as high as 7.5% or more, when the metal complex dye of the present invention was used in combination with other dyes. Whereas, according to the comparative examples in which the metal complex dye of the present invention was not used, the conversion efficiency was insufficient as low as less than 7.3%, even when the dye was used in combination with other dyes.

The conversion efficiency (η), the reduction ratio in conversion efficiency after storage at 85° C. for 1,000 hours in a dark place, and the reduction ratio in conversion efficiency after light irradiation for 500 consecutive hours of each dye-sensitized solar cell are shown in the following Table 19.

TABLE 19

| Sample No. | Metal complex dye | Co-adsorbent | Conversion efficiency (%) | Reduction ratio of conversion efficiency after storage in dark place (%) | Reduction ratio of conversion efficiency after continuous irradiation (%) | Remarks |
| --- | --- | --- | --- | --- | --- | --- |
| 19-1 | D-1-1a | Chenodeoxycholic acid | 9.3 | 3 | 3 | This invention |
| 19-2 | D-1-1a | Cholic acid | 9.1 | 4 | 4 | This invention |
| 19-3 | D-1-1a | Deoxycholic acid | 9.2 | 4 | 3 | This invention |
| 19-4 | D-1-1a | Butanoic acid | 8.3 | 5 | 4 | This invention |
| 19-5 | D-1-1a | Decanoic acid | 8.6 | 3 | 5 | This invention |
| 19-6 | D-1-16a | Chenodeoxycholic acid | 9.5 | 6 | 7 | This invention |
| 19-7 | D-1-16a | Cholic acid | 9.3 | 6 | 7 | This invention |
| 19-8 | D-1-16a | Deoxycholic acid | 9.2 | 6 | 6 | This invention |
| 19-9 | D-1-16a | Butanoic acid | 8.5 | 5 | 7 | This invention |
| 19-10 | D-1-16a | Decanoic acid | 8.6 | 4 | 7 | This invention |
| 19-11 | D-1-21a | Chenodeoxycholic acid | 9.1 | 6 | 5 | This invention |
| 19-12 | D-1-17a | Chenodeoxycholic acid | 9.0 | 6 | 7 | This invention |
| 19-13 | D-1-8b | Chenodeoxycholic acid | 8.7 | 5 | 6 | This invention |
| 19-14 | D-2-8 | Chenodeoxycholic acid | 9.0 | 5 | 5 | This invention |
| 19-15 | D-1-1a | None | 7.4 | 5 | 5 | This invention |
| 19-16 | D-1-16a | None | 7.6 | 7 | 8 | This invention |
| 19-17 | D-1-21a | None | 7.4 | 6 | 7 | This invention |
| 19-18 | D-1-17a | None | 7.5 | 7 | 8 | This invention |
| 19-19 | D-1-8b | None | 7.0 | 6 | 9 | This invention |
| 19-20 | D-2-8 | None | 7.2 | 7 | 7 | This invention |
| 19-21 | Sensitizing dye A | Butanoic acid | 6.3 | 48 | 31 | Comparative example |
| 19-22 | Sensitizing dye D | Butanoic acid | 5.9 | 16 | 20 | Comparative example |
| 19-23 | Sensitizing dye E | Butanoic acid | 6.3 | 17 | 22 | Comparative example |
| 19-24 | Sensitizing dye A | None | 6.0 | 52 | 32 | Comparative example |
| 19-25 | Sensitizing dye D | None | 6.1 | 17 | 22 | Comparative example |
| 19-26 | Sensitizing dye E | None | 6.1 | 18 | 23 | Comparative example |

Experiment 21

A dye-sensitized solar cell was produced in a manner similar to <Experiment 11> except that the method for preparation of the titanium oxide fine particle layer (electrode A) on which the dye of <Experiment 11> was adsorbed was changed to a method for adjusting a liquid in which the dye was dissolved to a concentration: $1 \times 10^{-4}$ mol/L, and the above-mentioned co-adsorbent was dissolved to be in the range of $0.3 \times 10^{-4}$ mol to $30 \times 10^{-4}$ mol, both in ethanol, and adjusting a liquid in which only the dye was dissolved therein without using the co-adsorbent, and immersing each electrode thereinto for 3 hours, and the photoelectric conversion efficiency was measured.

As is clear from Table 19 described above, the samples in which the metal complex dyes of the present invention were used are excellent in the conversion efficiency and the durability, and confirmed to have an improved conversion efficiency and durability by use of the co-adsorbent, and found to be effective also in this system.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2010-127308 filed in Japan on Jun. 2, 2010, and Patent Application No. 2011-108469 filed in Japan on May 13, 2011, each of which is entirely herein incorporated by reference.

REFERENCE SIGNS LIST

1 Electrically conductive support
2 Photosensitive layer

21 Dye (Sensitizing dye)
22 Semiconductor fine particle
3 Hole transfer layer
4 Counter electrode
5 Light-receiving electrode
6 External circuit
10 Photoelectric conversion element
100 Photoelectrochemical cell

The invention claimed is:

1. A metal complex dye, which is represented by any of Formulas (XIII) to (XV):

Formula (XIII)

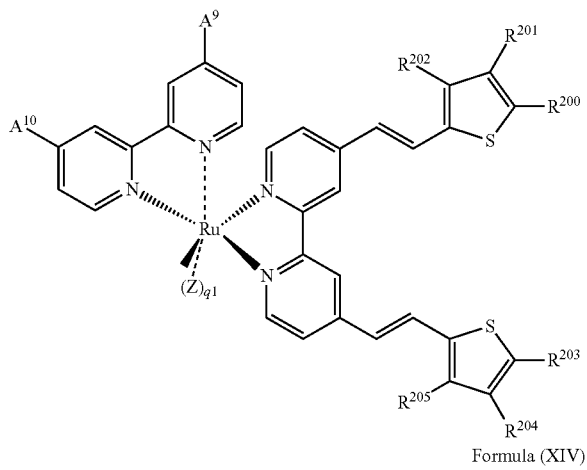

Formula (XIV)

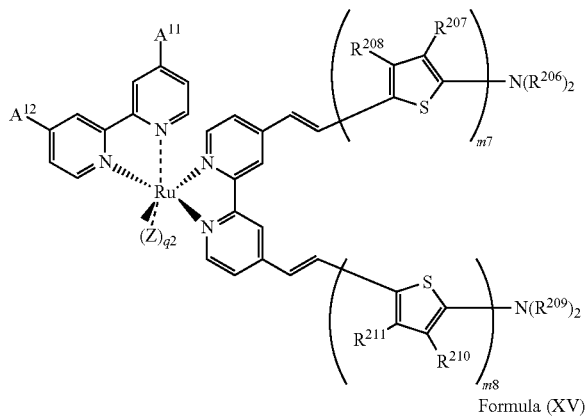

Formula (XV)

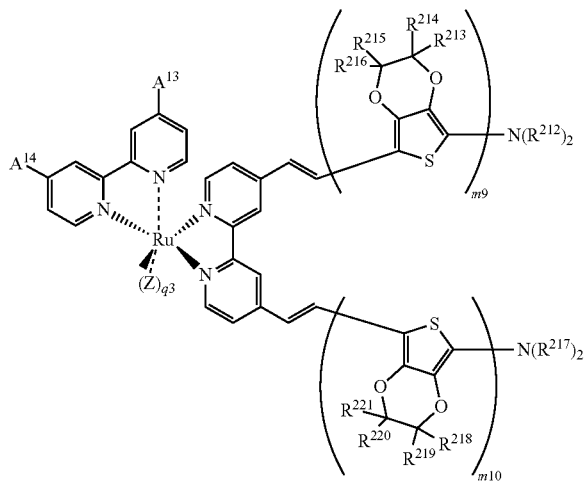

wherein
$A^9, A^{10}, A^{11}, A^{12}, A^{13}$ and $A^{14}$ each independently represent a carboxyl group or a salt thereof; $R^{200}$ and $R^{203}$ each independently represent an alkynyl group; $R^{202}$, $R^{205}$, $R^{207}$, $R^{208}$, $R^{210}$, $R^{211}$, $R^{213}$ to $R^{216}$ and $R^{218}$ to $R^{221}$ each independently represent a hydrogen atom, an alkyl group, an alkenyl group, an alkynyl group, an alkoxy group, an alkylthio group, an aryl group, an aryloxy group, an arylthio group, an amino group, a heterocyclic group or a halogen atom; at least one of $R^{207}$ and $R^{208}$ is an alkyl group; at least one of $R^{210}$ and $R^{211}$ is an alkyl group;

$R^{201}$ and $R^{204}$ each independently represent a hydrogen atom, an alkyl group, an alkenyl group, an alkynyl group, an alkylthio group or a halogen atom;

$R^{201}$ and $R^{202}$, $R^{204}$ and $R^{205}$, $R^{207}$ and $R^{208}$, $R^{210}$ and $R^{211}$, any of $R^{213}$ to $R^{216}$, and any of $R^{218}$ to $R^{221}$ may be bonded with each other to form a ring;

the two $R^{206}$'s and the two $R^{209}$'s are the same or different from each other, and each represent a hydrogen atom, an alkyl group, an alkenyl group or an alkynyl group, but $R^{206}$'s or $R^{209}$'s are not bonded with each other for forming a ring; the two $R^{212}$'s and the two $R^{217}$'s are the same or different from each other, and each represent a hydrogen atom, an alkyl group, an alkenyl group or an alkynyl group, but $R^{212}$'s or $R^{217}$'s are not bonded with each other for forming a ring;

m7 to m10 each independently represent an integer of 1 to 5;

Z represents a monodentate or bidentate ligand; and q1 to q3 each independently represent 1 or 2.

2. The metal complex dye according to claim 1, which is represented by Formula (XIII) or Formula (XV).

3. The metal complex dye according to claim 1, which is represented by Formula (XIII).

4. The metal complex dye according to claim 1, wherein $R^{200}$ and $R^{203}$ in Formula (XIII) each are an alkynyl group having 5 to 15 carbon atoms.

5. The metal complex dye according to claim 1, wherein $R^{201}$ and $R^{204}$ in Formula (XIII) each are a hydrogen atom.

6. The metal complex dye according to claim 1, wherein $R^{202}$ and $R^{205}$ in Formula (XIII) each are a hydrogen atom or an alkyl group.

7. The metal complex dye according to claim 1, wherein $R^{206}$ and $R^{209}$ in Formula (XIV) each are a branched or straight-chain alkyl group having 4 to 10 carbon atoms.

8. The metal complex dye according to claim 1, wherein $R^{212}$ and $R^{217}$ in Formula (XV) each are a branched or straight-chain alkyl group having 4 to 10 carbon atoms.

9. The metal complex dye according to claim 1, wherein $R^{213}$ to $R^{216}$ and $R^{218}$ to $R^{221}$ in Formula (XV) each are a hydrogen atom.

10. The metal complex dye according to claim 1, wherein Z is isothiocyanate, isocyanate or isoselenocyanate.

11. A photoelectric conversion element, comprising semiconductor fine particles sensitized with the metal complex dye according to claim 1.

12. A photoelectric conversion element, comprising semiconductor fine particles sensitized with a plurality of dyes, at least one of which is the metal complex dye according to claim 1.

13. The photoelectric conversion element according to claim 12, at least one of the plurality of dyes has a maximum absorption wavelength of 600 nm or more on the longest wavelength side in THF/water (=6:4, trifluoroacetic acid 0.1 v/v %) solution.

14. A photoelectric conversion element, comprising:
an electrically conductive support; and
a semiconductor layer arranged so as to cover an electrically conductive surface of the electrically conductive support;
the metal complex dye according to claim 1, and a co-adsorbent having one carboxyl group or salt thereof are carried on the surface of semiconductor particles of the semiconductor layer; and
wherein the co-adsorbent is represented by Formula (XVI):

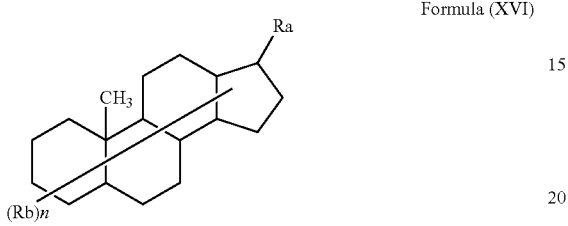

Formula (XVI)

wherein Ra represents an alkyl group having only one acidic group or salt thereof; Rb represents a substituent; n represents an integer of 0 or more; and when n is an integer of 2 or more, Rb's may be the same or different from each other.

15. A dye-sensitized solar cell, comprising the photoelectric conversion element according to claim 11.

16. A dye-sensitized solar cell, comprising the photoelectric conversion element according to claim 12.

17. A dye-sensitized solar cell, comprising the photoelectric conversion element according to claim 14.

* * * * *